US010227528B2

(12) United States Patent
Jatsch et al.

(10) Patent No.: US 10,227,528 B2
(45) Date of Patent: Mar. 12, 2019

(54) MATERIALS FOR ORGANIC ELECTROLUMINESCENT DEVICES

(71) Applicant: Merck Patent GmbH, Darmstadt (DE)

(72) Inventors: Anja Jatsch, Frankfurt Am Main (DE); Christof Pflumm, Darmstadt (DE); Amir Hossain Parham, Frankfurt Am Main (DE); Thomas Eberle, Landau (DE); Philipp Stoessel, Frankfurt Am Main (DE); Jonas Valentin Kroeber, Frankfurt Am Main (DE); Rouven Linge, Darmstadt (DE)

(73) Assignee: Merck Patent GmbH (DE)

( * ) Notice: Subject to any disclaimer, the term of this patent is extended or adjusted under 35 U.S.C. 154(b) by 236 days.

(21) Appl. No.: 14/654,708

(22) PCT Filed: Nov. 27, 2013

(86) PCT No.: PCT/EP2013/003583
§ 371 (c)(1),
(2) Date: Jun. 22, 2015

(87) PCT Pub. No.: WO2014/094963
PCT Pub. Date: Jun. 26, 2014

(65) Prior Publication Data
US 2015/0337197 A1 Nov. 26, 2015

(30) Foreign Application Priority Data
Dec. 21, 2012 (EP) .................................... 12008584

(51) Int. Cl.
| | |
|---|---|
| *H01L 51/00* | (2006.01) |
| *C09K 11/02* | (2006.01) |
| *C07D 403/04* | (2006.01) |
| *C07D 495/10* | (2006.01) |
| *C07D 491/107* | (2006.01) |
| *C07D 401/04* | (2006.01) |
| *C07D 209/96* | (2006.01) |
| *C07D 409/04* | (2006.01) |
| *C07D 403/10* | (2006.01) |
| *C07D 401/14* | (2006.01) |
| *C07D 409/14* | (2006.01) |
| *C07D 405/10* | (2006.01) |
| *C07D 487/10* | (2006.01) |
| *C07D 209/86* | (2006.01) |

(Continued)

(52) U.S. Cl.
CPC .......... *C09K 11/025* (2013.01); *C07D 209/86* (2013.01); *C07D 209/96* (2013.01); *C07D 401/04* (2013.01); *C07D 401/14* (2013.01); *C07D 403/04* (2013.01); *C07D 403/10* (2013.01); *C07D 405/10* (2013.01); *C07D 409/04* (2013.01); *C07D 409/14* (2013.01); *C07D 487/10* (2013.01); *C07D 491/107* (2013.01); *C07D 495/10* (2013.01); *C09K 11/06* (2013.01); *H01L 51/006* (2013.01); *H01L 51/0061* (2013.01); *H01L 51/0067* (2013.01); *H01L 51/0068* (2013.01); *H01L 51/0071* (2013.01); *H01L 51/0072* (2013.01); *H01L 51/0073* (2013.01); *H01L 51/0074* (2013.01); *C09K 2211/1007* (2013.01); *C09K 2211/1011* (2013.01); *C09K 2211/1029* (2013.01); *C09K 2211/1033* (2013.01); *C09K 2211/1037* (2013.01); *C09K 2211/1044* (2013.01); *C09K 2211/1059* (2013.01); *C09K 2211/1088* (2013.01); *C09K 2211/1092* (2013.01); *H01L 51/5012* (2013.01); *H01L 51/5016* (2013.01); *H01L 51/5056* (2013.01); *H01L 51/5072* (2013.01); *H01L 51/5096* (2013.01); *H01L 2251/5384* (2013.01); *Y02E 10/549* (2013.01)

(58) Field of Classification Search
CPC .. C07D 209/86; C07D 209/96; C07D 401/04; C07D 401/14; C07D 403/04; C07D 403/10; C07D 405/10; C07D 409/04; C07D 409/14; C07D 487/10; C07D 491/107; C07D 495/10; C09K 11/025; C09K 11/06; C09K 2211/1007; C09K 2211/1011
USPC ....... 428/690, 691, 917, 411.4, 336; 427/58, 427/66; 313/500–512; 257/40, 88–104, 257/E51, E51.052; 252/301.16–301.35
See application file for complete search history.

(56) References Cited

U.S. PATENT DOCUMENTS

| | | | |
|---|---|---|---|
| 9,040,172 B2 | 5/2015 | Parham et al. | |
| 2003/0186158 A1* | 10/2003 | Yokota | ............... G03G 5/14752 430/119.6 |
| 2012/0091446 A1 | 4/2012 | Jung et al. | |

(Continued)

FOREIGN PATENT DOCUMENTS

| | | |
|---|---|---|
| CN | 102471602 A | 5/2012 |
| JP | 2012126673 A | 7/2012 |

(Continued)

OTHER PUBLICATIONS

International Search Report for PCT/EP2013/003583 dated Jan. 23, 2014.

(Continued)

*Primary Examiner* — Jennifer A Chriss
*Assistant Examiner* — Sean M DeGuire
(74) *Attorney, Agent, or Firm* — Drinker Biddle & Reath LLP

(57) ABSTRACT

The present invention relates to compounds which are suitable for use in electronic devices, and to electronic devices, in particular organic electroluminescent devices, comprising these compounds.

19 Claims, No Drawings

(51) Int. Cl.
    *C09K 11/06*     (2006.01)
    *H01L 51/50*     (2006.01)

(56) References Cited

U.S. PATENT DOCUMENTS

| | | | |
|---|---|---|---|
| 2012/0097899 | A1 | 4/2012 | Parham et al. |
| 2013/0019024 | A1 | 1/2013 | Sheth et al. |
| 2013/0256645 | A1* | 10/2013 | Min .................. C09K 11/06 257/40 |

FOREIGN PATENT DOCUMENTS

| | | | |
|---|---|---|---|
| JP | 2012531383 | A | 12/2012 |
| JP | 2012531737 | A | 12/2012 |
| JP | 2014523207 | A | 9/2014 |
| WO | WO-2011000455 | A1 | 1/2011 |
| WO | WO 2011136520 | * | 11/2011 |
| WO | WO2012074210 | A2 * | 6/2012 |
| WO | WO-2012074210 | A2 | 6/2012 |

OTHER PUBLICATIONS

English Translation of Japanese Office Action for Japanese Application No. 2015-548258, dated Sep. 26, 2017.

* cited by examiner

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2013/003583, filed Nov. 27, 2013, which claims benefit of European Application No. 12008584.0, filed Dec. 21, 2012, both of which are incorporated herein by reference in their entirety.

The present invention relates to materials for use in electronic devices, in particular in organic electroluminescent devices, and to electronic devices, in particular organic electroluminescent devices, comprising these materials.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here are increasingly organometallic complexes which exhibit phosphorescence instead of fluorescence. For quantum-mechanical reasons, an up to four-fold increase in the energy and power efficiency is possible using organometallic compounds as phosphorescence emitters. In general, however, there is still a need for improvement in the case of OLEDs, in particular also in the case of OLEDs which exhibit triplet emission (phosphorescence), for example with respect to efficiency, operating voltage and lifetime.

The properties of phosphorescent OLEDs are not only determined by the triplet emitters employed. In particular, the other materials used, such as matrix materials, hole-blocking materials, electron-transport materials, hole-transport materials and electron- or exciton-blocking materials, are also of particular importance here. Improvements in these materials can thus also result in significant improvements in the OLED properties.

In accordance with the prior art, indolocarbazole derivatives, for example in accordance with WO 2007/063754 or WO 2008/056746, indenocarbazole derivatives, for example in accordance with WO 2010/136109, or fluorene or spirobifluorene derivatives, for example in accordance with WO 2012/074210, inter alia, are employed as matrix materials for phosphorescent emitters in organic electroluminescent devices. Further improvements are desirable here, in particular with respect to the efficiency, the lifetime and the thermal stability of the materials.

The object of the present invention is the provision of compounds which are suitable for use in an OLED, in particular as matrix material for phosphorescent emitters, but also as hole-blocking material, as electron-transport material or optionally as hole-transport and/or electron-blocking material. A further object of the present invention is to provide further organic semiconductors for organic electroluminescent devices so as to provide the person skilled in the art with a greater possible choice of materials for the production of OLEDs.

Surprisingly, it has been found that certain compounds described in greater detail below achieve this object, are highly suitable for use in OLEDs and result in improvements in the organic electroluminescent device. The improvements here relate, in particular, to the lifetime and/or the operating voltage. The present invention therefore relates to these compounds and to electronic devices, in particular organic electroluminescent devices, which comprise compounds of this type.

The present invention relates to a compound of the formula (1) or formula (1A),

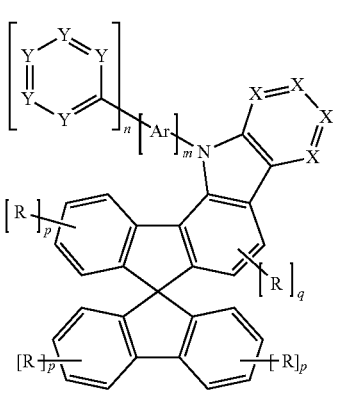

formula (1)

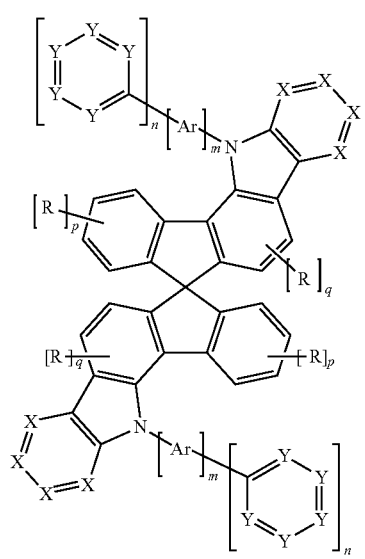

formula (1A)

where the following applies to the symbols and indices used:

Y is on each occurrence, identically or differently, $CR^1$ or N, with the proviso that at least one group Y stands for N;

X is on each occurrence, identically or differently, $CR^1$ or N; or two adjacent X stand for S, O or $NR^1$, so that a five-membered ring forms; or two adjacent X stand for a group of the following formula (2), (3) or (4),

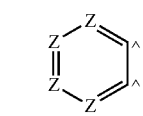

formula (2)

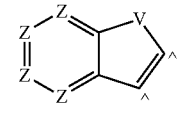

formula (3)

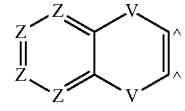

formula (4)

where ^ indicates the corresponding adjacent groups X in the formula (1);

V is on each occurrence, identically or differently, $C(R^1)_2$, $NR^1$, O, S, $BR^1$, $Si(R^1)_2$ or C=O;

Z is on each occurrence, identically or differently, $CR^1$ or N;

Ar is on each occurrence, identically or differently, an aromatic or heteroaromatic ring system having 5 to 40 aromatic ring atoms, which may be substituted by one or more radicals $R^1$;

R is selected on each occurrence, identically or differently, from the group consisting of H, D, F, Cl, Br, I, CN, $N(Ar^1)_2$, a straight-chain alkyl group having 1 to 40 C atoms or a branched or cyclic alkyl group having 3 to 40 C atoms, each of which may be substituted by one or more radicals $R^2$, where one or more non-adjacent $CH_2$ groups may be replaced by $R^2C=CR^2$, C≡C or O and where one or more H atoms may be replaced by D or F, or an aromatic ring system having 6 to 60 aromatic ring atoms, which may be substituted by one or more radicals $R^2$; two adjacent substituents R here may form a monocyclic or polycyclic, aliphatic or aromatic ring system, which may be substituted by one or more radicals $R^2$;

$R^1$ is selected on each occurrence, identically or differently, from the group consisting of H, D, F, Cl, Br, I, CN, $NO_2$, $N(Ar^1)_2$, $N(R^2)_2$, $C(=O)Ar^1$, $C(=O)R^2$, $P(=O)(Ar^1)_2$, $P(Ar^1)_2$, $B(Ar^1)_2$, $Si(Ar^1)_3$, $Si(R^2)_3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^2$, where one or more non-adjacent $CH_2$ groups may be replaced by $R^2C=CR^2$, C≡C, $Si(R^2)_2$, C=O, C=S, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals $R^2$, an aryloxy or heteroaryloxy group having 5 to 60 aromatic ring atoms, which may be substituted by one or more radicals $R^2$; two adjacent substituents $R^1$ here may optionally form a monocyclic or polycyclic, aliphatic, aromatic or heteroaromatic ring system, which may be substituted by one or more radicals $R^2$;

$Ar^1$ is on each occurrence, identically or differently, an aromatic or heteroaromatic ring system having 5-30 aromatic ring atoms, which may be substituted by one or more non-aromatic radicals $R^2$; two radicals $Ar^1$ here which are bonded to the same N atom or P atom may also be bridged to one another by a single bond or a bridge selected from $N(R^2)$, $C(R^2)_2$, O or S;

$R^2$ is selected on each occurrence, identically or differently, from the group consisting of H, D, F, CN, an aliphatic hydrocarbon radical having 1 to 20 C atoms, or an aromatic or heteroaromatic ring system having 5 to 30 aromatic ring atoms, in which one or more H atoms may be replaced by D, F, Cl, Br, I or CN, where two or more adjacent substituents $R^2$ may form a mono- or polycyclic, aliphatic ring system with one another;

m, n are on each occurrence, identically or differently, 0 or 1, with the proviso that m+n≥1;

p is on each occurrence, identically or differently, 0, 1, 2, 3 or 4;

q is 0, 1 or 2.

An aryl group in the sense of this invention contains 6 to 60 C atoms; a heteroaryl group in the sense of this invention contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (anellated) aryl or heteroaryl group, for example naphthalene, anthracene, phenanthrene, quinoline, isoquinoline, etc. Aromatic groups which are linked to one another by a single bond, such as, for example, biphenyl, are, by contrast, not referred to as aryl or heteroaryl group, but instead as aromatic ring system.

An aromatic ring system in the sense of this invention contains 6 to 60 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be connected by a non-aromatic unit, such as, for example, a C, N or O atom. Thus, for example, systems such as fluorene, 9,9'-spirobifluorene, 9,9-diarylfluorene, triarylamine, diaryl ether, stilbene, etc., are also intended to be taken to be aromatic ring systems for the purposes of this invention, as are systems in which two or more aryl groups are connected, for example, by a short alkyl group.

For the purposes of the present invention, an aliphatic hydrocarbon radical or an alkyl group or an alkenyl or alkynyl group, which may contain 1 to 40 C atoms and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups in accordance with the present invention may be straight-chain, branched or cyclic, where one or more non-adjacent $CH_2$ groups may be replaced by the above-mentioned groups; furthermore, one or more H atoms may also be replaced by D, F, Cl, Br, I, CN or $NO_2$, preferably F, Cl or CN, further preferably F or CN, particularly preferably CN.

An aromatic or heteroaromatic ring system having 5-60 aromatic ring atoms, which may also in each case be substituted by the above-mentioned radicals $R^2$ or a hydrocarbon radical and which may be linked via any desired positions on the aromatic or heteroaromatic ring system, is taken to mean, in particular, groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from a combination of these systems.

Adjacent radicals or adjacent substituents in the sense of the present application are taken to mean substituents which are bonded to C atoms which are in turn bonded directly to one another or substituents which are bonded to the same C atom.

In a preferred embodiment of the invention, X stands, identically or differently on each occurrence, for $CR^1$ or N, where a maximum of one group X per ring stands for N; or two adjacent groups X stand for a group of the formula (2) or (3), in particular formula (3), where Z stands, identically or differently on each occurrence, for $CR^1$ and V stands, identically or differently on each occurrence, for $NR^1$, $C(R^1)_2$, O or S. Furthermore preferably, adjacent radicals $R^1$ which are present on X do not form a ring with one another. Particularly preferably, X stands, identically or differently on each occurrence, for $CR^1$.

Preferred embodiments of the compounds of the formula (1) are the compounds of the following formulae (5) to (11) and preferred embodiments of the compounds of the formula (1A) are the compounds of the following formula (12),

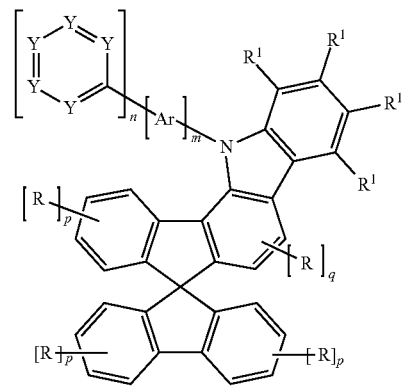

formula (5)

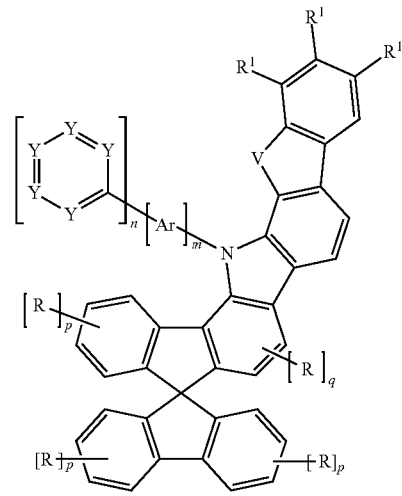

formula (6)

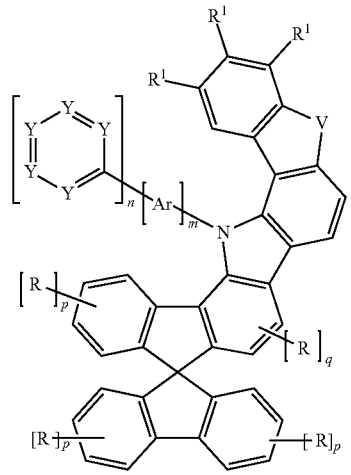

formula (7)

formula (8)

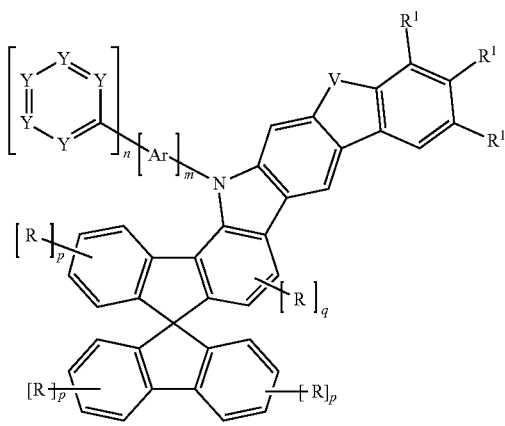

formula (9)

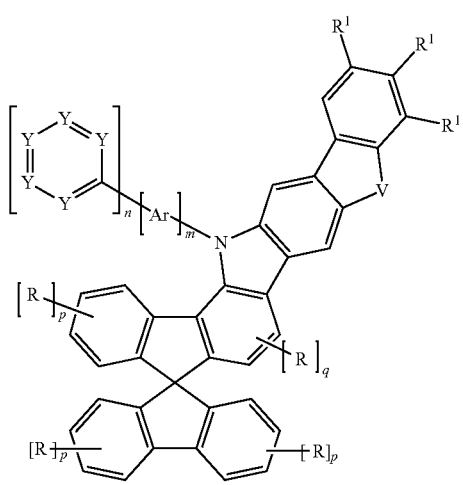

formula (10)

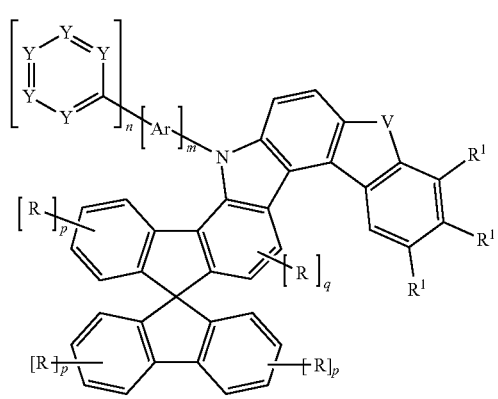

formula (11)

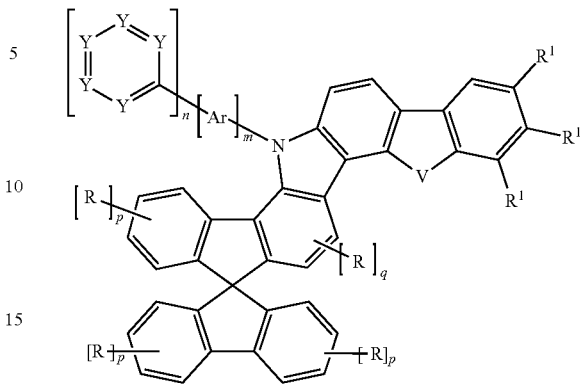

formula (12)

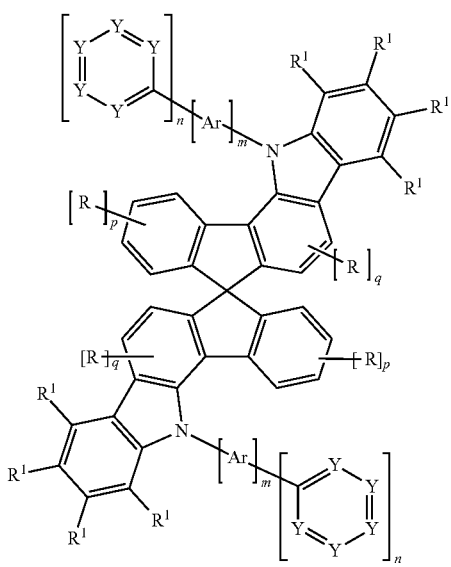

where the symbols and indices used have the meanings given above. V here preferably stands for $NR^1$, $C(R^1)_2$, O or S. It may be preferred if, for $V=C(R^1)_2$, the two radicals $R^1$ form a ring with one another and thus form a spiro system.

In a preferred embodiment of the invention, p is on each occurrence, identically or differently, 0, 1 or 2, particularly preferably 0 or 1 and very particularly preferably equal to 0.

Furthermore preferably, q is equal to 0 or 1, particularly preferably equal to 0.

Particularly preferred embodiments of the structures of the formulae (5) to (12) are the structures of the formulae (5a) to (12a), formula (5a)
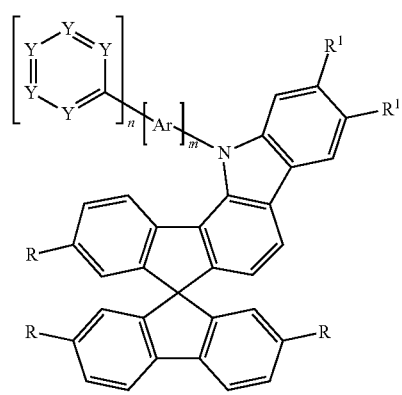
formula (6a)
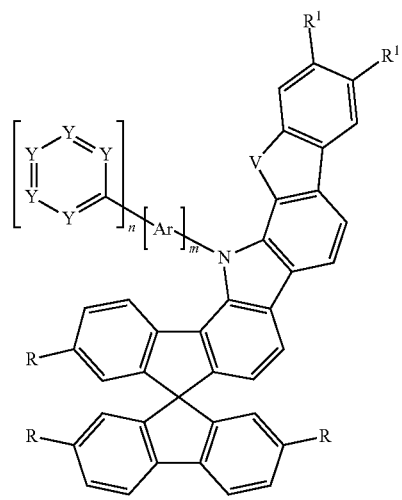
formula (7a)
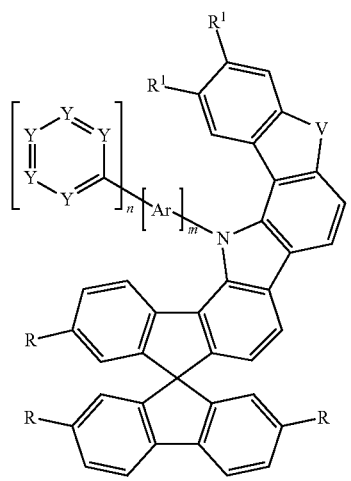
formula (8a)
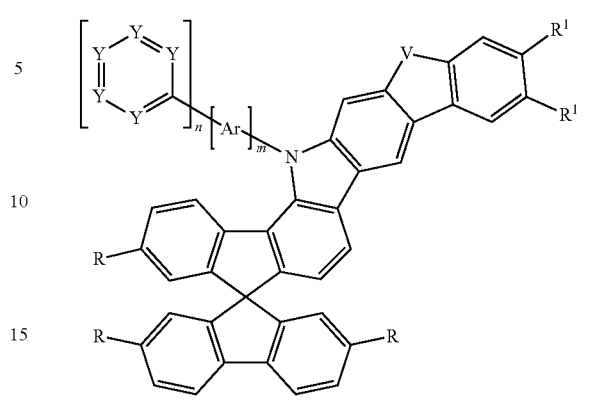
formula (9a)
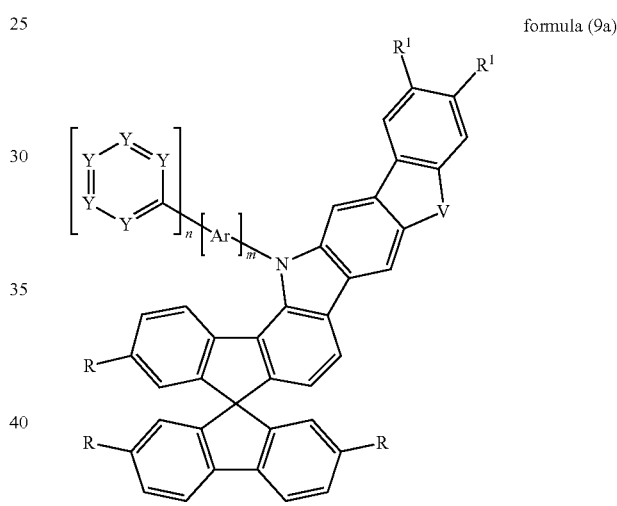
formula (10a)
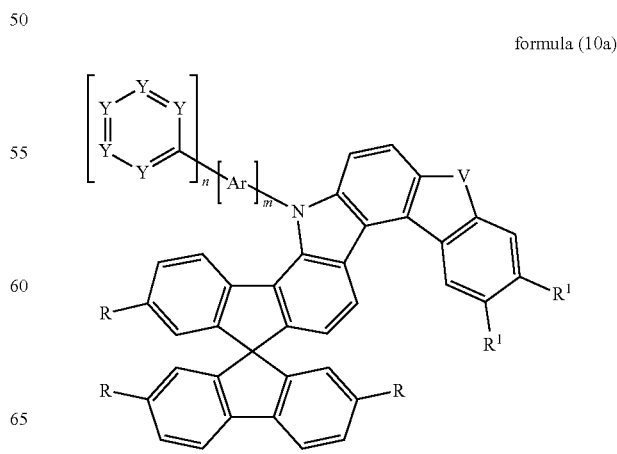

-continued formula (11a)

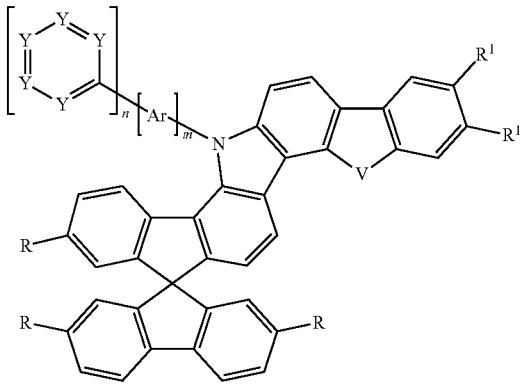

formula (12a)

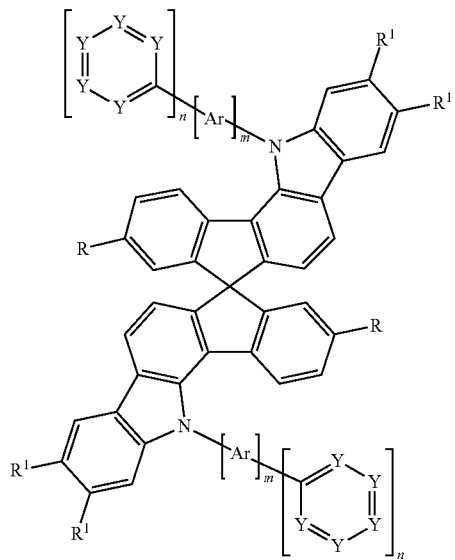

where the symbols and indices used have the meanings given above.

In a preferred embodiment of the invention, R is selected, identically or differently on each occurrence, from the group consisting of H, F, CN, N(Ar$^1$)$_2$, a straight-chain alkyl group having 1 to 10 C atoms or a branched or cyclic alkyl group having 3 to 10 C atoms or an aromatic ring system having 6 to 30 aromatic ring atoms, which may be substituted by one or more non-aromatic radicals R$^2$. In a particularly preferred embodiment of the invention, R is selected, identically or differently on each occurrence, from the group consisting of H, a straight-chain alkyl group having 1 to 4 C atoms or a branched or cyclic alkyl group having 3 to 8 C atoms, in particular is H. If the compound according to the invention is employed as monomer for the production of a polymer, it may also be preferred for two substituents R to stand for Br or I and for the polymerisation to be carried out via these groups.

In a further preferred embodiment of the invention, R$^1$ is selected, identically or differently on each occurrence, from the group consisting of H, D, F, Br, CN, N(Ar$^1$)$_2$, C(=O) Ar$^1$, P(=O)(Ar$^1$)$_2$, a straight-chain alkyl or alkoxy group having 1 to 10 C atoms or a branched or cyclic alkyl or alkoxy group having 3 to 10 C atoms or an alkenyl or alkynyl group having 2 to 10 C atoms, each of which may be substituted by one or more radicals R$^2$, where one or more non-adjacent CH$_2$ groups may be replaced by O and where one or more H atoms may be replaced by D or F, an aromatic or heteroaromatic ring system having 5 to 30 aromatic ring atoms, which may in each case be substituted by one or more radicals R$^2$. R$^1$ is particularly preferably selected, identically or differently on each occurrence, from the group consisting of H, N(Ar$^1$)$_2$, a straight-chain alkyl group having 1 to 4 C atoms or a branched or cyclic alkyl group having 3 to 8 C atoms, each of which may be substituted by one or more radicals R$^2$, or an aromatic or heteroaromatic ring system having 5 to 18 aromatic ring atoms, which may in each case be substituted by one or more radicals R$^2$.

If R stands for an aromatic ring system or if R$^1$ stands for an aromatic or heteroaromatic ring system, this R or R$^1$ is then preferably selected, identically or differently on each occurrence, from the same groups as indicated below as suitable groups for Ar.

In compounds which are processed by vacuum evaporation, the alkyl groups preferably have not more than five C atoms, particularly preferably not more than 4 C atoms, very particularly preferably not more than 1 C atom. For compounds which are processed from solution, suitable compounds are also those which are substituted by alkyl groups, in particular branched alkyl groups, having up to 10 C atoms or which are substituted by oligoarylene groups, for example ortho-, meta-, para- or branched terphenyl or quaterphenyl groups.

In a preferred embodiment of the invention, n=1 and m=0. In a further preferred embodiment of the invention, n=0 and m=1. In still a further preferred embodiment of the invention, n=m=1.

Preferred groups Ar are aromatic or heteroaromatic ring systems having 5 to 24 aromatic ring atoms, which may in each case be substituted by one or more radicals R$^1$. Suitable groups Ar are selected from benzene, ortho-, meta- or para-biphenyl, ortho-, meta-, para- or branched terphenyl, ortho-, meta-, para- or branched quaterphenyl, 1-, 2- or 3-fluorenyl, 1-, 2-, 3- or 4-spirobifluorenyl, 1- or 2-naphthyl, pyrrole, furan, thiophene, indole, benzofuran, benzothiophene, 1-, 2- or 3-carbazole, 1-, 2- or 3-dibenzofuran, 1-, 2- or 3-dibenzothiophene, indenocarbazole, indolocarbazole, 2-, 3- or 4-pyridine, 2-, 4- or 5-pyrimidine, pyrazine, pyridazine, triazine, anthracene, phenanthrene, triphenylene, pyrene, benzanthracene, or combinations of two or three of these groups, each of which may be substituted by one or more radicals R$^1$. Ar particularly preferably stands for an aromatic ring system, in particular selected from the group consisting of benzene, ortho-, meta- or para-biphenyl, ortho-, meta-, para- or branched terphenyl and ortho-, meta-, para- or branched quaterphenyl. If a group (Het-Ar), as described in greater detail below, is also bonded to the group Ar, i.e. if n=m=1, the group (Het-Ar) is then bonded to Ar at any desired site.

In a preferred embodiment of the invention, Ar is an aromatic ring system, i.e. contains no heteroaryl groups. This applies both if n=1 and a group (Het-Ar), as described below, is also bonded to Ar and also for n=0.

In a further preferred embodiment of the invention, the aromatic groups in the group Ar, if Ar contains more than one aryl group, are not para-linked, i.e. they are preferably not para-biphenyl, para-terphenyl or para-quarterphenyl, but instead, for example, the respective ortho- or meta-linked structures.

It is furthermore preferred, if Ar contains a carbazole, pyrrole, imidazole or benzimidazole group, for this group not to be linked via a nitrogen atom, but instead via a carbon atom to the other aromatic units of Ar or to the nitrogen atom.

For n=1, the compound according to the invention contains a heteroaryl group of the following formula, which is abbreviated to (Het-Ar) below:

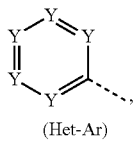

(Het-Ar)

For n=1, this group is present in the compound according to the invention and is bonded to Ar for m=1 or to the nitrogen for m=0. At least one group Y and preferably a maximum of three groups Y in the group (Het-Ar) stand for N and the other groups Y stand for $CR^1$.

Preferred embodiments are the groups of the following formulae (Het-Ar-1) to (Het-Ar-10),

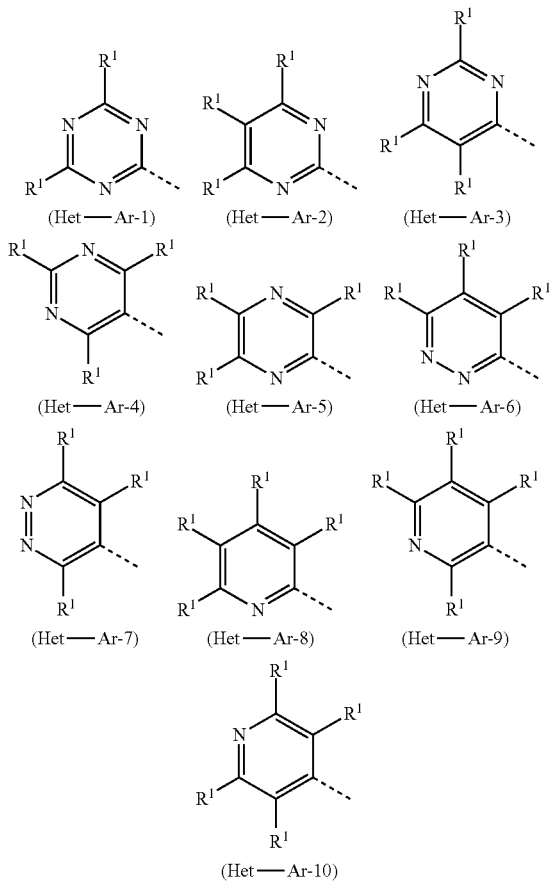

where the dashed bond represents the bond to Ar or, for m=0, the bond to the nitrogen, and the symbols used have the meanings given above.

Particular preference is given to the groups of the following formulae (Het-Ar-1a) to (Het-Ar-10b),

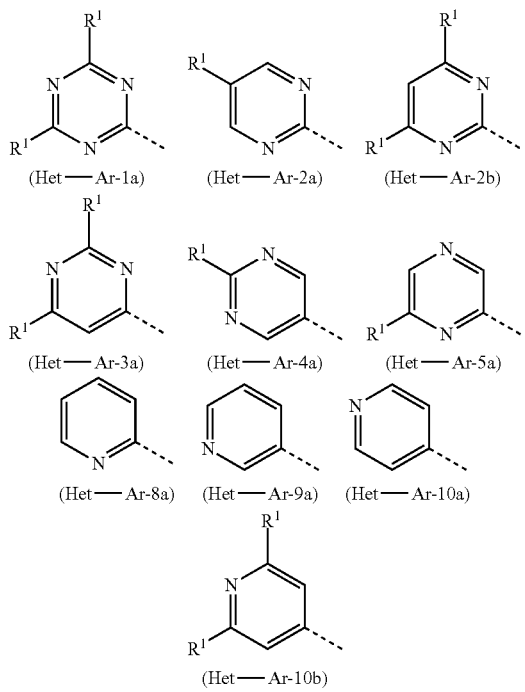

where the dashed bond represents the bond to Ar or, for m=0, the bond to the nitrogen, and the symbols used have the meanings given above.

If (Het-Ar) stands for a group (Het-Ar-1) or (Het-Ar-1a), the two substituents $R^1$ in this group then preferably stand for an aromatic or heteroaromatic ring system having 5 to 24 aromatic ring atoms, which may be substituted by one or more radicals $R^2$, in particular for phenyl, ortho-, meta- or para-biphenyl, ortho-, meta-, para- or branched terphenyl, ortho-, meta-, para- or branched quaterphenyl, 1-, 2-, 3- or 4-fluorene, 1-, 2-, 3- or 4-spirobifluorene, 1-, 2-, 3- or 4-dibenzofuran or 1-, 2-, 3- or 4-carbazole.

If (Het-Ar) stands for a group (Het-Ar-2) to (Het-Ar-10) or (Het-Ar-2a) to (Het-Ar-10a), $R^1$ in these groups then preferably stands, identically or differently on each occurrence, for H, D or an aromatic or heteroaromatic ring system having 5 to 24 aromatic ring atoms, which may be substituted by one or more radicals $R^2$, in particular for H or phenyl, ortho-, meta- or para-biphenyl, ortho-, meta-, para- or branched terphenyl or ortho-, meta-, para- or branched quaterphenyl.

The preferred embodiments mentioned above can be combined with one another as desired. In a particularly preferred embodiment of the invention, the preferences mentioned above occur simultaneously.

If the compounds of the formula (1) or the preferred embodiments are used as matrix material for a phosphorescent emitter or in a layer which is directly adjacent to a phosphorescent layer, it is furthermore preferred for the compound to contain no condensed aryl or heteroaryl groups in which more than two six-membered rings are condensed directly onto one another. In particular, it is preferred for the radicals R, $R^1$, $R^2$ and Ar to contain no condensed aryl or heteroaryl group in which two or more six-membered rings are condensed directly onto one another and for two adjacent groups X not to stand for a group of the formula (2).

Examples of preferred compounds in accordance with the embodiments indicated above are the compounds shown in the following table.

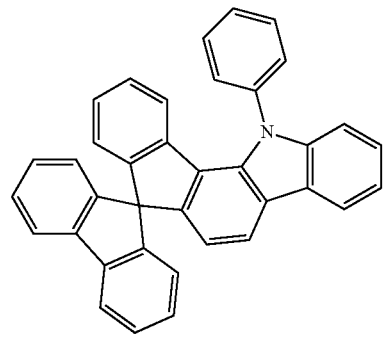 [SMILES: c1ccc(-n2c3ccccc3c3ccc4c(c32)-c2ccccc2C42c3ccccc3-c3ccccc32)cc1]
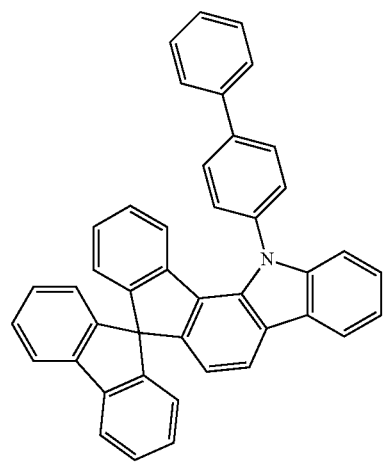 [SMILES: c1ccc(-c2ccc(-n3c4ccccc4c4ccc5c(c43)-c3ccccc3C53c4ccccc4-c4ccccc43)cc2)cc1]
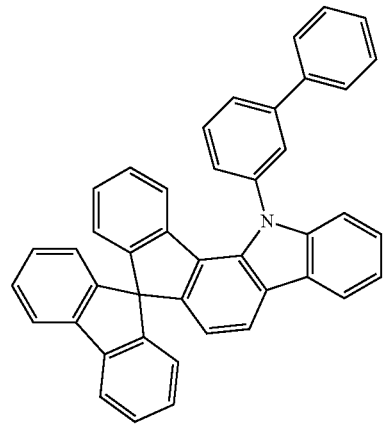 [SMILES: c1ccc(-c2cccc(-n3c4ccccc4c4ccc5c(c43)-c3ccccc3C53c4ccccc4-c4ccccc43)c2)cc1]
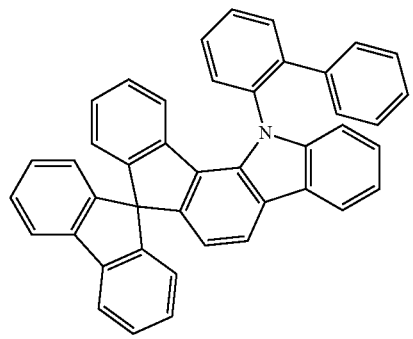 [SMILES: c1ccc(-c2ccccc2-n2c3ccccc3c3ccc4c(c32)-c2ccccc2C42c3ccccc3-c3ccccc32)cc1]

-continued
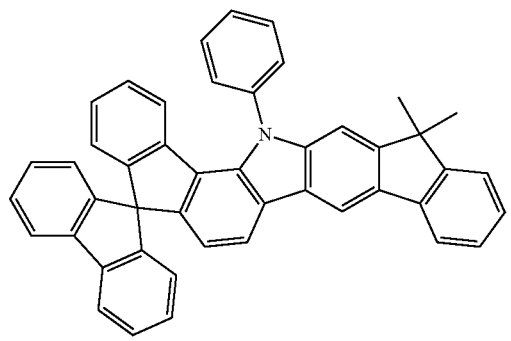 [SMILES: CC1(C)c2ccccc2-c2cc3c4ccc5c(c4n(-c4ccccc4)c3cc21)-c1ccccc1C51c2ccccc2-c2ccccc21]
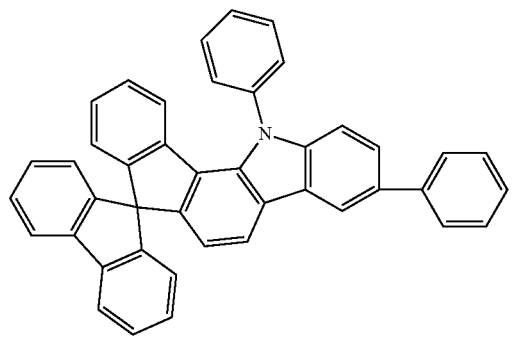 [SMILES: c1ccc(-c2ccc3c(c2)c2ccc4c(c2n3-c2ccccc2)-c2ccccc2C42c3ccccc3-c3ccccc32)cc1]
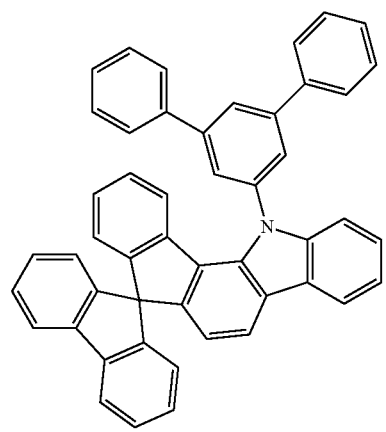 [SMILES: c1ccc(-c2cc(-c3ccccc3)cc(-n3c4ccccc4c4ccc5c(c43)-c3ccccc3C53c4ccccc4-c4ccccc43)c2)cc1]
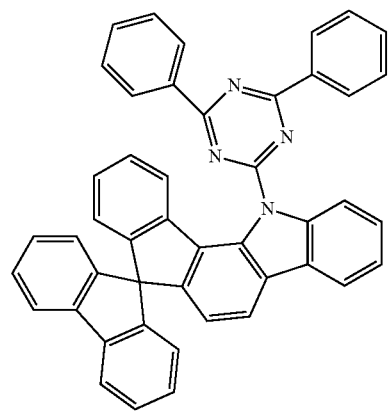

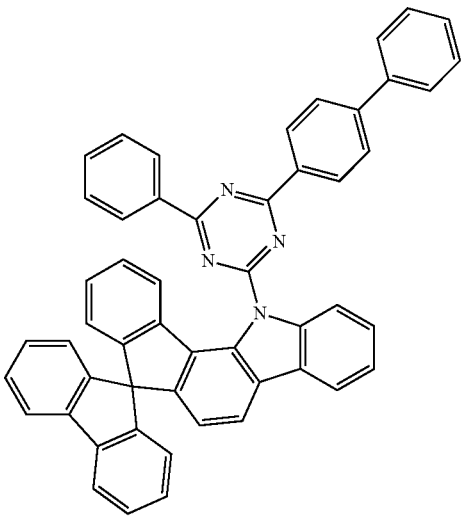 [SMILES: c1ccc(-c2ccc(-c3nc(-c4ccccc4)nc(-n4c5ccccc5c5ccc6c(c54)-c4ccccc4C64c5ccccc5-c5ccccc54)n3)cc2)cc1]
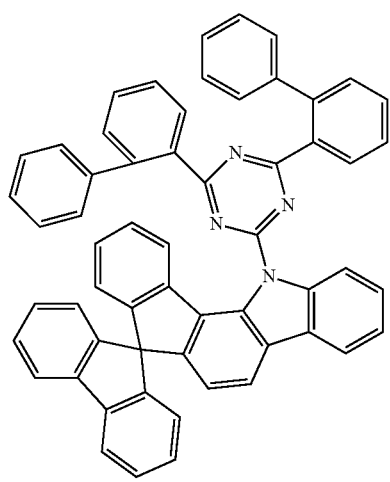 [SMILES: c1ccc(-c2ccccc2-c2nc(-c3ccccc3-c3ccccc3)nc(-n3c4ccccc4c4ccc5c(c43)-c3ccccc3C53c4ccccc4-c4ccccc43)n2)cc1]
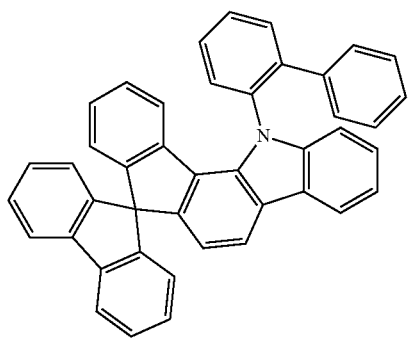 [SMILES: c1ccc(-c2ccccc2-n2c3ccccc3c3ccc4c(c32)-c2ccccc2C42c3ccccc3-c3ccccc32)cc1]

-continued
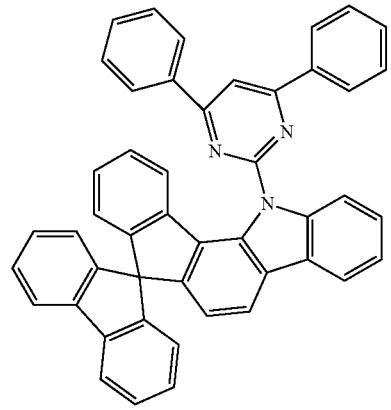 [SMILES: c1ccc(-c2cc(-c3ccccc3)nc(-n3c4ccccc4c4ccc5c(c43)-c3ccccc3C53c4ccccc4-c4ccccc43)n2)cc1]
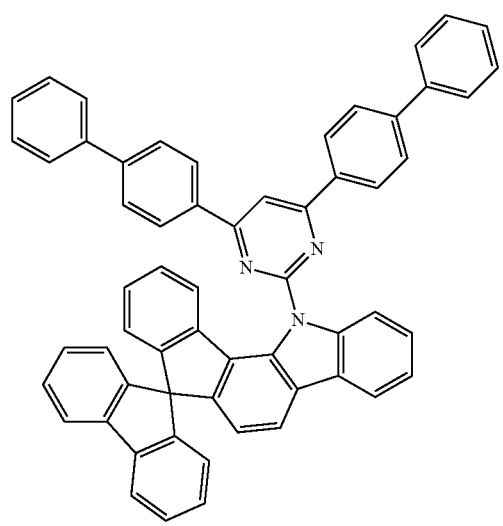 [SMILES: c1ccc(-c2ccc(-c3cc(-c4ccc(-c5ccccc5)cc4)nc(-n4c5ccccc5c5ccc6c(c54)-c4ccccc4C64c5ccccc5-c5ccccc54)n3)cc2)cc1]
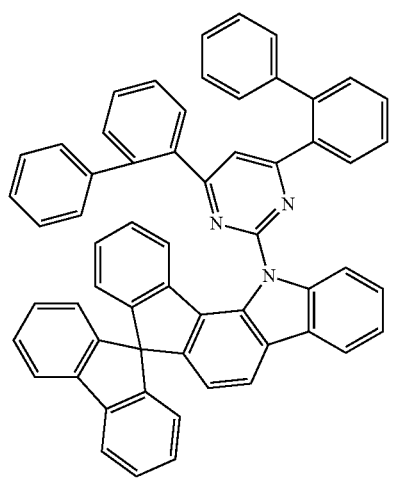 [SMILES: c1ccc(-c2ccccc2-c2cc(-c3ccccc3-c3ccccc3)nc(-n3c4ccccc4c4ccc5c(c43)-c3ccccc3C53c4ccccc4-c4ccccc43)n2)cc1]

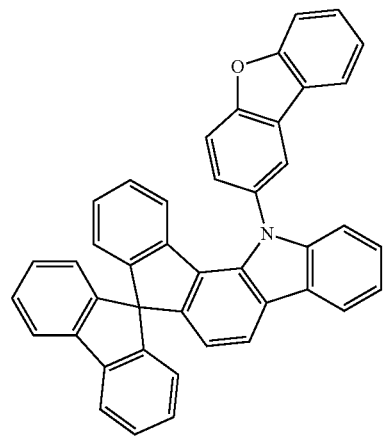
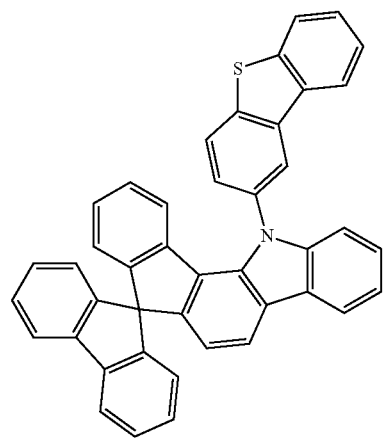 [SMILES: c1ccc2c(c1)-c1ccccc1C21c2ccccc2-c2c1ccc1c3ccccc3n(-c3ccc4sc5ccccc5c4c3)c21]
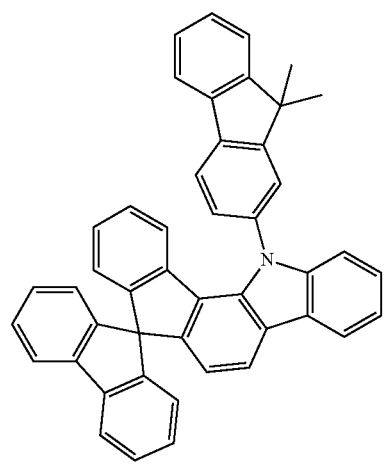 [SMILES: CC1(C)c2ccccc2-c2ccc(-n3c4ccccc4c4ccc5c(c43)-c3ccccc3C53c4ccccc4-c4ccccc43)cc21]

-continued
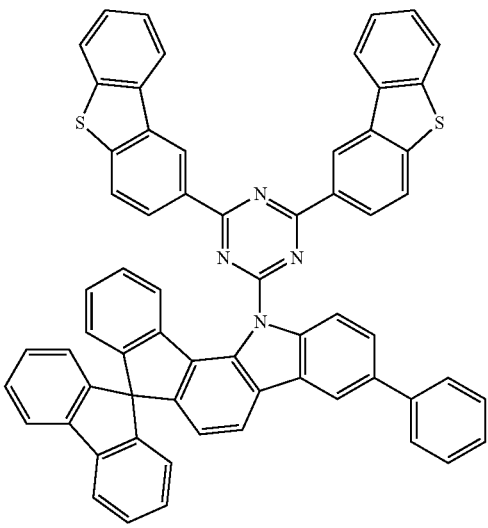
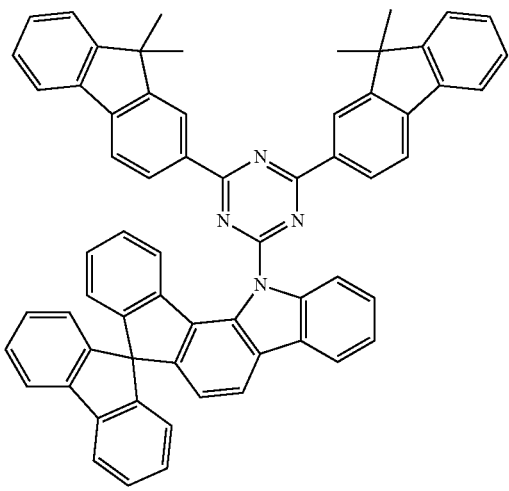 [SMILES: CC1(C)c2ccccc2-c2ccc(-c3nc(-c4ccc5c(c4)C(C)(C)c4ccccc4-5)nc(-n4c5ccccc5c5ccc6c(c54)-c4ccccc4C64c5ccccc5-c5ccccc54)n3)cc21]
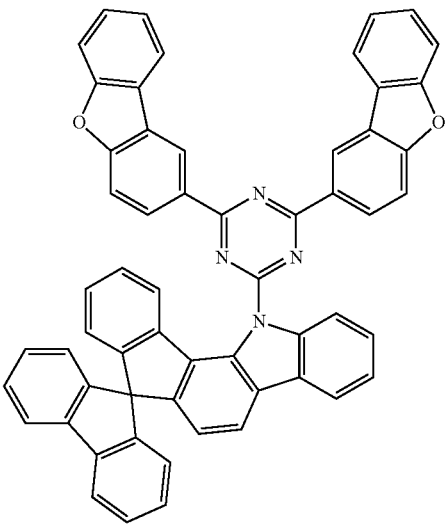 [SMILES: c1ccc2c(c1)-c1ccccc1C21c2ccccc2-c2c1ccc1c3ccccc3n(-c3nc(-c4ccc5oc6ccccc6c5c4)nc(-c4ccc5oc6ccccc6c5c4)n3)c21]

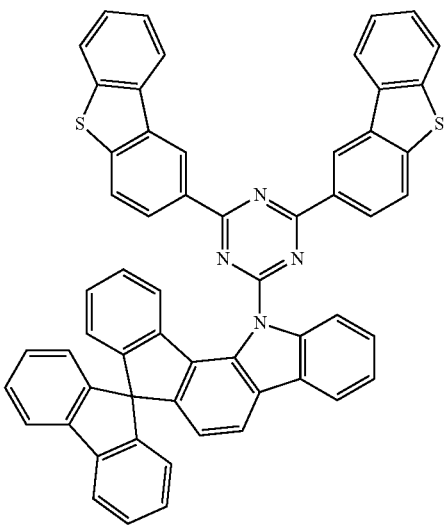 [SMILES: c1ccc2c(c1)-c1ccccc1C21c2ccccc2-c2c1ccc1c3ccccc3n(-c3nc(-c4ccc5sc6ccccc6c5c4)nc(-c4ccc5sc6ccccc6c5c4)n3)c21]
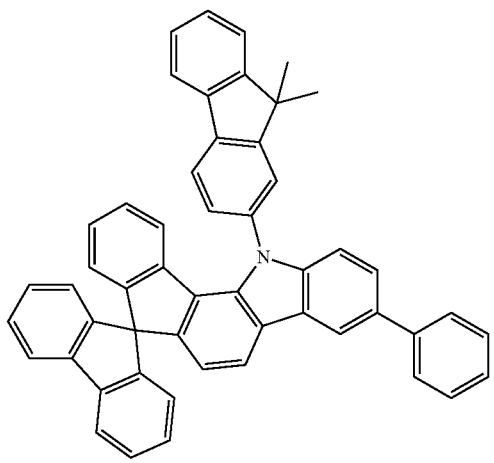 [SMILES: CC1(C)c2ccccc2-c2ccc(-n3c4ccc(-c5ccccc5)cc4c4ccc5c(c43)-c3ccccc3C53c4ccccc4-c4ccccc43)cc21]
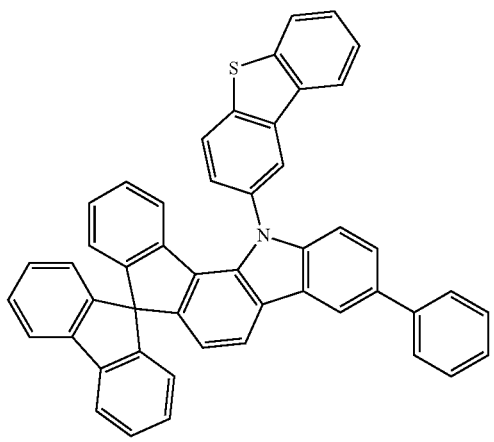 [SMILES: c1ccc(-c2ccc3c(c2)c2ccc4c(c2n3-c2ccc3sc5ccccc5c3c2)-c2ccccc2C42c3ccccc3-c3ccccc32)cc1]

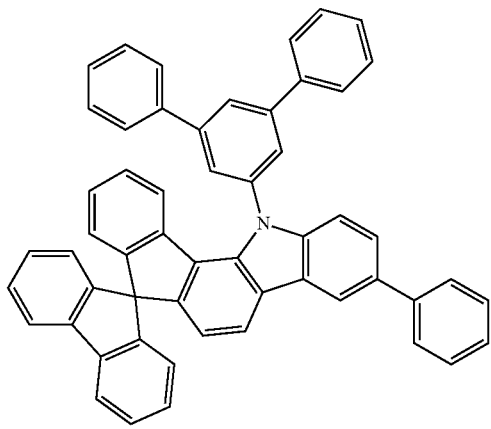 [SMILES: c1ccc(-c2cc(-c3ccccc3)cc(-n3c4ccc(-c5ccccc5)cc4c4ccc5c(c43)-c3ccccc3C53c4ccccc4-c4ccccc43)c2)cc1]
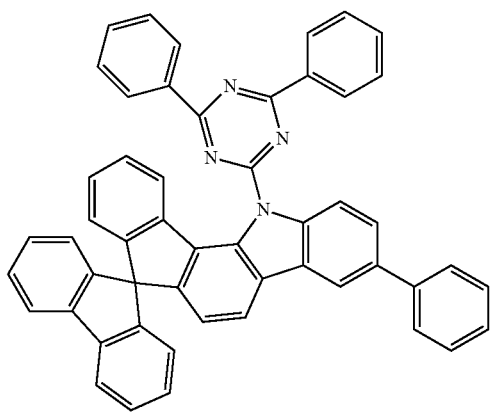
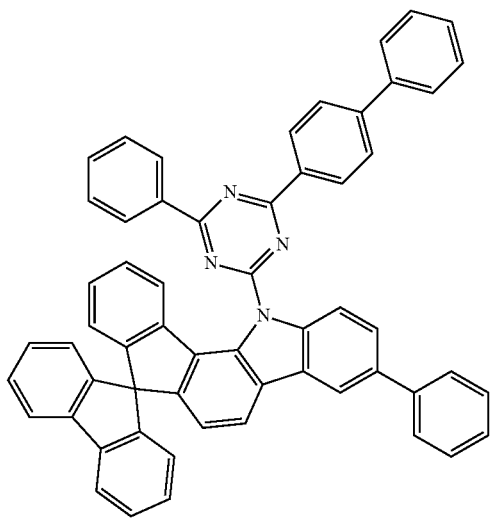 [SMILES: c1ccc(-c2ccc(-c3nc(-c4ccccc4)nc(-n4c5ccc(-c6ccccc6)cc5c5ccc6c(c54)-c4ccccc4C64c5ccccc5-c5ccccc54)n3)cc2)cc1]

-continued
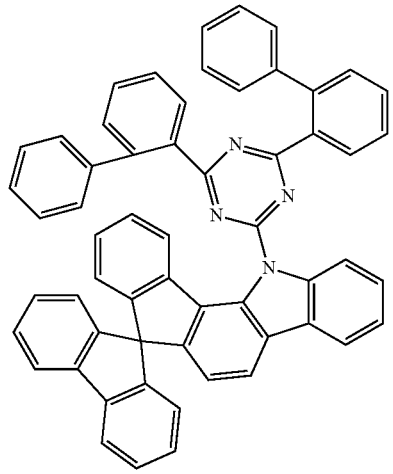 [SMILES: c1ccc(-c2ccccc2-c2nc(-c3ccccc3-c3ccccc3)nc(-n3c4ccccc4c4ccc5c(c43)-c3ccccc3C53c4ccccc4-c4ccccc43)n2)cc1]
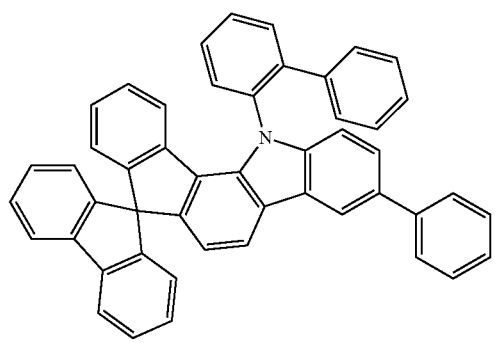 [SMILES: c1ccc(-c2ccc3c(c2)c2ccc4c(c2n3-c2ccccc2-c2ccccc2)-c2ccccc2C42c3ccccc3-c3ccccc32)cc1]
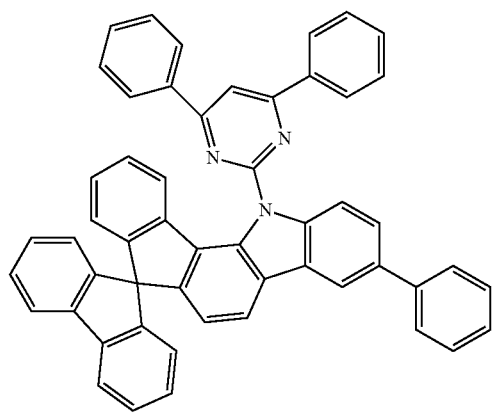 [SMILES: c1ccc(-c2ccc3c(c2)c2ccc4c(c2n3-c2nc(-c3ccccc3)cc(-c3ccccc3)n2)-c2ccccc2C42c3ccccc3-c3ccccc32)cc1]

-continued
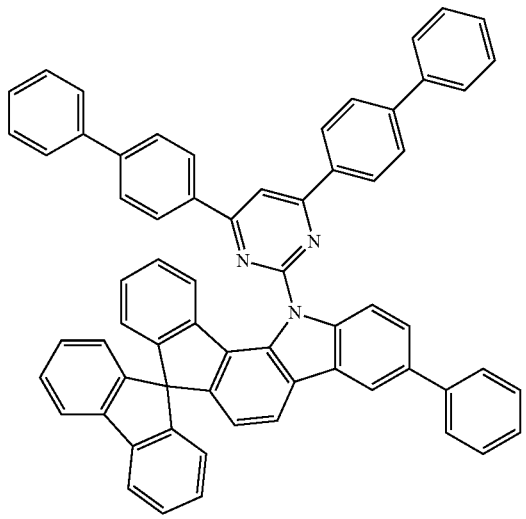 [SMILES: c1ccc(-c2ccc(-c3cc(-c4ccc(-c5ccccc5)cc4)nc(-n4c5ccc(-c6ccccc6)cc5c5ccc6c(c54)-c4ccccc4C64c5ccccc5-c5ccccc54)n3)cc2)cc1]
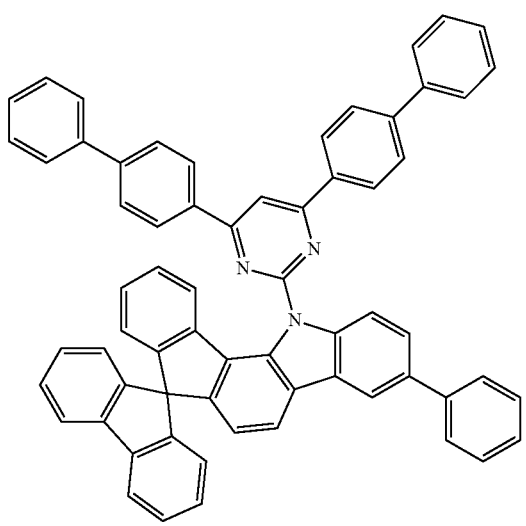 [SMILES: c1ccc(-c2ccc(-c3cc(-c4ccc(-c5ccccc5)cc4)nc(-n4c5ccc(-c6ccccc6)cc5c5ccc6c(c54)-c4ccccc4C64c5ccccc5-c5ccccc54)n3)cc2)cc1]
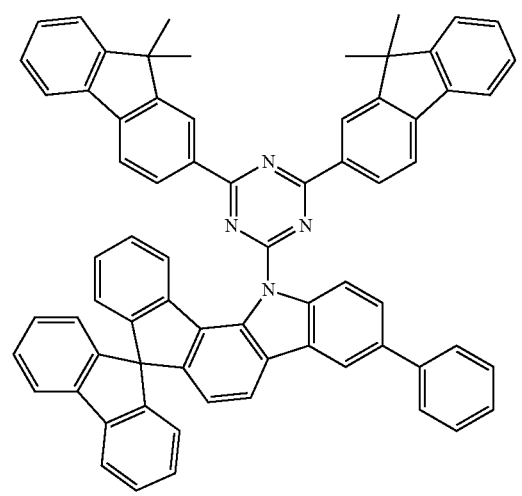 [SMILES: CC1(C)c2ccccc2-c2ccc(-c3nc(-c4ccc5c(c4)C(C)(C)c4ccccc4-5)nc(-n4c5ccc(-c6ccccc6)cc5c5ccc6c(c54)-c4ccccc4C64c5ccccc5-c5ccccc54)n3)cc21]

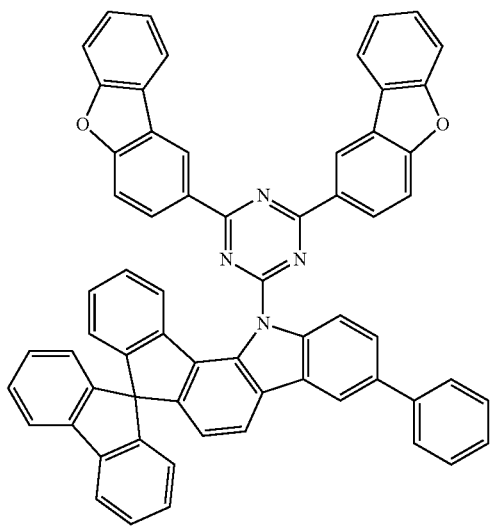 [SMILES: c1ccc(-c2ccc3c(c2)c2ccc4c(c2n3-c2nc(-c3ccc5oc6ccccc6c5c3)nc(-c3ccc5oc6ccccc6c5c3)n2)-c2ccccc2C42c3ccccc3-c3ccccc32)cc1]
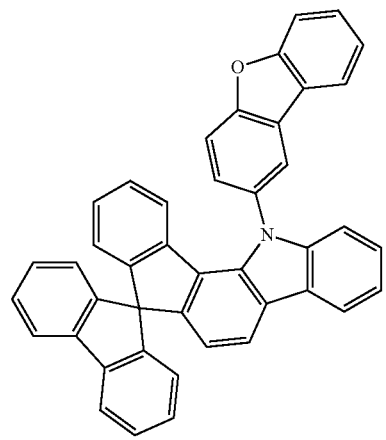 [SMILES: c1ccc2c(c1)-c1ccccc1C21c2ccccc2-c2c1ccc1c3ccccc3n(-c3ccc4oc5ccccc5c4c3)c21]
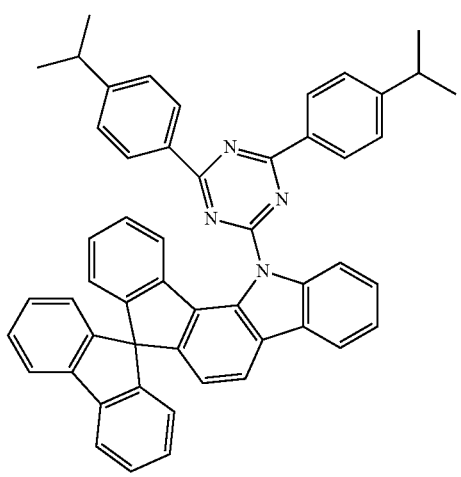 [SMILES: CC(C)c1ccc(-c2nc(-c3ccc(C(C)C)cc3)nc(-n3c4ccccc4c4ccc5c(c43)-c3ccccc3C53c4ccccc4-c4ccccc43)n2)cc1]

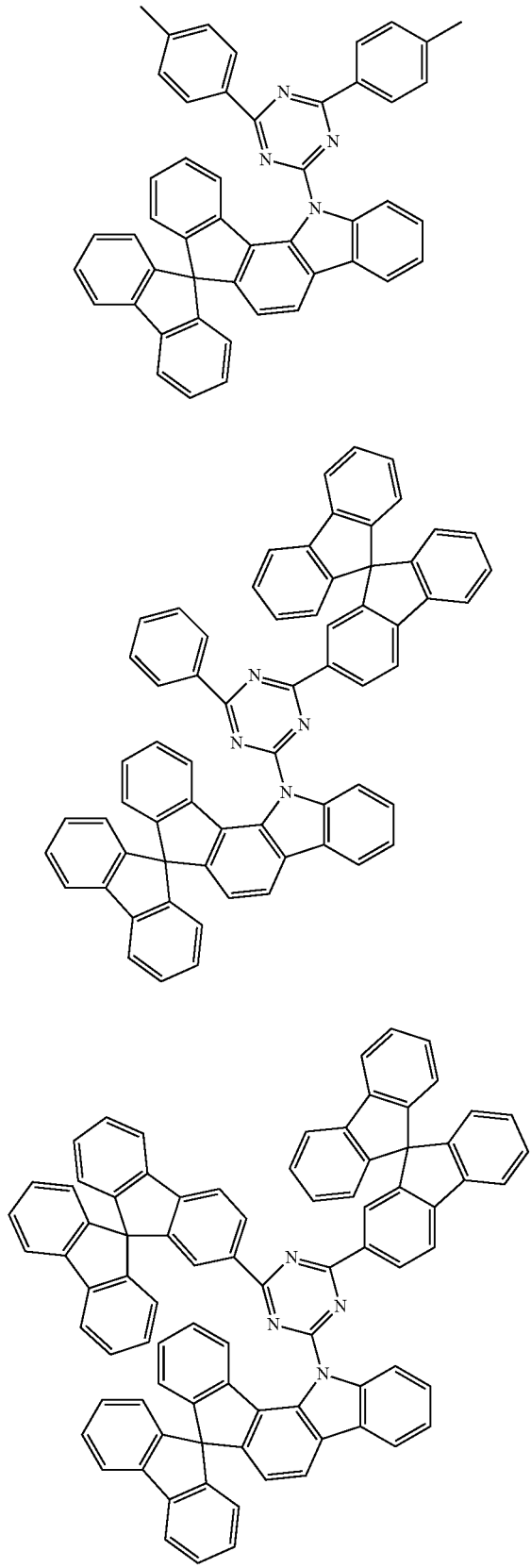

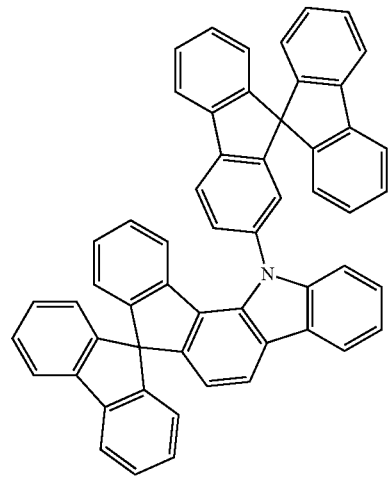 [SMILES: c1ccc2c(c1)-c1ccccc1C21c2ccccc2-c2ccc(-n3c4ccccc4c4ccc5c(c43)-c3ccccc3C53c4ccccc4-c4ccccc43)cc21]
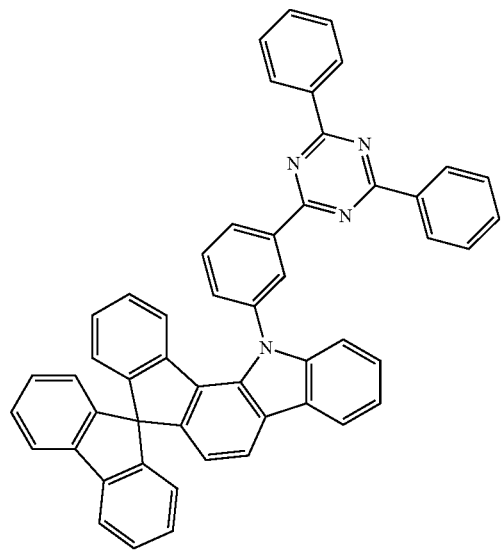 [SMILES: c1ccc(-c2nc(-c3ccccc3)nc(-c3cccc(-n4c5ccccc5c5ccc6c(c54)-c4ccccc4C64c5ccccc5-c5ccccc54)c3)n2)cc1]
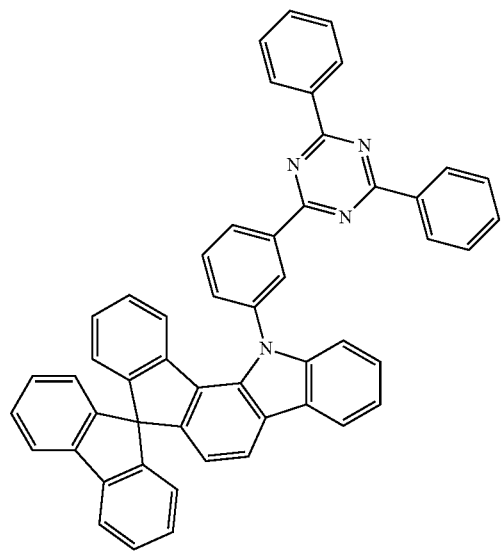 [SMILES: c1ccc(-c2nc(-c3ccccc3)nc(-c3cccc(-n4c5ccccc5c5ccc6c(c54)-c4ccccc4C64c5ccccc5-c5ccccc54)c3)n2)cc1]

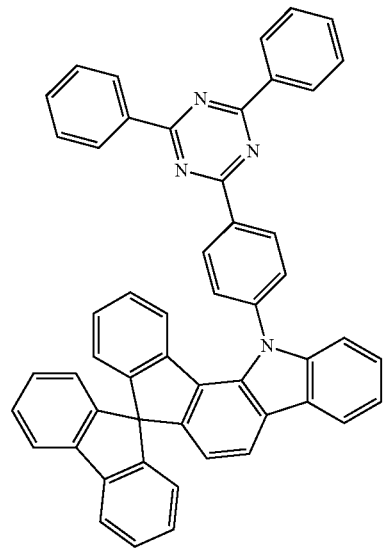 [SMILES: c1ccc(-c2nc(-c3ccccc3)nc(-c3ccc(-n4c5ccccc5c5ccc6c(c54)-c4ccccc4C64c5ccccc5-c5ccccc54)cc3)n2)cc1]
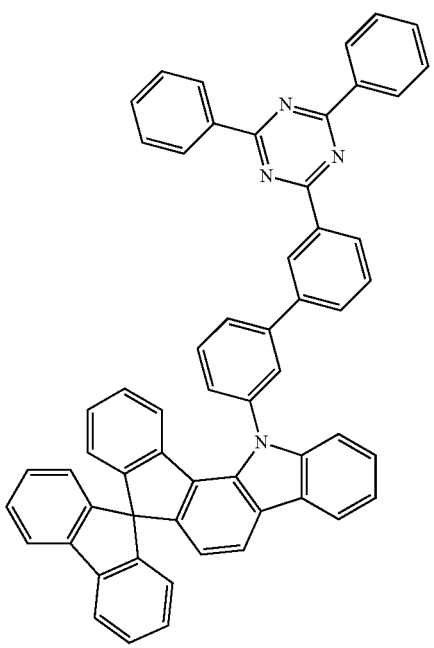 [SMILES: c1ccc(-c2nc(-c3ccccc3)nc(-c3cccc(-c4cccc(-n5c6ccccc6c6ccc7c(c65)-c5ccccc5C75c6ccccc6-c6ccccc65)c4)c3)n2)cc1]

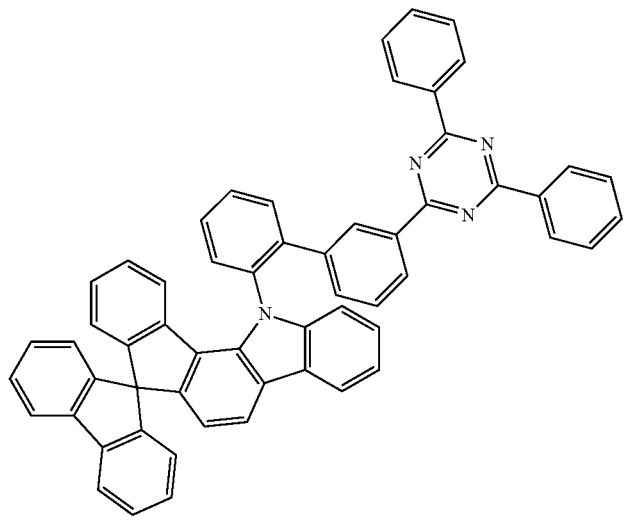 [SMILES: c1ccc(-c2nc(-c3ccccc3)nc(-c3cccc(-c4ccccc4-n4c5ccccc5c5ccc6c(c54)-c4ccccc4C64c5ccccc5-c5ccccc54)c3)n2)cc1]
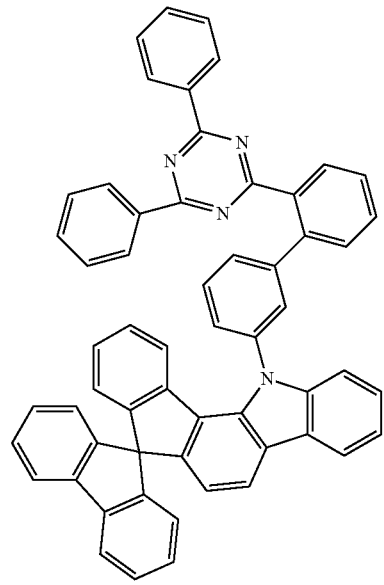 [SMILES: c1ccc(-c2nc(-c3ccccc3)nc(-c3ccccc3-c3cccc(-n4c5ccccc5c5ccc6c(c54)-c4ccccc4C64c5ccccc5-c5ccccc54)c3)n2)cc1]
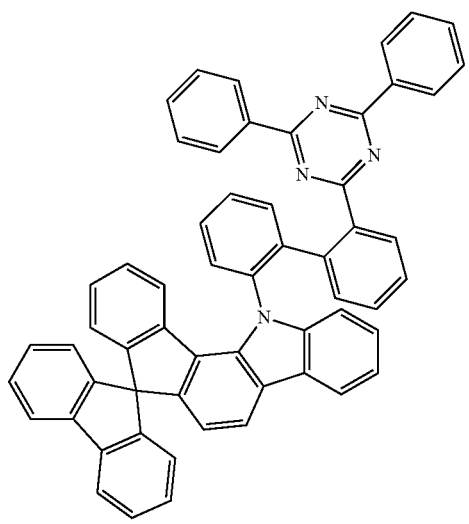 [SMILES: c1ccc(-c2nc(-c3ccccc3)nc(-c3ccccc3-c3ccccc3-n3c4ccccc4c4ccc5c(c43)-c3ccccc3C53c4ccccc4-c4ccccc43)n2)cc1]

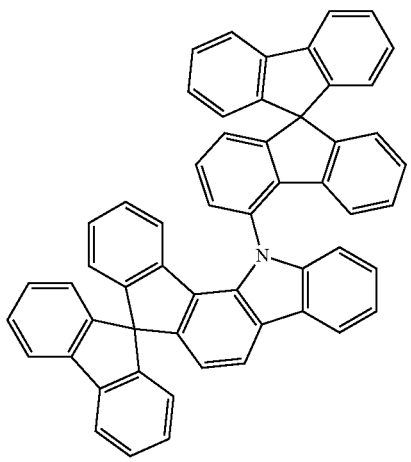 [SMILES: c1ccc2c(c1)-c1ccccc1C21c2ccccc2-c2c(-n3c4ccccc4c4ccc5c(c43)-c3ccccc3C53c4ccccc4-c4ccccc43)cccc21]

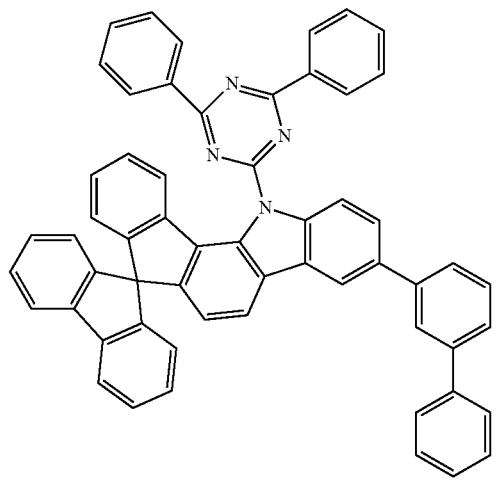 [SMILES: c1ccc(-c2cccc(-c3ccc4c(c3)c3ccc5c(c3n4-c3nc(-c4ccccc4)nc(-c4ccccc4)n3)-c3ccccc3C53c4ccccc4-c4ccccc43)c2)cc1]
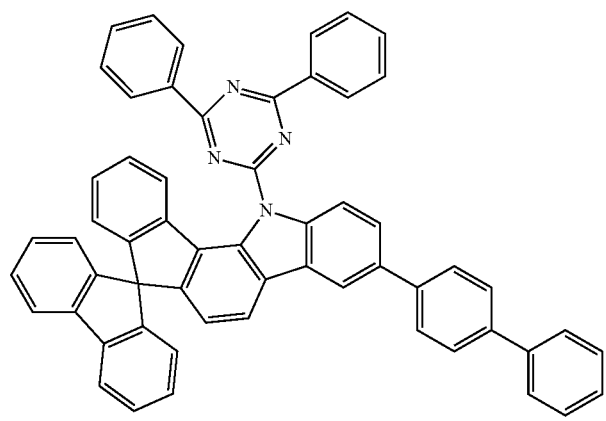 [SMILES: c1ccc(-c2ccc(-c3ccc4c(c3)c3ccc5c(c3n4-c3nc(-c4ccccc4)nc(-c4ccccc4)n3)-c3ccccc3C53c4ccccc4-c4ccccc43)cc2)cc1]
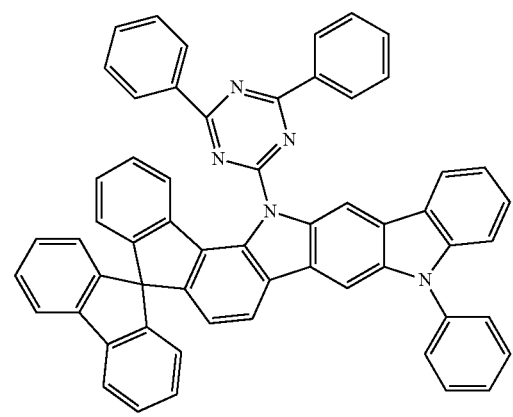 [SMILES: c1ccc(-c2nc(-c3ccccc3)nc(-n3c4cc5c6ccccc6n(-c6ccccc6)c5cc4c4ccc5c(c43)-c3ccccc3C53c4ccccc4-c4ccccc43)n2)cc1]

-continued
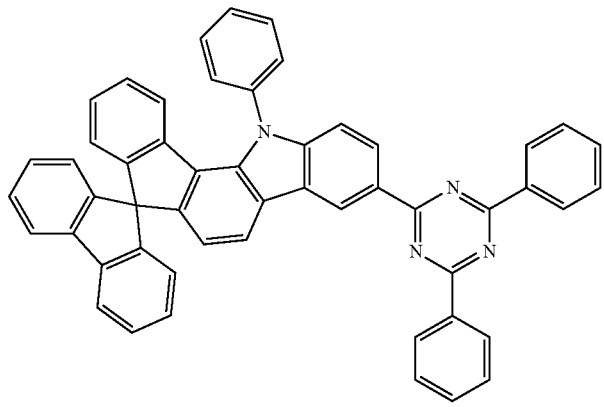 [SMILES: c1ccc(-c2nc(-c3ccccc3)nc(-c3ccc4c(c3)c3ccc5c(c3n4-c3ccccc3)-c3ccccc3C53c4ccccc4-c4ccccc43)n2)cc1]
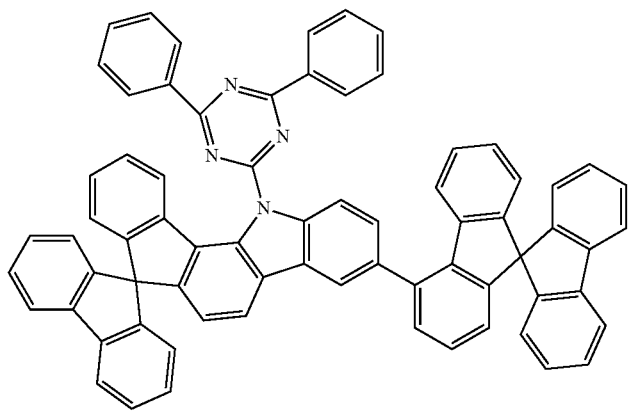 [SMILES: c1ccc(-c2nc(-c3ccccc3)nc(-n3c4ccc(-c5cccc6c5-c5ccccc5C65c6ccccc6-c6ccccc65)cc4c4ccc5c(c43)-c3ccccc3C53c4ccccc4-c4ccccc43)n2)cc1]
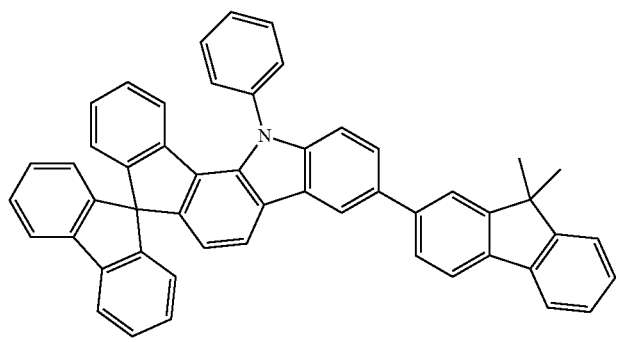 [SMILES: CC1(C)c2ccccc2-c2ccc(-c3ccc4c(c3)c3ccc5c(c3n4-c3ccccc3)-c3ccccc3C53c4ccccc4-c4ccccc43)cc21]
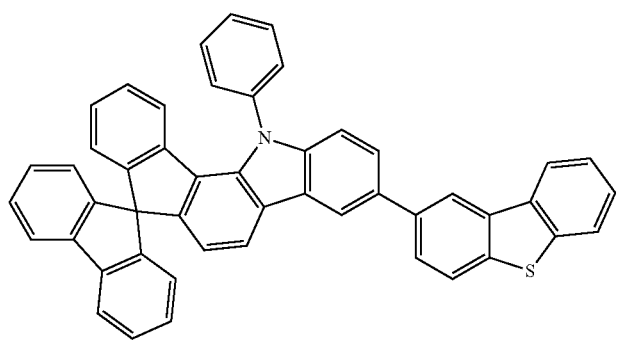 [SMILES: c1ccc(-n2c3ccc(-c4ccc5sc6ccccc6c5c4)cc3c3ccc4c(c32)-c2ccccc2C42c3ccccc3-c3ccccc32)cc1]

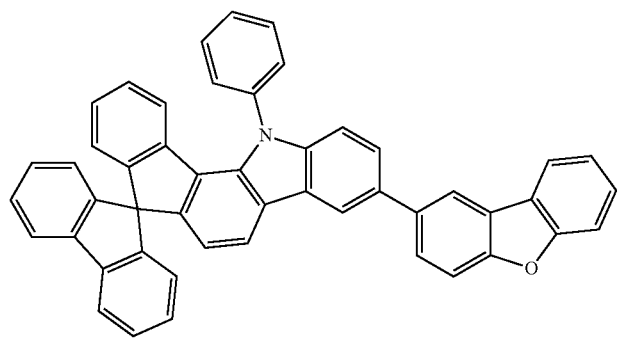 [SMILES: c1ccc(-n2c3ccc(-c4ccc5oc6ccccc6c5c4)cc3c3ccc4c(c32)-c2ccccc2C42c3ccccc3-c3ccccc32)cc1]
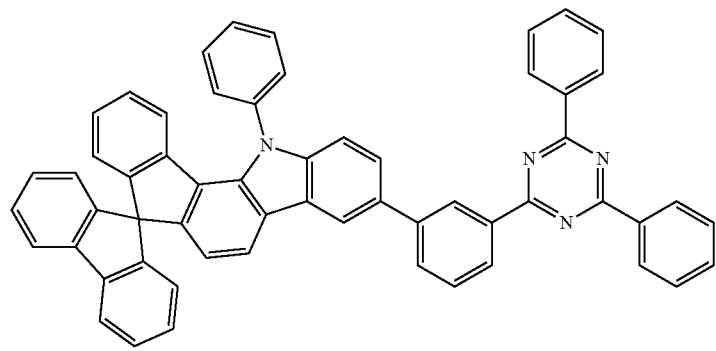 [SMILES: c1ccc(-c2nc(-c3ccccc3)nc(-c3cccc(-c4ccc5c(c4)c4ccc6c(c4n5-c4ccccc4)-c4ccccc4C64c5ccccc5-c5ccccc54)c3)n2)cc1]
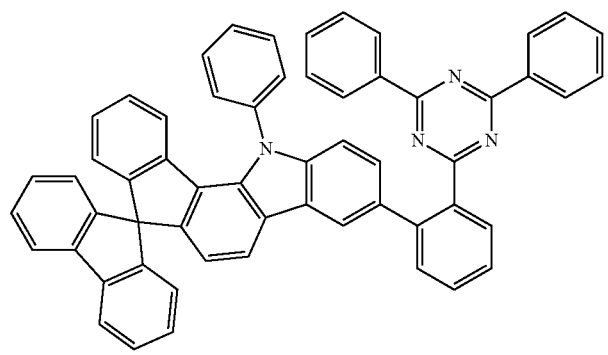 [SMILES: c1ccc(-c2nc(-c3ccccc3)nc(-c3ccccc3-c3ccc4c(c3)c3ccc5c(c3n4-c3ccccc3)-c3ccccc3C53c4ccccc4-c4ccccc43)n2)cc1]
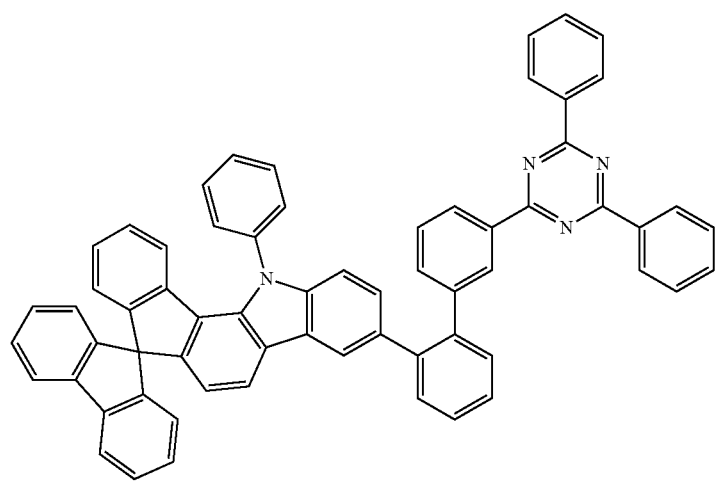 [SMILES: c1ccc(-c2nc(-c3ccccc3)nc(-c3cccc(-c4ccccc4-c4ccc5c(c4)c4ccc6c(c4n5-c4ccccc4)-c4ccccc4C64c5ccccc5-c5ccccc54)c3)n2)cc1]

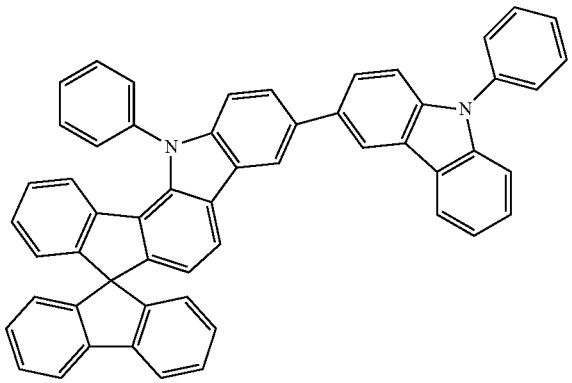 [SMILES: c1ccc(-n2c3ccccc3c3cc(-c4ccc5c(c4)c4ccc6c(c4n5-c4ccccc4)-c4ccccc4C64c5ccccc5-c5ccccc54)ccc32)cc1]
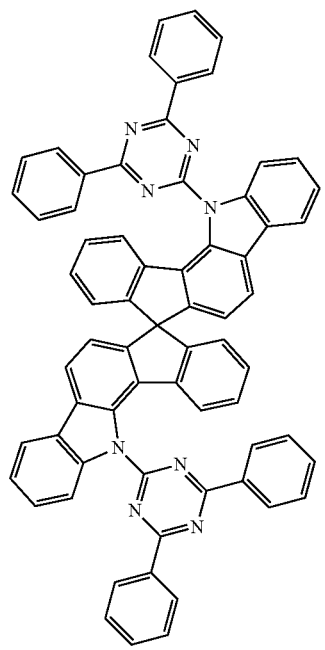 [SMILES: c1ccc(-c2nc(-c3ccccc3)nc(-n3c4ccccc4c4ccc5c(c43)-c3ccccc3C53c4ccccc4-c4c3ccc3c5ccccc5n(-c5nc(-c6ccccc6)nc(-c6ccccc6)n5)c43)n2)cc1]
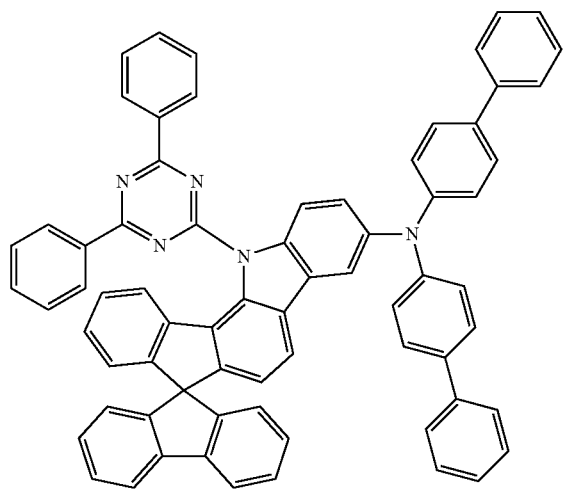 [SMILES: c1ccc(-c2ccc(N(c3ccc(-c4ccccc4)cc3)c3ccc4c(c3)c3ccc5c(c3n4-c3nc(-c4ccccc4)nc(-c4ccccc4)n3)-c3ccccc3C53c4ccccc4-c4ccccc43)cc2)cc1]

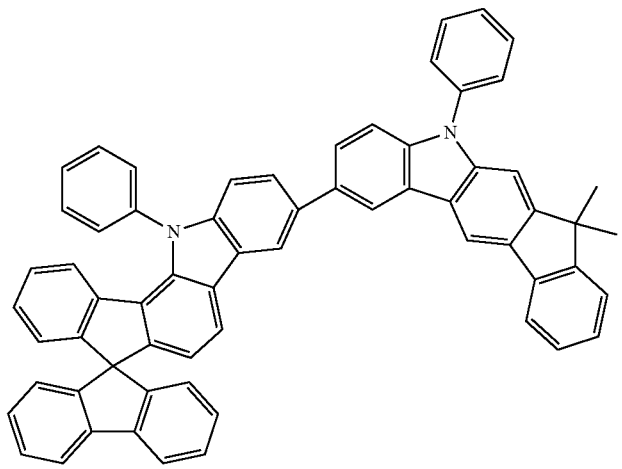 [SMILES: CC1(C)c2ccccc2-c2cc3c4cc(-c5ccc6c(c5)c5ccc7c(c5n6-c5ccccc5)-c5ccccc5C75c6ccccc6-c6ccccc65)ccc4n(-c4ccccc4)c3cc21]
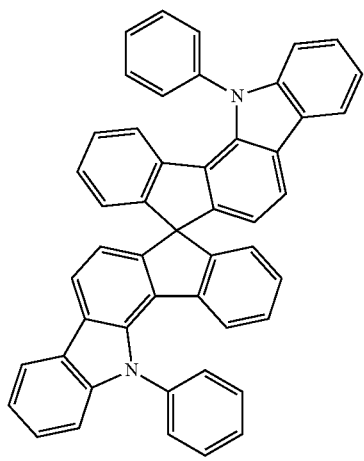 [SMILES: c1ccc(-n2c3ccccc3c3ccc4c(c32)-c2ccccc2C42c3ccccc3-c3c2ccc2c4ccccc4n(-c4ccccc4)c32)cc1]
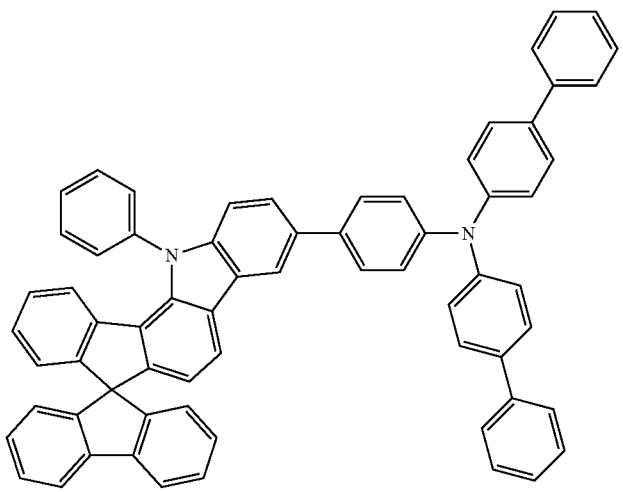 [SMILES: c1ccc(-c2ccc(N(c3ccc(-c4ccccc4)cc3)c3ccc(-c4ccc5c(c4)c4ccc6c(c4n5-c4ccccc4)-c4ccccc4C64c5ccccc5-c5ccccc54)cc3)cc2)cc1]

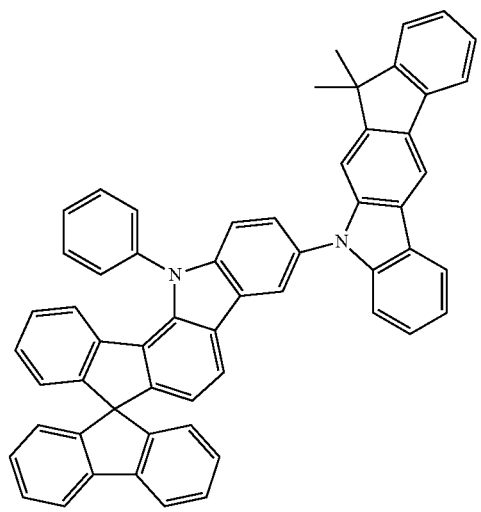 [SMILES: CC1(C)c2ccccc2-c2cc3c4ccccc4n(-c4ccc5c(c4)c4ccc6c(c4n5-c4ccccc4)-c4ccccc4C64c5ccccc5-c5ccccc54)c3cc21]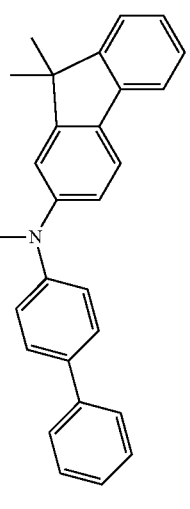

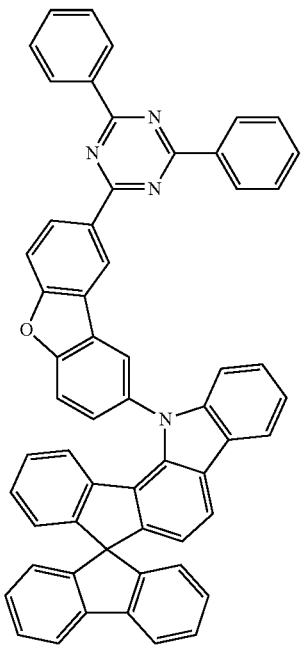 [SMILES: c1ccc(-c2nc(-c3ccccc3)nc(-c3ccc4oc5ccc(-n6c7ccccc7c7ccc8c(c76)-c6ccccc6C86c7ccccc7-c7ccccc76)cc5c4c3)n2)cc1]
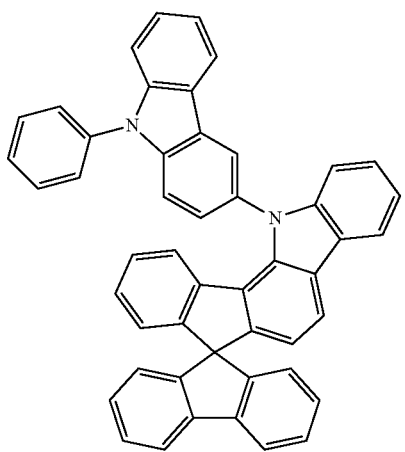 [SMILES: c1ccc(-n2c3ccccc3c3cc(-n4c5ccccc5c5ccc6c(c54)-c4ccccc4C64c5ccccc5-c5ccccc54)ccc32)cc1]

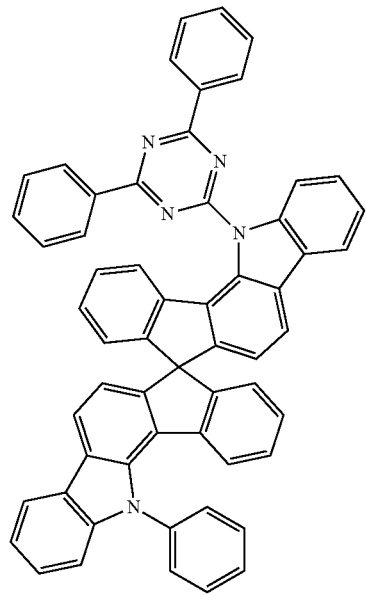 [SMILES: c1ccc(-c2nc(-c3ccccc3)nc(-n3c4ccccc4c4ccc5c(c43)-c3ccccc3C53c4ccccc4-c4c3ccc3c5ccccc5n(-c5ccccc5)c43)n2)cc1]
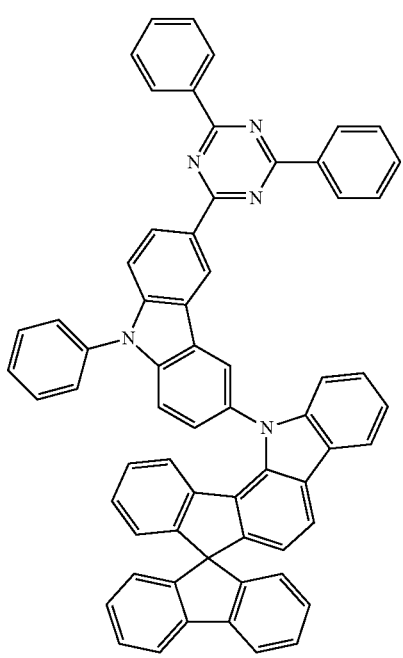 [SMILES: c1ccc(-c2nc(-c3ccccc3)nc(-c3ccc4c(c3)c3cc(-n5c6ccccc6c6ccc7c(c65)-c5ccccc5C75c6ccccc6-c6ccccc65)ccc3n4-c3ccccc3)n2)cc1]

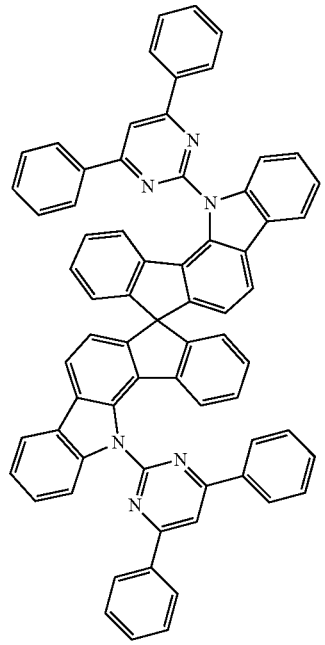 [SMILES: c1ccc(-c2cc(-c3ccccc3)nc(-n3c4ccccc4c4ccc5c(c43)-c3ccccc3C53c4ccccc4-c4c3ccc3c5ccccc5n(-c5nc(-c6ccccc6)cc(-c6ccccc6)n5)c43)n2)cc1]
The basic structure of the compounds according to the invention can be prepared by the route outlined in Scheme 1. The functionalisation can be carried out in accordance with Scheme 2.
Scheme 1:
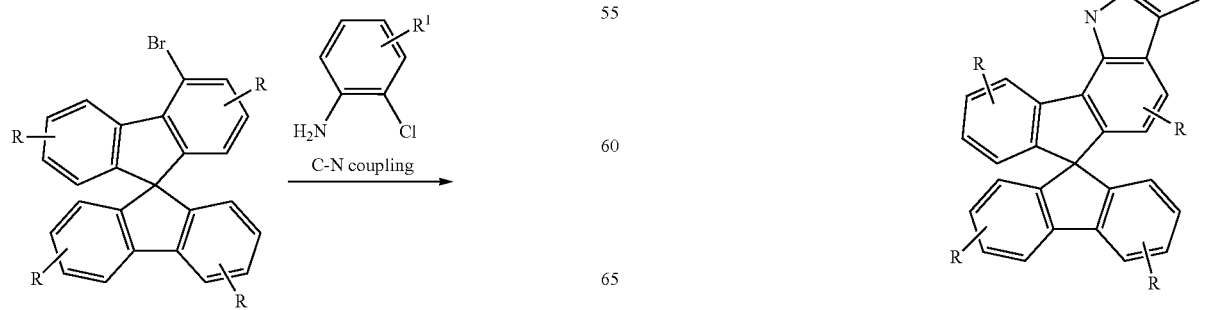
-continued
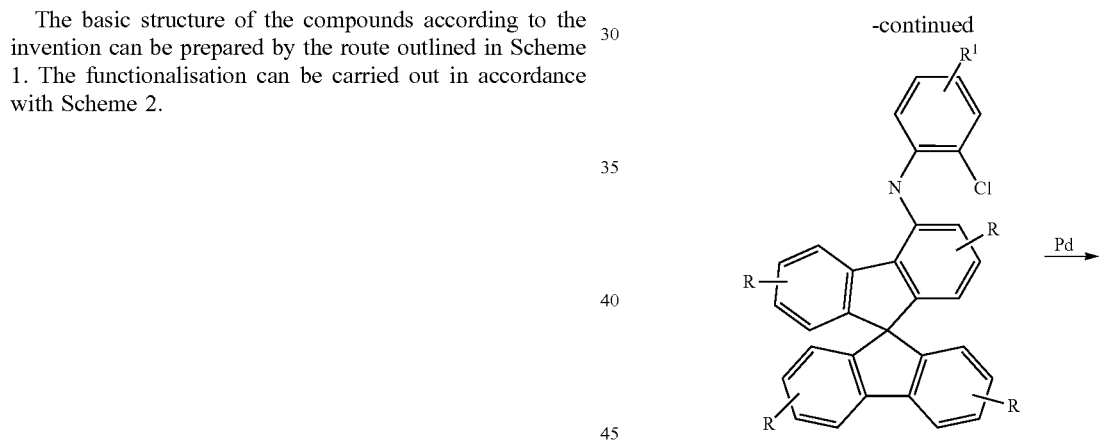

Scheme 2:
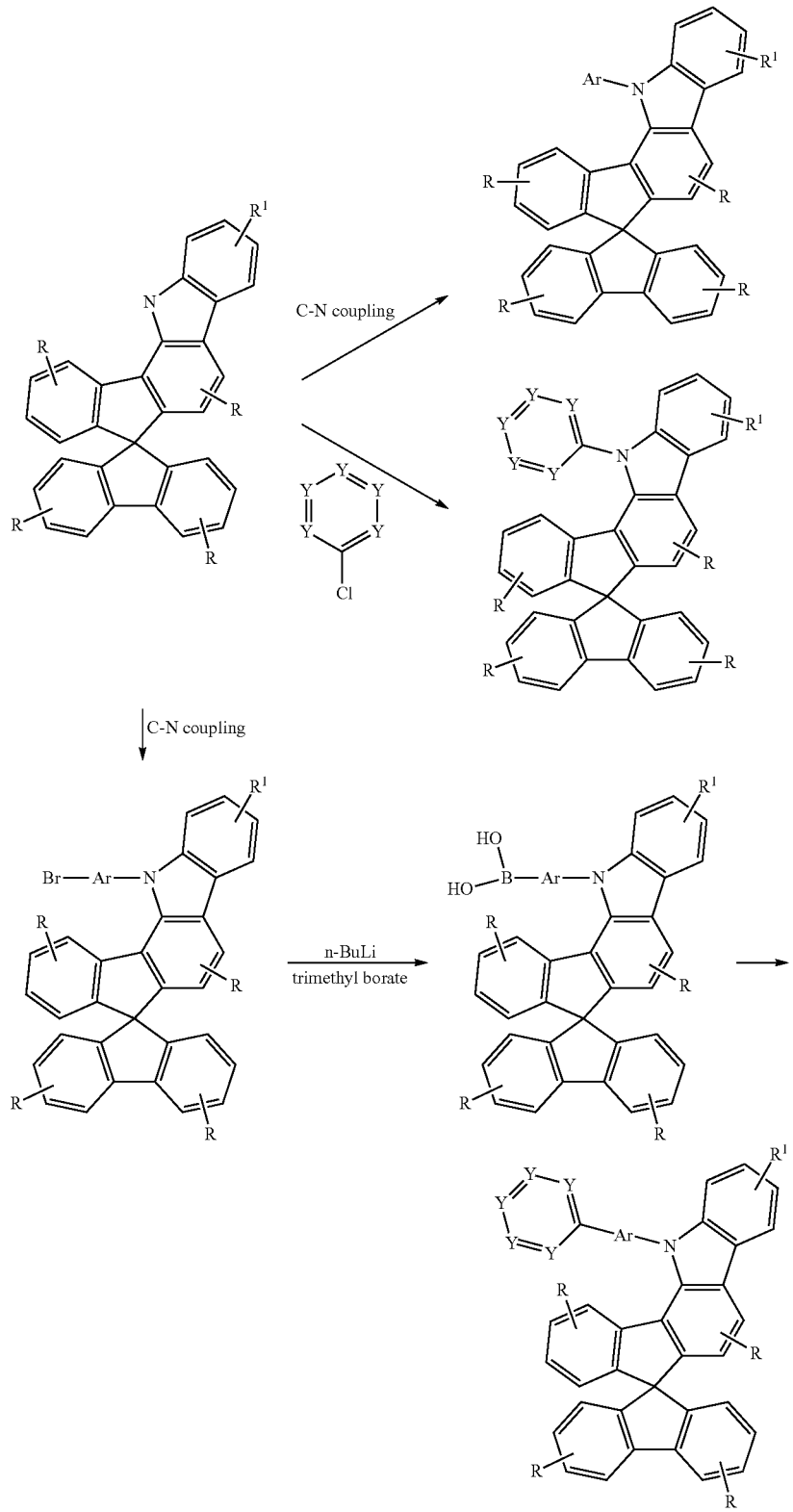
The synthesis here is usually carried out starting from literature-known 4-bromospirobifluorene (Organic Letters 2009, 11(12), 2607-2610) or a correspondingly substituted 4-bromospirobifluorene. This is reacted with an ortho-haloaminobenzene in a C—N coupling reaction, for example with Pd or Cu catalysis, where the halogen is preferably Cl, Br or I. A naphthalene, fluorene, dibenzofuran or dibenzothiophene derivative, for example, can be employed entirely analogously, giving compounds which contain groups of the formula (2) or (3). The ring closure to give the corresponding carbazole derivative is carried out by an intramolecular Pd-catalysed coupling reaction.

The synthesis of compounds of the formula (1A) can be carried out entirely analogously starting from literature-known 4,4'-dibromospirobifluorene.

Compounds of the formula (1) where n=0 and m=1 are obtained by a coupling reaction, for example Hartwig-Buchwald coupling or Ullmann coupling, with a correspondingly functionalised aromatic compound or heteroaromatic compound, where the reactive group is preferably Cl, Br or I.

Compounds of the formula (1) where n=1 and m=0 are obtained by a nucleophilic aromatic substitution reaction or by a Pd-catalysed coupling reaction with a group (Het-Ar) which is substituted by a corresponding leaving group, in particular Cl or Br.

Compounds of the formula (1) where n=1 and m=1 are obtained by a coupling reaction, for example a Hartwig-Buchwald coupling or Ullmann coupling, with a difunctionalised aromatic compound or heteroaromatic compound, where the reactive groups are preferably a bromine group and an iodine group, followed by a Pd-catalysed coupling reaction, for example a Suzuki, Negishi, Yamamoto, Grignard-Cross or Stille coupling, optionally after conversion of a halogen group into a boronic acid derivative.

The present invention furthermore relates to a process for the preparation of a compound of the formula (1) or (1A), comprising the reaction steps:
a) synthesis of the skeleton of compound (1) or (1A) which as yet contains no group (Het-Ar) and/or Ar; and
b) reaction of the skeleton from a) in a C—C coupling, such as Suzuki, Negishi, Yamamoto, Grignard-Cross or Stille coupling, etc., or C—N coupling, such as Buchwald or Ullmann coupling.

The compounds according to the invention described above, in particular compounds which are substituted by reactive leaving groups, such as bromine, iodine, chlorine, boronic acid or boronic acid ester, or by reactive, polymerisable groups, such as olefins, styrenes, acrylates or oxetanes, can be used as monomers for the generation of corresponding oligomers, dendrimers or polymers. The oligomerisation or polymerisation here preferably takes place via the halogen functionality or the boronic acid functionality or via the polymerisable group. It is furthermore possible to crosslink the polymers via groups of this type. The compounds and polymers according to the invention can be employed as crosslinked or uncrosslinked layer.

The invention therefore furthermore relates to oligomers, polymers or dendrimers containing one or more of the compounds according to the invention indicated above, where one or more bonds from the compound according to the invention to the polymer, oligomer or dendrimer are present at one or more positions instead of substituents. Depending on the linking of the compound according to the invention, this forms a side chain of the oligomer or polymer or is linked in the main chain or forms the core of a dendrimer. The polymers, oligomers or dendrimers may be conjugated, partially conjugated or non-conjugated. The oligomers or polymers may be linear, branched or dendritic. The same preferences as described above apply to the recurring units of the compounds according to the invention in oligomers, dendrimers and polymers.

For the preparation of the oligomers or polymers, the monomers according to the invention are homopolymerised or copolymerised with further monomers. Preference is given to homopolymers or copolymers in which the units of the formula (1) or the preferred embodiments indicated above are present to the extent of 0.01 to 99.9 mol %, preferably 5 to 90 mol %, particularly preferably 20 to 80 mol %. Suitable and preferred comonomers which form the polymer backbone are selected from fluorenes (for example in accordance with EP 842208 or WO 2000/22026), spirobifluorenes (for example in accordance with EP 707020, EP 894107 or WO 2006/061181), para-phenylenes (for example in accordance with WO 92/18552), carbazoles (for example in accordance with WO 2004/070772 or WO 2004/113468), thiophenes (for example in accordance with EP 1028136), dihydrophenanthrenes (for example in accordance with WO 2005/014689), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers may also contain further units, for example hole-transport units, in particular those based on triarylamines, and/or electron-transport units. In addition, the polymers may contain triplet emitters, either copolymerised or mixed in as a blend. In particular, the combination of the oligomers, polymers or dendrimers according to the invention with triplet emitters leads to particularly good results.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-di-isopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol—dimethyl ether, tetraethylene glycol dimethyl ether, 2-isopropylnaphthalene, pentylbenzene, hexylbenzene, heptylbenzene, octylbenzene, 1,1-bis(3,4-di-methylphenyl)ethane or mixtures of these solvents.

The present invention therefore furthermore relates to a formulation comprising a compound according to the invention and at least one further compound. The further compound may be, for example, a solvent, in particular one of the above-mentioned solvents or a mixture of these solvents. However, the further compound may also be at least one further organic or inorganic compound which is likewise employed in the electronic device, for example an emitting compound and/or a further matrix material. Suitable emitting compounds and further matrix materials are indicated below in connection with the organic electroluminescent device. This further compound may also be polymeric.

The compounds according to the invention are suitable for use in an electronic device, in particular in an organic electroluminescent device.

The present invention therefore furthermore relates to the use of a compound according to the invention in an electronic device, in particular in an organic electroluminescent device.

The present invention still furthermore relates to an electronic device comprising at least one compound according to the invention.

An electronic device in the sense of the present invention is a device which comprises at least one layer which comprises at least one organic compound. The component may also comprise inorganic materials or also layers which are built up entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), dye-sensitised organic solar cells (DSSCs), organic optical detectors, organic photoreceptors, organic field-quench devices (O-FQDs), light-emitting electrochemical cells (LECs), organic laser diodes (O-lasers) and "organic plasmon emitting devices", but preferably organic electroluminescent devices (OLEDs), particularly preferably phosphorescent OLEDs.

The organic electroluminescent device comprises cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. Interlayers, which have, for example, an exciton-blocking function, may likewise be introduced between two emitting layers. However, it should be pointed out that each of these layers does not necessarily have to be present. The organic electroluminescent device here may comprise one emitting layer, or it may comprise a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). The organic electroluminescent device according to the invention may also be a tandem OLED, in particular also for white-emitting OLEDs.

The compound according to the invention in accordance with the embodiments indicated above can be employed in various layers, depending on the precise structure. Preference is given to an organic electroluminescent device comprising a compound of the formula (1) or the preferred embodiments indicated above as matrix material for phosphorescent or fluorescent emitters, in particular for phosphorescent emitters, and/or in an electron-blocking or exciton-blocking layer and/or in a hole-transport layer and/or in a hole-blocking layer and/or in a hole-blocking or electron-transport layer, depending on the precise substitution.

In a preferred embodiment of the invention, the compound according to the invention is employed as matrix material for a phosphorescent compound in an emitting layer. The organic electroluminescent device here may comprise one emitting layer, or it may comprise a plurality of emitting layers, where at least one emitting layer comprises at least one compound according to the invention as matrix material.

If the compound according to the invention is employed as matrix material for a phosphorescent compound in an emitting layer, it is preferably employed in combination with one or more phosphorescent materials (triplet emitters). Phosphorescence in the sense of this invention is taken to mean the luminescence from an excited state having relatively high spin multiplicity, i.e. a spin state>1, in particular from an excited triplet state. In the sense of this application, all luminescent complexes containing transition metals or lanthanides, in particular all iridium, platinum and copper complexes, are to be regarded as phosphorescent compounds.

The mixture of the compound according to the invention and the emitting compound comprises between 99 and 1% by vol., preferably between 98 and 10% by vol., particularly preferably between 97 and 60% by vol., in particular between 95 and 80% by vol., of the compound according to the invention, based on the entire mixture comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture comprising emitter and matrix material.

A further preferred embodiment of the present invention is the use of the compound according to the invention as matrix material for a phosphorescent emitter in combination with a further matrix material. Particularly suitable matrix materials which can be employed in combination with the compounds according to the invention are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-bis-carbazolylbiphenyl) or the carbazole derivatives disclosed in WO 2005/039246, US 2005/0069729, JP 2004/288381, EP 1205527, WO 2008/086851 or WO 2013/041176, indolocarbazole derivatives, for example in accordance with WO 2007/063754 or WO 2008/056746, indenocarbazole derivatives, for example in accordance with WO 2010/136109, WO 2011/000455, WO 2013/041176 or WO 2013/056776, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2007/063754, WO 2008/056746, WO 2010/015306, WO 2011/057706, WO 2011/060859 or WO 2011/060877, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with WO 2011/042107, WO 2011/060867, WO 2011/088877 and WO 2012/143080, or triphenylene derivatives, for example in accordance with WO 2012/048781. A further phosphorescent emitter which emits at shorter wavelength than the actual emitter may likewise be present in the mixture as co-host, or a compound which does not participate in the charge transport to a significant extent, if at all, as described, for example, in WO 2010/108579.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescence emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 2001/41512, WO 2002/02714, WO 2002/15645, EP 1191613, EP 1191612, EP 1191614, WO 2005/033244, WO 2005/019373, US 2005/0258742, WO 2010/086089, WO 2011/157339, WO 2012/007086, WO 2012/163471, WO 2013/000531 and WO 2013/020631. Also suitable are, for example, the metal complexes disclosed in the unpublished applications EP 12005187.5 and EP 12005715.3. In general, all phosphorescent complexes as are used in accordance with the prior art for phosphorescent OLEDs and as are known to the person skilled in the art in the area of organic electroluminescence are suitable, and the person skilled in the art will be able to use further phosphorescent complexes without inventive step.

The compounds according to the invention are also suitable, in particular, as matrix materials for phosphorescent emitters in organic electroluminescent devices, as described, for example, in US 2011/0248247 and US 2012/0223633. In these multicoloured display components, an additional blue emission layer is applied by vapour deposition over the entire area to all pixels, also those having a colour other than blue. It has been found here, surprisingly, that the compounds according to the invention, when employed as matrix materials for the red and/or green pixels, continue to result in very good emission together with the vapour-deposited blue emission layer.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is the same as or similar to the metal complex in the emitting layer as hole-transport or hole-injection material directly adjacent to the emitting layer, as described, for example, in WO 2009/030981.

In a further embodiment of the invention, the compound according to the invention is employed in a hole-transport layer or in an electron-blocking layer or exciton-blocking layer.

In still a further preferred embodiment of the invention, the compound according to the invention is employed as electron-transport material in an electron-transport or electron-injection layer. The emitting layer here may be fluorescent or phosphorescent. If the compound is employed as electron-transport material, it may be preferred for it to be doped, for example with alkali-metal complexes, such as, for example, LiQ (lithium hydroxy-quinolinate).

In still a further preferred embodiment of the invention, the compound according to the invention is employed in a hole-blocking layer. A hole-blocking layer is taken to mean a layer which is directly adjacent to an emitting layer on the cathode side.

In the further layers of the organic electroluminescent device according to the invention, all materials can be used as are usually employed in accordance with the prior art. The person skilled in the art will therefore be able to employ all materials which are known for organic electroluminescent devices in combination with the compounds of the formula (1) according to the invention or the preferred embodiments indicated above without inventive step.

Preference is furthermore given to an organic electroluminescent device, characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), ink-jet printing or nozzle printing. Soluble compounds, which are obtained, for example, by suitable substitution, are necessary for this purpose.

Also possible are hybrid processes, in which, for example, one or more layers are applied from solution and one or more further layers are applied by vapour deposition.

These processes are generally known to the person skilled in the art and can be applied by him without inventive step to organic electroluminescent devices comprising the compounds according to the invention.

The compounds according to the invention and the organic electroluminescent devices according to the invention are distinguished by one or more of the following surprising advantages over the prior art:

1. The compounds according to the invention, employed as matrix material for fluorescent or phosphorescent emitters, result in long lifetimes. This applies, in particular, if the compounds are employed as matrix material for a phosphorescent emitter.

2. The compounds according to the invention result in very low operating voltages. This applies, in particular, if the compounds are employed as matrix material for a phosphorescent emitter.

These above-mentioned advantages are not accompanied by an impairment in the other electronic properties.

The invention is explained in greater detail by the following examples without wishing to restrict it thereby. The person skilled in the art will be able to use the descriptions to carry out the invention throughout the range disclosed and prepare further compounds according to the invention without inventive step and use them in electronic devices or apply the process according to the invention.

EXAMPLES

The following syntheses are carried out, unless indicated otherwise, under a protective-gas atmosphere in dried solvents. The solvents and reagents can be purchased from ALDRICH or ABCR. The numbers indicated in the case of the starting materials which are not commercially available are the corresponding CAS numbers.

SYNTHESIS EXAMPLES

Example 1a: Synthesis of (2-chlorophenyl)-4-spiro-9,9'-bifluorenyl-amine

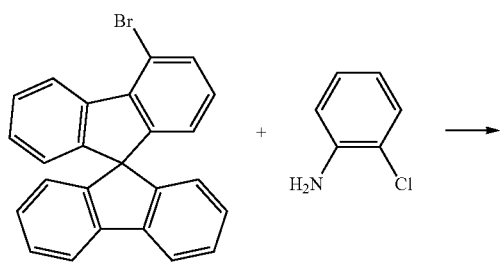

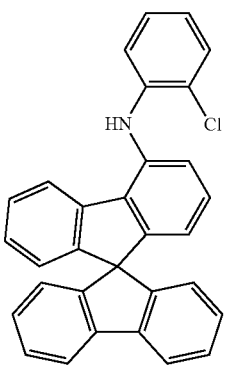

54 g (137 mmol) of 4-bromospiro-9,9'-bifluorene (1161009-88-6), 17.9 g (140 mmol) of 2-chloroaniline, 68.2 g (710 mmol) of sodium tert-butoxide, 613 mg (3 mmol) of palladium(II) acetate and 3.03 g (5 mmol) of dppf are dissolved in 1.3 l of toluene and stirred under reflux for 5 h. The reaction mixture is cooled to room temperature, extended with toluene and filtered through Celite. The filtrate is evaporated in vacuo, and the residue is crystallised from toluene/heptane. The product is isolated as a colourless solid. Yield: 52.2 g (118 mmol), 86% of theory.

The following compounds are prepared analogously:

| | Starting material 1 | Starting material 2 | Product | Yield |
|---|---|---|---|---|
| 1b |  | 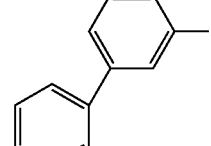 7285-66-7 | 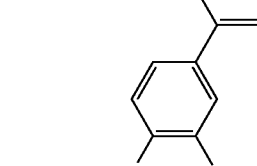 | 83% |
| 1c |  |  858426-71-8 | 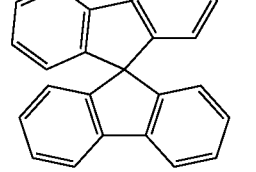 | 78% |

-continued
| | Starting material 1 | Starting material 2 | Product | Yield |
|---|---|---|---|---|
| 1d | 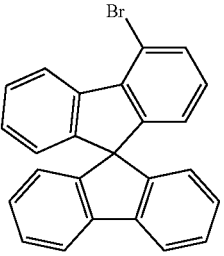 [SMILES: Brc1cccc2c1-c1ccccc1C21c2ccccc2-c2ccccc21] | 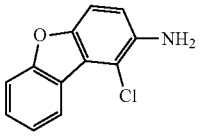<br>133617-97-7 | 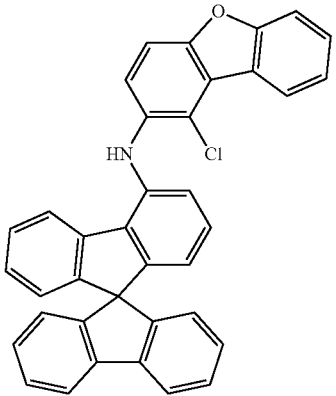 [SMILES: Clc1c(Nc2cccc3c2-c2ccccc2C32c3ccccc3-c3ccccc32)ccc2oc3ccccc3c12] | 67% |
| 1e | 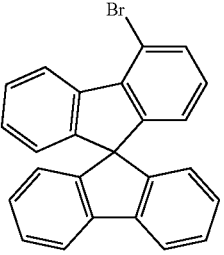 [SMILES: Brc1cccc2c1-c1ccccc1C21c2ccccc2-c2ccccc21] | 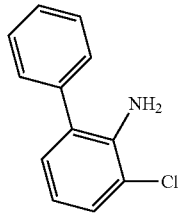<br>76838-82-9 | 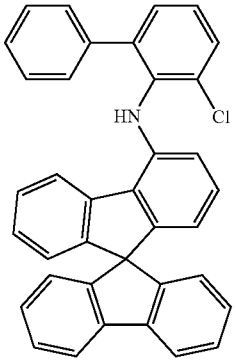 [SMILES: Clc1cccc(-c2ccccc2)c1Nc1cccc2c1-c1ccccc1C21c2ccccc2-c2ccccc21] | 53% |
| 1f | 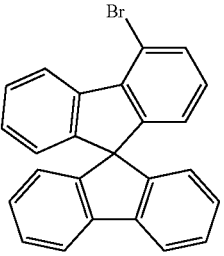 [SMILES: Brc1cccc2c1-c1ccccc1C21c2ccccc2-c2ccccc21] | 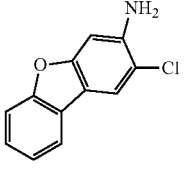<br>5833-88-5 | 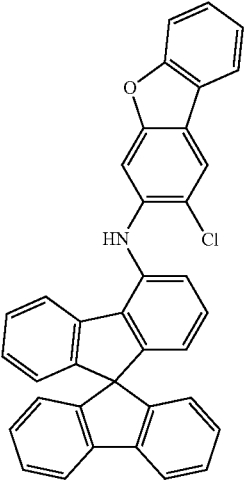 [SMILES: Clc1cc2c(cc1Nc1cccc3c1-c1ccccc1C31c3ccccc3-c3ccccc31)oc1ccccc12] | 73% |

-continued
| | Starting material 1 | Starting material 2 | Product | Yield |
|---|---|---|---|---|
| 1g | 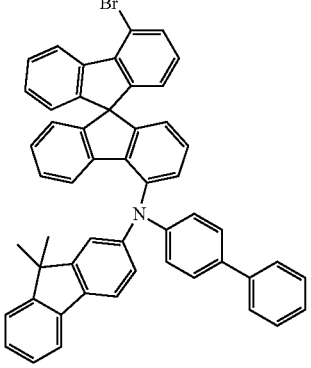<br>see Example 11 | 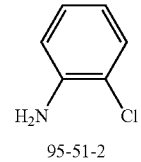<br>95-51-2 | 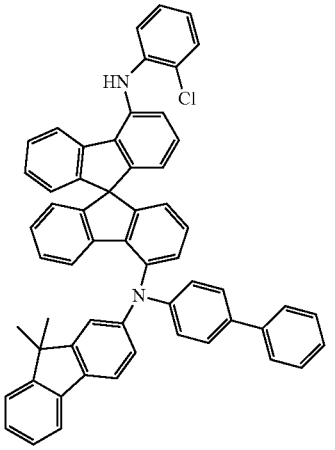 [SMILES: CC1(C)c2ccccc2-c2ccc(N(c3ccc(-c4ccccc4)cc3)c3cccc4c3-c3ccccc3C43c4ccccc4-c4c(Nc5ccccc5Cl)cccc43)cc21] | 68% |
| 1h |  | 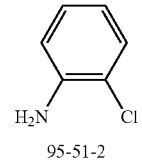<br>95-51-2 | 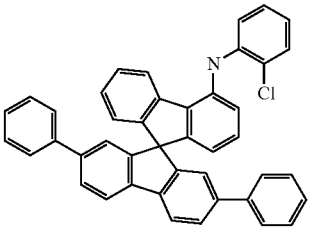 [SMILES: Clc1ccccc1Nc1cccc2c1-c1ccccc1C21c2cc(-c3ccccc3)ccc2-c2ccc(-c3ccccc3)cc21] | 70% |
| 1i | 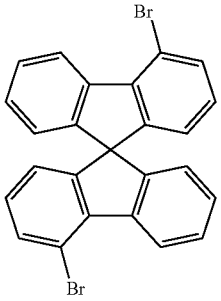 [SMILES: Brc1cccc2c1-c1ccccc1C21c2ccccc2-c2c(Br)cccc21] | 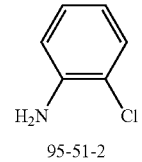<br>95-51-2 | 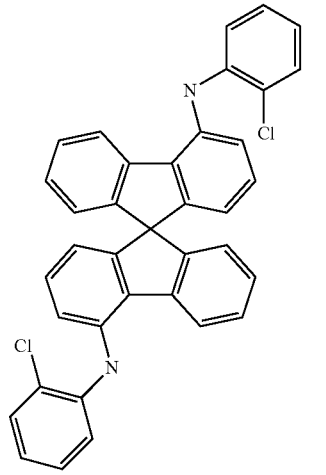 [SMILES: Clc1ccccc1Nc1cccc2c1-c1ccccc1C21c2ccccc2-c2c(Nc3ccccc3Cl)cccc21] | 72% |
| 1j | 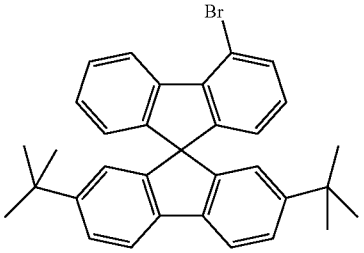 [SMILES: CC(C)(C)c1ccc2c(c1)C1(c3cc(C(C)(C)C)ccc3-2)c2ccccc2-c2c(Br)cccc21] | 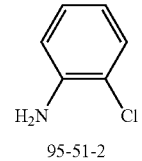<br>95-51-2 | 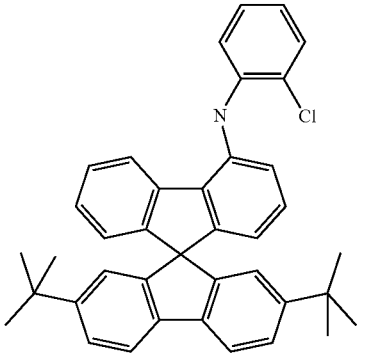 [SMILES: CC(C)(C)c1ccc2c(c1)C1(c3cc(C(C)(C)C)ccc3-2)c2ccccc2-c2c(Nc3ccccc3Cl)cccc21] | 71% |

-continued

| | Starting material 1 | Starting material 2 | Product | Yield |
|---|---|---|---|---|
| 1k | (4-bromo-9,9'-spirobifluorene) | (4-tert-butyl-2-chloroaniline) 42265-67-8 | | 69% |
| 1l | (4-bromo-2'-phenyl-9,9'-spirobifluorene) | (2-chloroaniline) 95-51-2 | | 73% |
| 1m | (4-bromo-9,9-dimethylfluorene) 942615-32-9 | (2-chloroaniline) 95-51-2 | | 78% |
| 1n | (4-bromo-9,9-diphenylfluorene) 713125-22-5 | (2-chloroaniline) 95-51-2 | | 83% |

Example 2a: Synthesis of spiro[9H-fluoren-9,7'(1'H)-indeno[1,2-a]-carbazole]

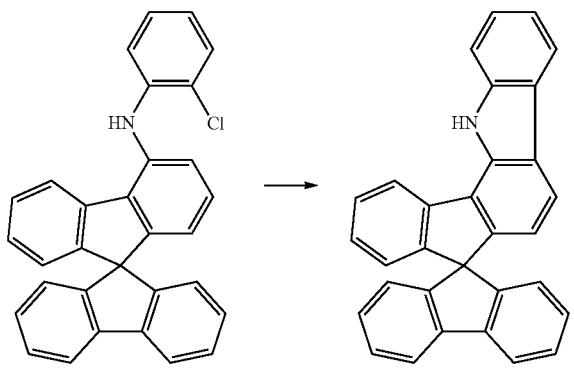 [SMILES: Clc1ccccc1Nc1cccc2c1-c1ccccc1C21c2ccccc2-c2ccccc21 ; c1ccc2c(c1)-c1ccccc1C21c2ccccc2-c2c1ccc1c2[nH]c2ccccc21]

45 g (102 mmol) of (2-chlorophenyl)-4-spiro-9,9'-bifluorenylamine, 56 g (409 mmol) of potassium carbonate, 4.5 g (12 mmol) of tricyclohexylphosphonium—tetrafluoroborate and 1.38 g (6 mmol) of palladium(II) acetate are suspended in 500 ml of dimethylacetamide and stirred under reflux for 6 h. After cooling, the reaction mixture is extended with 300 ml of water and 600 ml of dichloromethane. The mixture is stirred for a further 30 min., the organic phase is separated off, filtered through a short Celite bed, and the solvent is then removed in vacuo. The crude product is extracted with hot toluene and recrystallised from toluene. The product is isolated as a beige solid (32.5 g, 80 mmol, corresponding to 78% of theory).

The following compounds are prepared analogously:

| | Starting material | Product | Yield |
|---|---|---|---|
| 2b | | | 72% |
| 2c | | | 73% |

| Starting material | Product | Yield |
|---|---|---|
| 2d | | 67% |
| 2e | | 56% |
| 2f | | 71% |

| Starting material | Product | Yield |
|---|---|---|
| 2g | | 67% |
| 2h | | 74% |
| 2i | | 68% |

| Starting material | Product | Yield |
|---|---|---|
| 2j 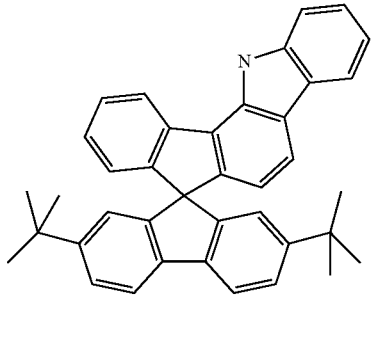 [SMILES: CC(C)(C)c1ccc2c(c1)C1(c3cc(C(C)(C)C)ccc3-2)c2ccccc2-c2c1ccc1c2[nH]c2ccccc21] | 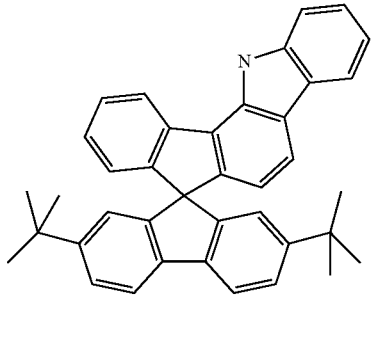 [SMILES: CC(C)(C)c1ccc2c(c1)C1(c3cc(C(C)(C)C)ccc3-2)c2ccccc2-c2c1ccc1c2[nH]c2ccccc21] | 72% |
| 2k | | 75% |
| 2l | | 73% |
| 2m | | 83% |
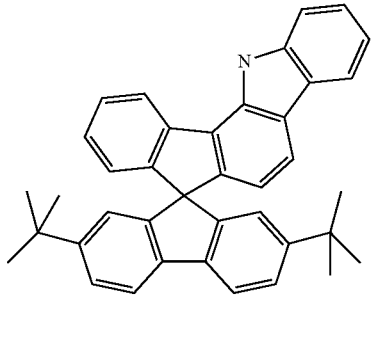 [SMILES: CC(C)(C)c1ccc2c(c1)C1(c3cc(C(C)(C)C)ccc3-2)c2ccccc2-c2c1ccc1c2[nH]c2ccccc21]

| Starting material | Product | Yield |
|---|---|---|
| 2n 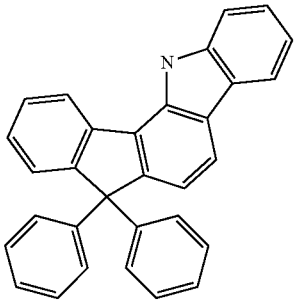 [SMILES: c1ccc(C2(c3ccccc3)c3ccccc3-c3c2ccc2c3[nH]c3ccccc32)cc1] | | 85% |

Example 3a: Synthesis of spiro[9H-fluoren-9,7'(12'H)-indeno[1,2-a]-carbazole]-12'-[2-(4,6-diphenyl-1,3,5-triazin-2-yl)]

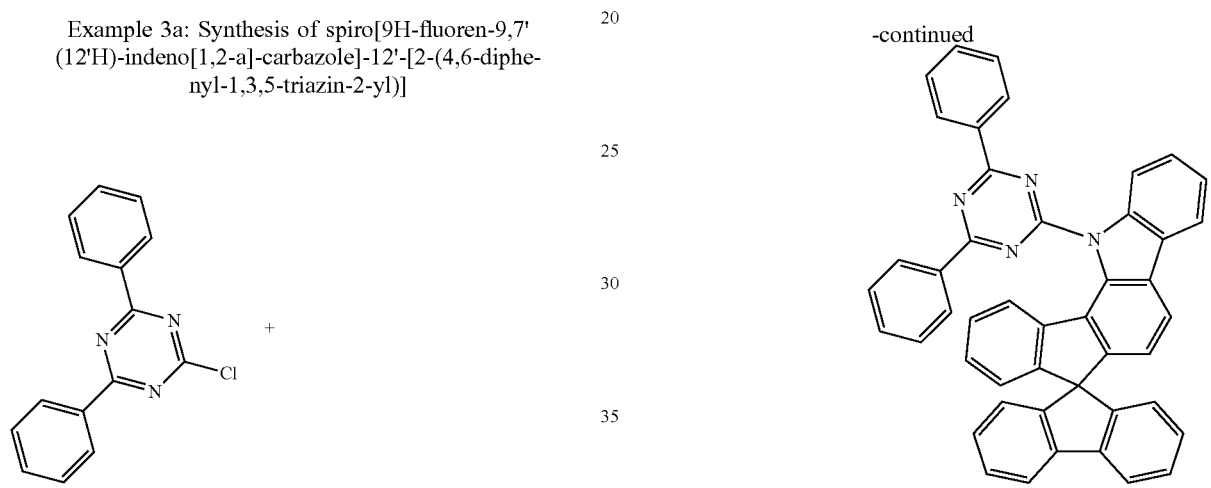

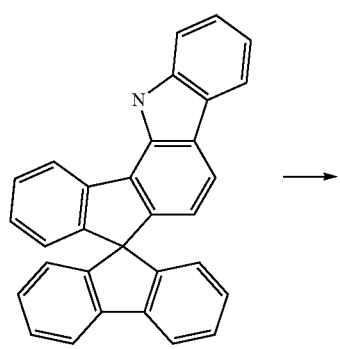

4.2 g of 60% NaH in mineral oil (0.106 mol) are dissolved in 300 ml of dimethylformamide under a protective atmosphere. 43 g (0.106 mol) of spiro[9H-fluoren-9,7'(1'H)-indeno[1,2-a]carbazole] are dissolved in 250 ml of DMF and added dropwise to the reaction mixture. After 1 h at room temperature, a solution of 2-chloro-4,6-diphenyl-1,3,5-triazine (34.5 g, 0.122 mol) in 200 ml of THF is added dropwise. The reaction mixture is then stirred at room temperature for 12 h. After this time, the reaction mixture is poured onto ice. The precipitated solid in the process is filtered off after warming to room temperature and washed with ethanol and heptane. The residue is extracted with hot toluene, recrystallised from toluene/n-heptane and finally sublimed in a high vacuum. The purity is 99.9%. The yield is 28.4 g (44.5 mmol; 42%).

The following compounds are prepared analogously:

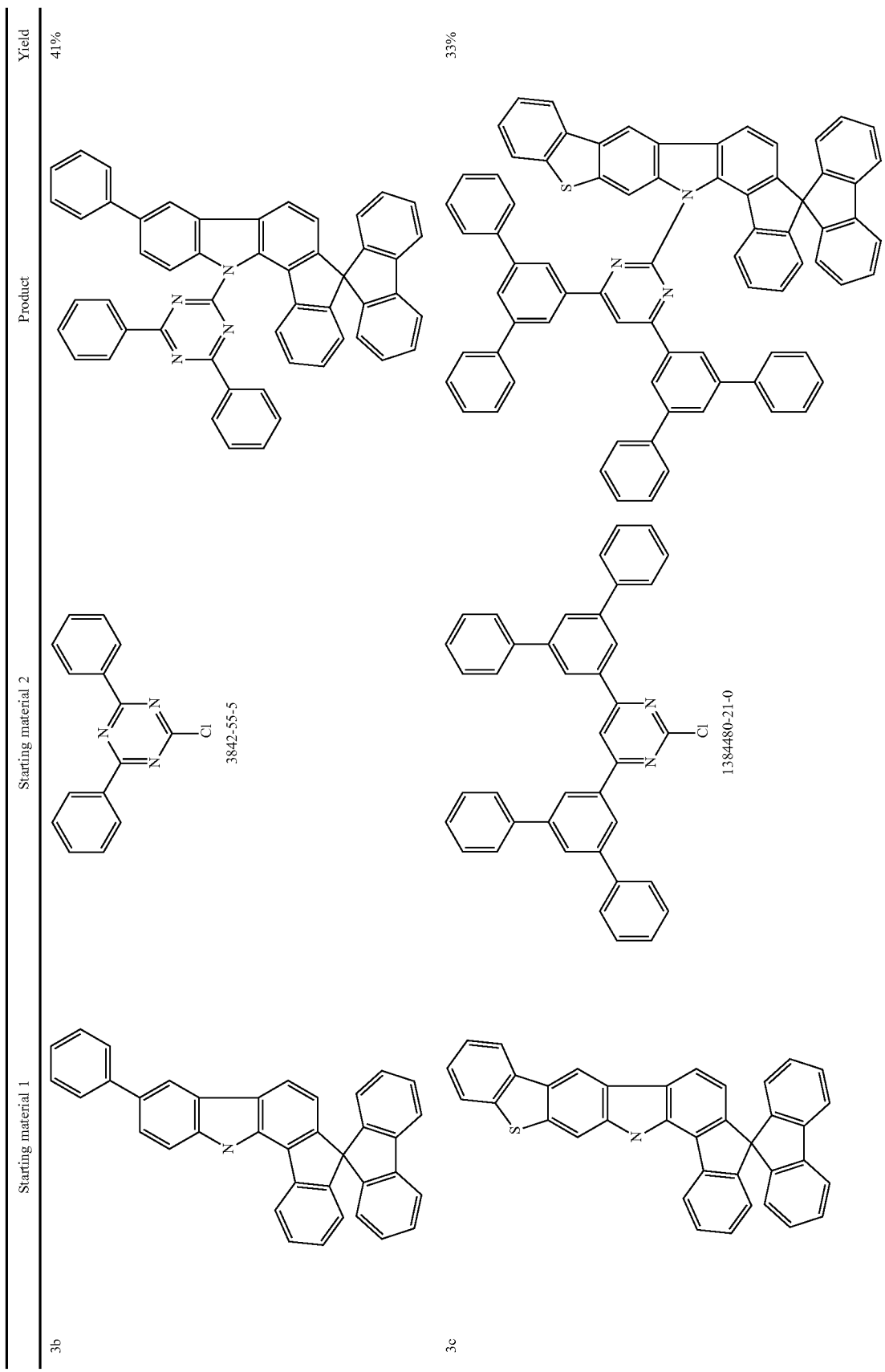

| | Starting material 1 | Starting material 2 | Product | Yield |
|---|---|---|---|---|
| 3d | (structure) | (structure) 70484-36-5 | (structure) | 42% |
| 3e | (structure) | (structure) 92853-85-5 | (structure) | 27% |

-continued
| | Starting material 1 | Starting material 2 | Product | Yield |
|---|---|---|---|---|
| 3f | 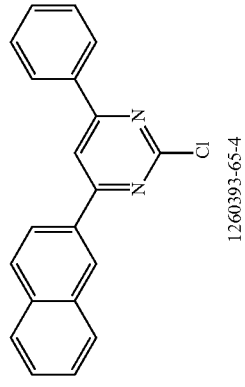 | 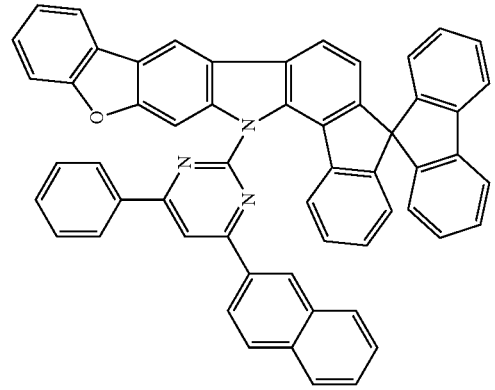 1260393-65-4 | 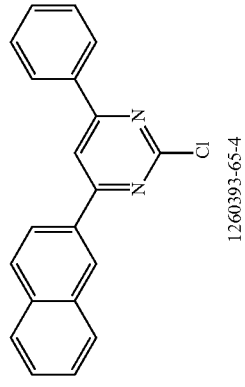 | 40% |
| 3g | 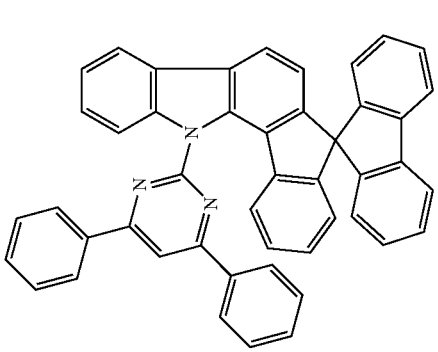 | 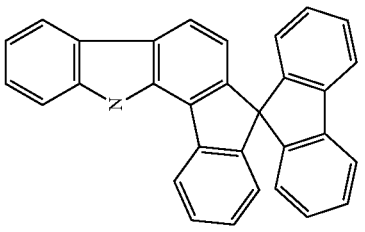 2915-16-4 | | 45% |

| Starting material 1 | Starting material 2 | Product | Yield |
|---|---|---|---|
| 3h | 133785-60-1 | | 38% |

| Starting material 1 | Starting material 2 | Product | Yield |
|---|---|---|---|
| 3i | 3842-55-5 | | 34% |

-continued
| | Starting material 1 | Starting material 2 | Product | Yield |
|---|---|---|---|---|
| 3j | 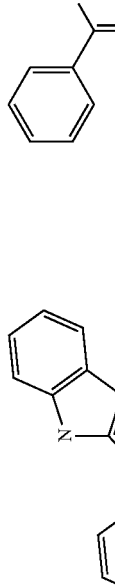 | 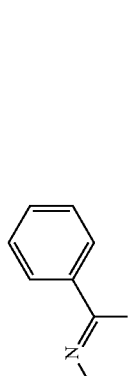 3842-55-5 | 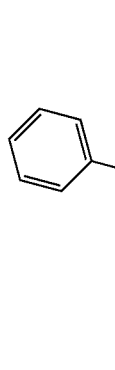 | 38% |

| Starting material 1 | Starting material 2 | Product | Yield |
|---|---|---|---|
| 3k | 3842-55-5 | | 32% |

| Starting material 1 | Starting material 2 | Product | Yield |
|---|---|---|---|
| 31 | 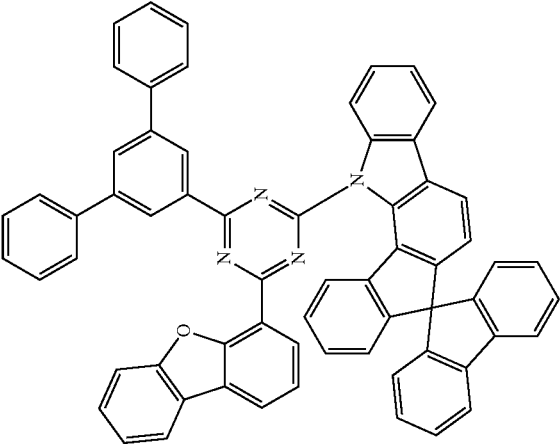 | 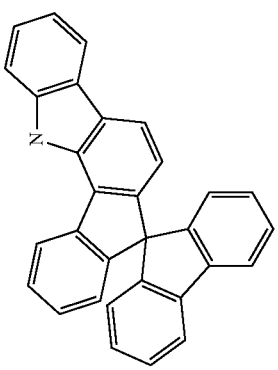 | 34% |

-continued

| Starting material 1 | Starting material 2 | Product | Yield |
|---|---|---|---|
| 3m | | | 41% |
| 3n | | | 42% |

-continued
| Starting material 1 | Starting material 2 | Product | Yield |
|---|---|---|---|
| 3o 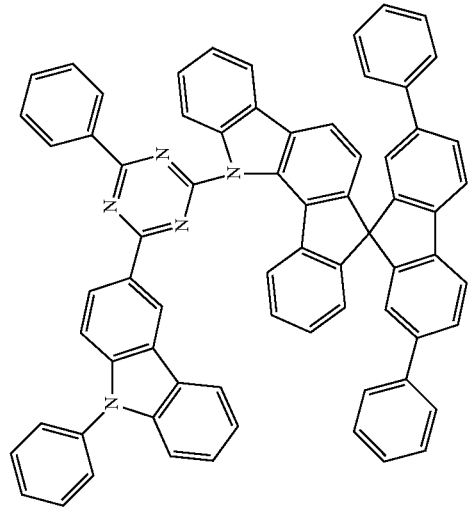 | 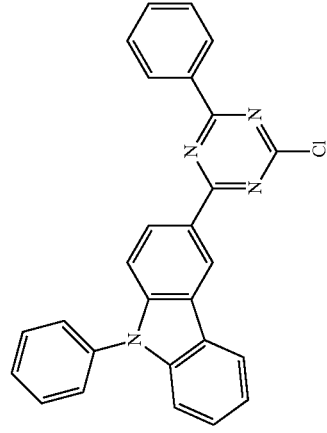 | 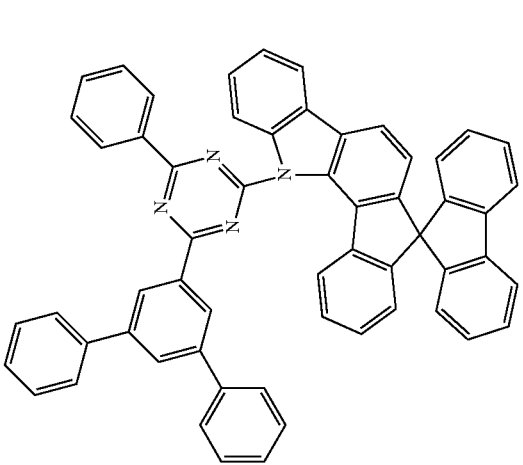 | 39% |
| 3p 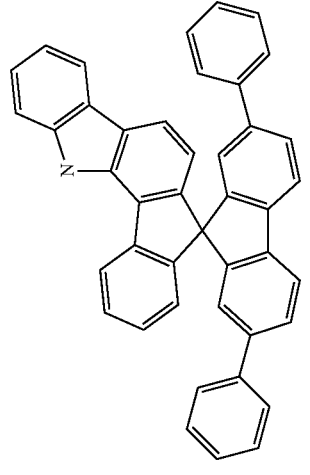 | | | 41% |

| Starting material 1 | Starting material 2 | Product | Yield |
|---|---|---|---|
| 3q | | | 36% |
| 3r cmp. | 3842-55-5 | | 40% |

| Starting material 1 | Starting material 2 | Product | Yield |
| --- | --- | --- | --- |
| 3s cmp. | 3842-55-5 | | 46% |

Example 4a: Synthesis of spiro[9H-fluoren-9,7'(12'H)-indeno[1,2-a]-carbazole]-12'-[4-bromophenyl]

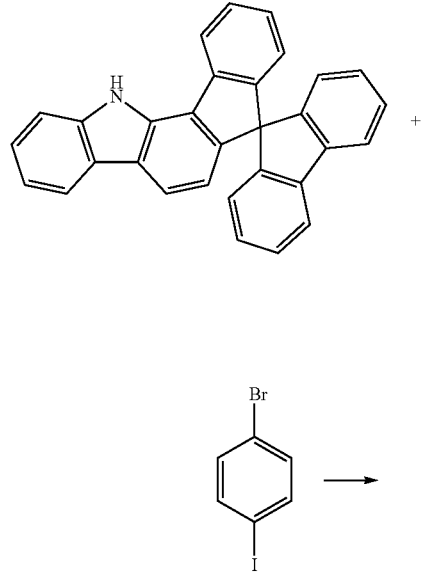

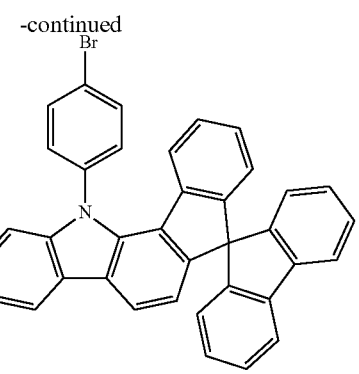

32.8 g (81 mmol) of spiro[9H-fluoren-9,7'(1'H)-indeno[1,2-a]carbazole], 115 g (406 mmol) of 1-bromo-4-iodobenzene, 22.4 g (162 mmol) of potassium carbonate, 1.84 g (8.1 mmol) of 1,3-di(2-pyridyl)-1,3-propanedione, 1.55 g (8.1 mmol) of copper iodide and 1000 ml of DMF are heated under reflux for 30 h. The reaction mixture is subsequently evaporated to dryness in a rotary evaporator. The residue is dissolved in THF and filtered through a short silica-gel bed, the solvent is then removed in vacuo. The solid is subsequently recrystallised from heptane/THF and extracted with hot heptane/toluene over aluminium oxide. The solid which has precipitated out on cooling is filtered off and dried. Yield: 37 g (66 mmol), 81%.

The following compounds are prepared analogously:

| | Starting material 1 | Starting material 2 | Product | Yield |
|---|---|---|---|---|
| 4b | | 583-55-1 | | 47% |
| 4c | | 39655-12-4 | | 27% |

-continued
| | Starting material 1 | Starting material 2 | Product | Yield |
|---|---|---|---|---|
| 4d | 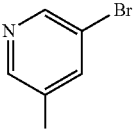 | 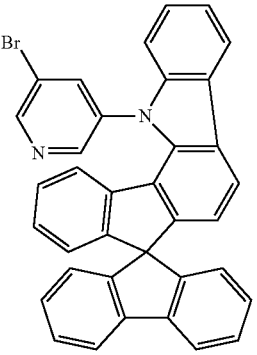 [SMILES: Brc1cncc(-n2c3ccccc3c3ccc4c(c32)-c2ccccc2C42c3ccccc3-c3ccccc32)c1] 233770-01-9 | 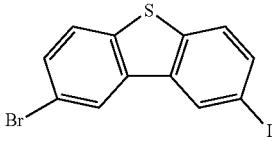 | 76% |
| 4e | 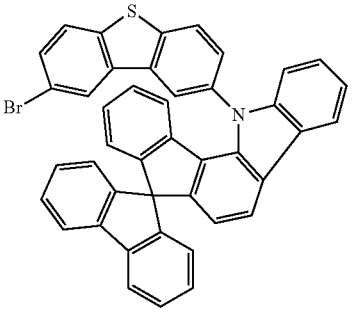 [SMILES: Brc1ccc2sc3ccc(-n4c5ccccc5c5ccc6c(c54)-c4ccccc4C64c5ccccc5-c5ccccc54)cc3c2c1] | 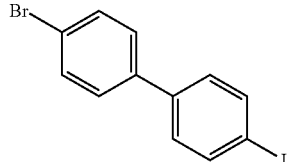 1206544-88-8 | 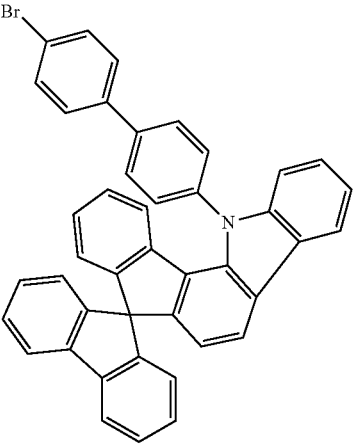 [SMILES: Brc1ccc(-c2ccc(-n3c4ccccc4c4ccc5c(c43)-c3ccccc3C53c4ccccc4-c4ccccc43)cc2)cc1] | 65% |
| 4f | 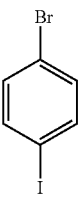 | 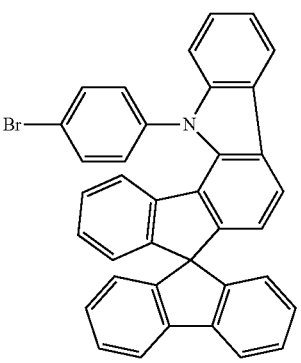 [SMILES: Brc1ccc(-n2c3ccccc3c3ccc4c(c32)-c2ccccc2C42c3ccccc3-c3ccccc32)cc1] 105946-82-5 | | 73% |
| 4g | | | | 76% |

-continued
| | Starting material 1 | Starting material 2 | Product | Yield |
|---|---|---|---|---|
| 4h | 86-74-8 | 105946-82-5 | | 81% |
| 4i | 1257220-47-5 | 591-18-4 | | 77% |
Example 5a: Synthesis of spiro[9H-fluoren-9,7'(12'H)-indeno[1,2-a]-carbazole]-12'-[(4-phenylboronic acid]
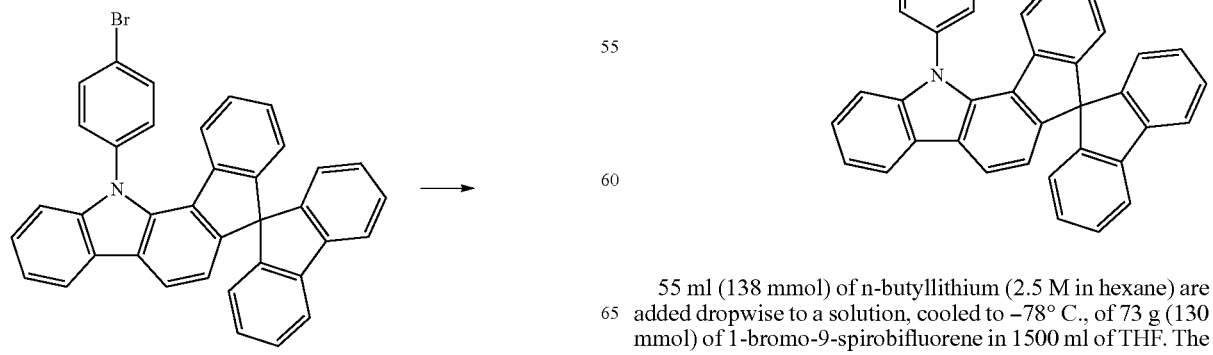
55 ml (138 mmol) of n-butyllithium (2.5 M in hexane) are added dropwise to a solution, cooled to −78° C., of 73 g (130 mmol) of 1-bromo-9-spirobifluorene in 1500 ml of THF. The reaction mixture is stirred at −78° C. for 30 min. The mixture is allowed to come to room temperature, re-cooled to −78° C., and a mixture of 20 ml (176 mmol) of trimethyl borate in 50 ml of THF is then added rapidly. After warming to −10° C., the mixture is hydrolysed using 135 ml of 2 N hydrochloric acid. The organic phase is separated off, washed with water, dried over sodium sulfate and evaporated to dryness. The residue is taken up in 300 ml of n-heptane, the colourless solid is filtered off with suction, washed with n-heptane and dried in vacuo. Yield: 94.5 g (255 mmol), 99% of theory; purity: 99% according to HPLC.

The following compounds are prepared analogously:

| Starting material | Product | Yield |
|---|---|---|
| 5b | | 88% |
| 5c | | 91% |
| 5d | | 95% |

-continued

| Starting material | Product | Yield |
|---|---|---|
| 5e | | 87% |
| 5f | | 73% |
| 5g | | 78% |
| 5h | | 77% |

Example 6a

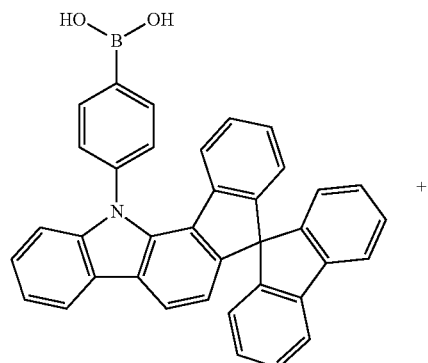

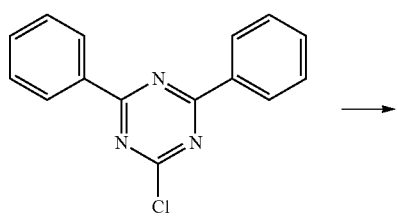

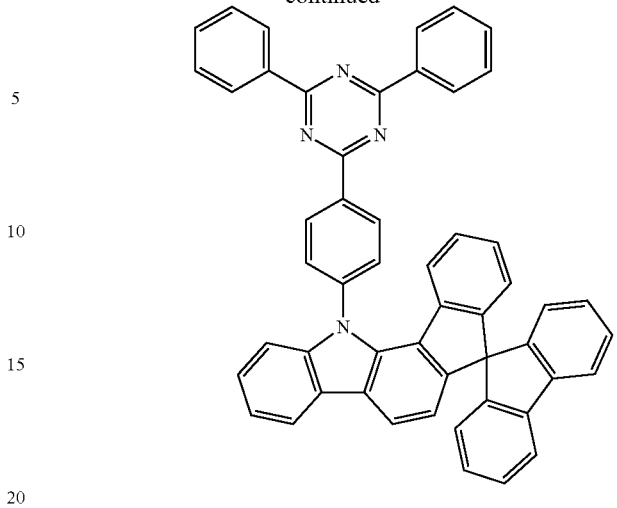

57.8 g (110 mmol) of spiro[9H-fluoren-9,7'(12'H)-indeno[1,2-a]carbazole]-12'-[4-phenylboronic acid], 29.5 g (110.0 mmol) of 2-chloro-4,6-diphenyl-1,3,5-triazine and 44.6 g (210.0 mmol) of tripotassium phosphate are suspended in 500 ml of toluene, 500 ml of dioxane and 500 ml of water. 913 mg (3.0 mmol) of tri-o-tolylphosphine and then 112 mg (0.5 mmol) of palladium(II) acetate are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene/heptane and finally sublimed in a high vacuum ($p=5\times10^{-5}$ mbar, T=377° C.). The yield is 29.2 g (41 mmol), corresponding to 37% of theory.

The following compounds are prepared analogously:

| | Starting material 1 | Starting material 2 | Product | Yield |
|---|---|---|---|---|
| 6b | | 3842-55-5 | | 22% |

-continued
| | Starting material 1 | Starting material 2 | Product | Yield |
|---|---|---|---|---|
| 6c | | 2915-16-4 | | 27% |
| 6d | | 133785-60-1 | | 35% |
| 6e | | 40734-4-5 | | 32% |
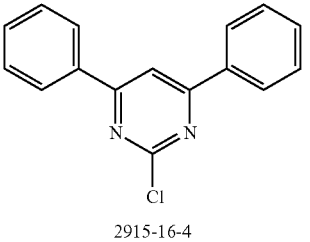 [SMILES: Clc1nc(-c2ccccc2)cc(-c2ccccc2)n1]
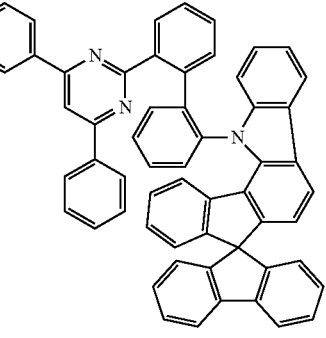
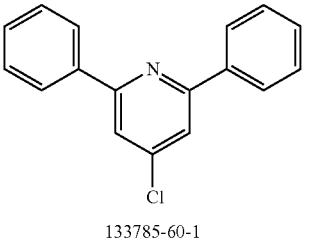 [SMILES: Clc1cc(-c2ccccc2)nc(-c2ccccc2)c1]
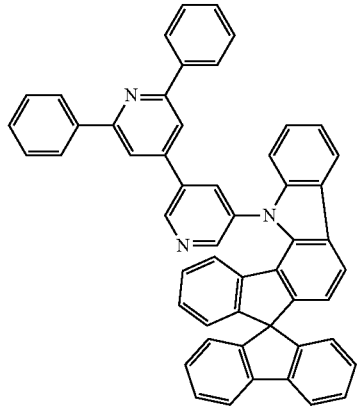 [SMILES: c1ccc(-c2cc(-c3cncc(-n4c5ccccc5c5ccc6c(c54)-c4ccccc4C64c5ccccc5-c5ccccc54)c3)cc(-c3ccccc3)n2)cc1]
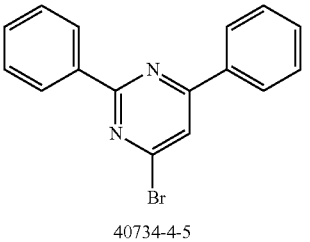 [SMILES: Brc1cc(-c2ccccc2)nc(-c2ccccc2)n1]
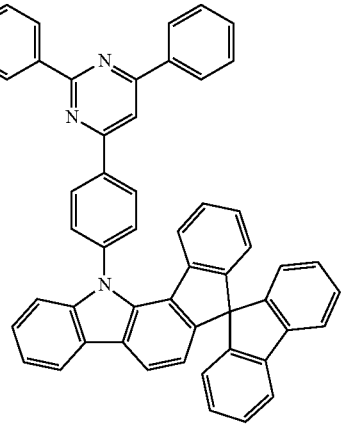

| | Starting material 1 | Starting material 2 | Product | Yield |
|---|---|---|---|---|
| 6f | | 92853-85-5 | | 33% |
| 6g | | 3842-55-5 | | 34% |
| 6h | | 108-86-1 | | 37% |

| | Starting material 1 | Starting material 2 | Product | Yield |
|---|---|---|---|---|
| 6i | 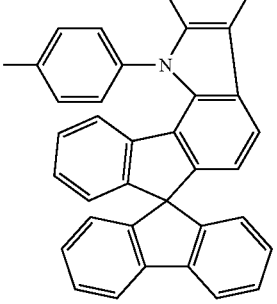 | 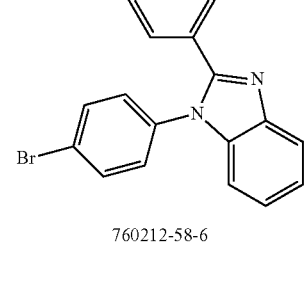 760212-58-6 | 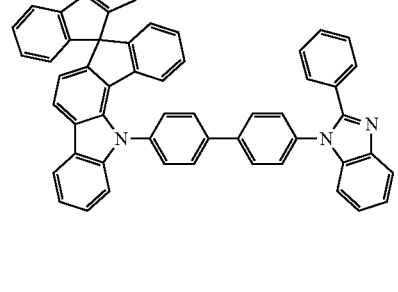 | 34% |
| 6j | 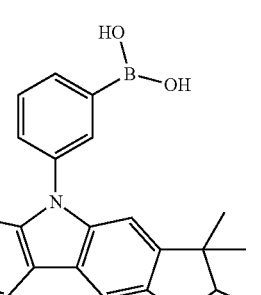 | 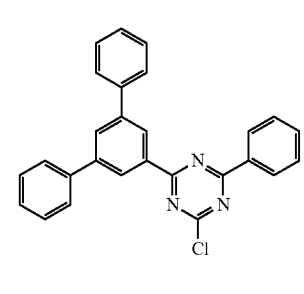 [SMILES: Clc1nc(-c2ccccc2)nc(-c2cc(-c3ccccc3)cc(-c3ccccc3)c2)n1] | 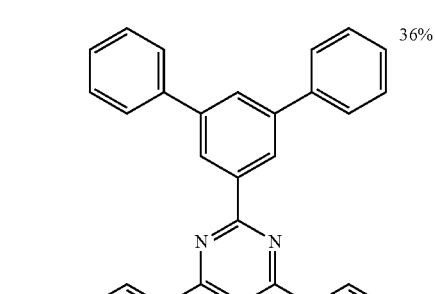 | 36% |
Example 7a
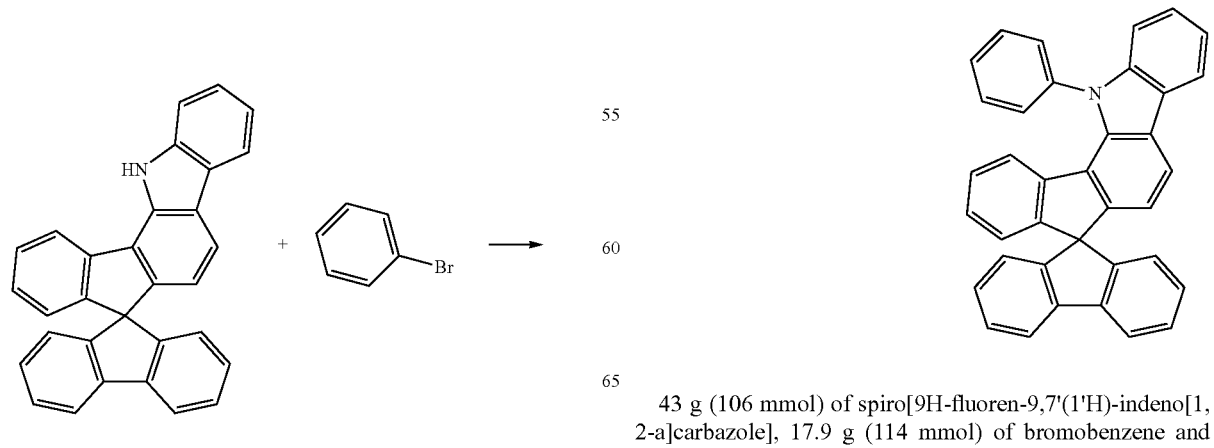
43 g (106 mmol) of spiro[9H-fluoren-9,7'(1'H)-indeno[1,2-a]carbazole], 17.9 g (114 mmol) of bromobenzene and 30.5 g of NaOtBu are suspended in 1.5 l of p-xylene. 0.5 g (2.11 mmol) of Pd(OAc)₂ and 4.2 ml of a 1M tri-tert-butylphosphine solution in toluene are added to this suspension. The reaction mixture is heated under reflux for 16 h. After cooling, the organic phase is separated off, washed three times with 200 ml of water each time and subsequently evaporated to dryness. The residue is extracted with hot toluene, recrystallised from toluene and finally sublimed in a high vacuum. The purity is 99.9% with a yield of 21.4 g (44.5 mmol; 42%).

The following compounds are prepared analogously:

| | Starting material 1 | Starting material 2 | Product | Yield |
|---|---|---|---|---|
| 7b | | 92-66-0 | | 41% |
| 7c | | 103068-20-8 | | 27% |
| 7d | | 28320-31-2 | | 29% |
| 7e | | 955959-84-9 | | 54% |

-continued
| | Starting material 1 | Starting material 2 | Product | Yield |
|---|---|---|---|---|
| 7f | 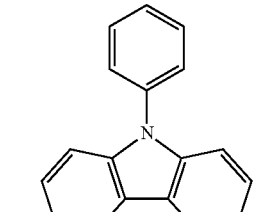 | 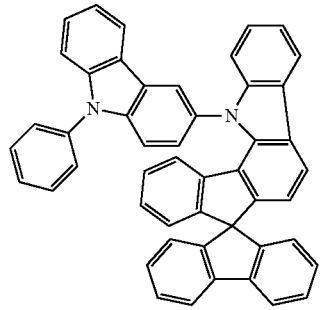 [SMILES: c1ccc(-n2c3ccccc3c3cc(-n4c5ccccc5c5ccc6c(c54)-c4ccccc4C64c5ccccc5-c5ccccc54)ccc32)cc1]\n1153-85-1 | 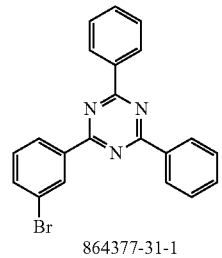 [SMILES: Brc1cccc(-c2nc(-c3ccccc3)nc(-c3ccccc3)n2)c1] | 62% |
| 7g | 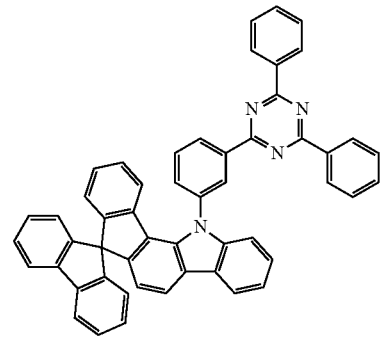 [SMILES: c1ccc(-c2nc(-c3ccccc3)nc(-c3cccc(-n4c5ccccc5c5ccc6c(c54)-c4ccccc4C64c5ccccc5-c5ccccc54)c3)n2)cc1] | 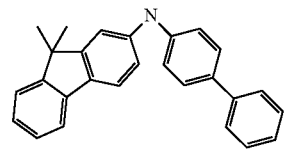\n864377-31-1 | 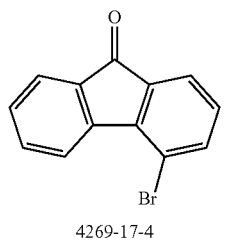 [SMILES: O=C1c2ccccc2-c2c(Br)cccc21] | 53% |
| 7h | 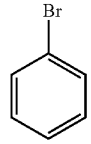\n1359833-90-1 | 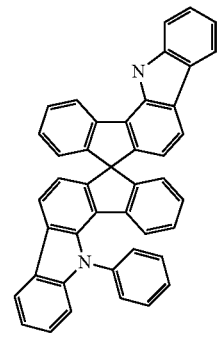 [SMILES: c1ccc(-n2c3ccccc3c3ccc4c(c32)-c2ccccc2C42c3ccccc3-c3c2ccc2c3[nH]c3ccccc32)cc1]\n4269-17-4 | | 91% (without sublimation) |
| 7j | | Br\n108-86-1 | | 82% (without sublimation) |

-continued
| Starting material 1 | Starting material 2 | Product | Yield |
|---|---|---|---|
| 7k 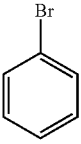 | 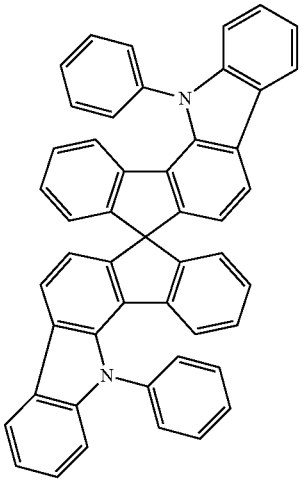 [SMILES: c1ccc(-n2c3ccccc3c3ccc4c(c32)-c2ccccc2C42c3ccccc3-c3c2ccc2c4ccccc4n(-c4ccccc4)c32)cc1] 108-86-1 | 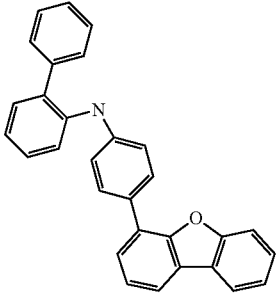 [SMILES: c1ccc(-c2ccccc2Nc2ccc(-c3cccc4c3oc3ccccc34)cc2)cc1] | 32% |
| 7l 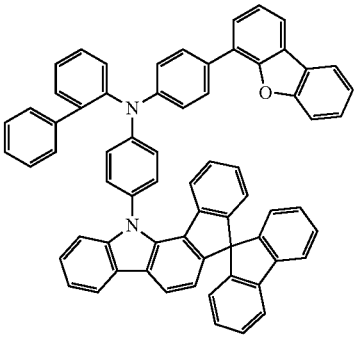 [SMILES: c1ccc(-c2ccccc2N(c2ccc(-c3cccc4c3oc3ccccc34)cc2)c2ccc(-n3c4ccccc4c4ccc5c(c43)-c3ccccc3C53c4ccccc4-c4ccccc43)cc2)cc1] | 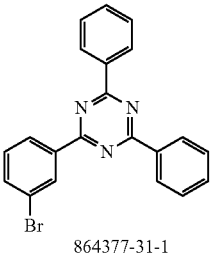 [SMILES: Brc1cccc(-c2nc(-c3ccccc3)nc(-c3ccccc3)n2)c1] | 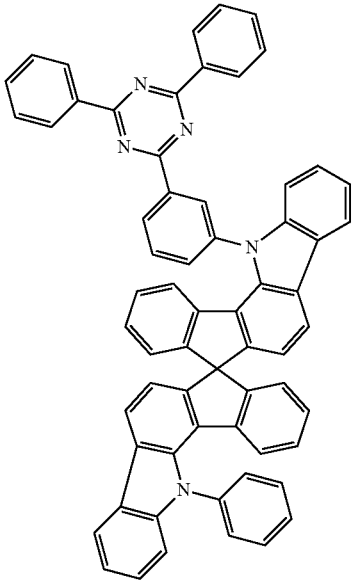 [SMILES: c1ccc(-c2nc(-c3ccccc3)nc(-c3cccc(-n4c5ccccc5c5ccc6c(c54)-c4ccccc4C64c5ccccc5-c5c4ccc4c6ccccc6n(-c6ccccc6)c54)c3)n2)cc1] | 42% |
| 7m | | | 41% |

-continued

| | Starting material 1 | Starting material 2 | Product | Yield |
|---|---|---|---|---|
| 7n | | 1359833-90-1 | | 37% |
| 7o | | 201138-91-2 | | 57% (without sublimation) |
| 7p | | | | 31% |

-continued

| | Starting material 1 | Starting material 2 | Product | Yield |
|---|---|---|---|---|
| 7q | | | | 39% |
| 7r | | 185112-61-2 | | 34% |
| 7s | | | | 48% |

Example 8

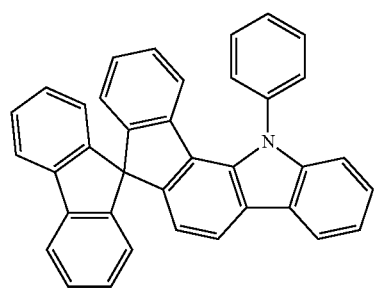

NBS, THF, RT →

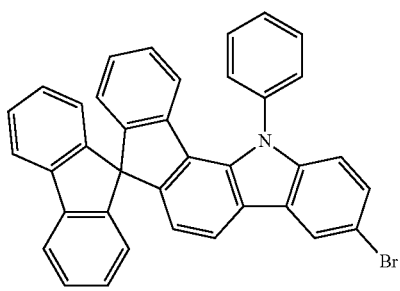

7 g (14.5 mmol) of phenyl-4-spirocarbazole and 2.7 g (15 mmol) of NBS are dissolved in 300 ml of THF in a 500 ml four-necked flask and stirred at room temperature for 48 h until the reaction is complete. The mixture is subsequently hydrolysed using 50 ml of water, and the organic solvents are removed under reduced pressure. The solid obtained is washed by stirring once with 300 ml of hot ethanol. After cooling to room temperature, the solid is filtered off. After drying under reduced pressure, the product is obtained as a colourless solid. The yield is 7.3 g (13 mmol, corresponding to 90% of theory).

Example 9a

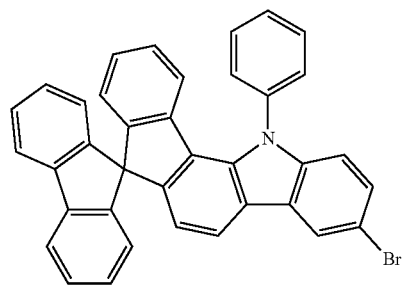 [SMILES: Brc1ccc2c(c1)c1ccc3c(c1n2-c1ccccc1)-c1ccccc1C31c2ccccc2-c2ccccc21] +

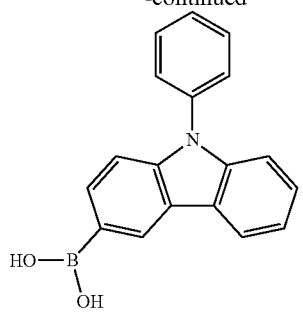 →

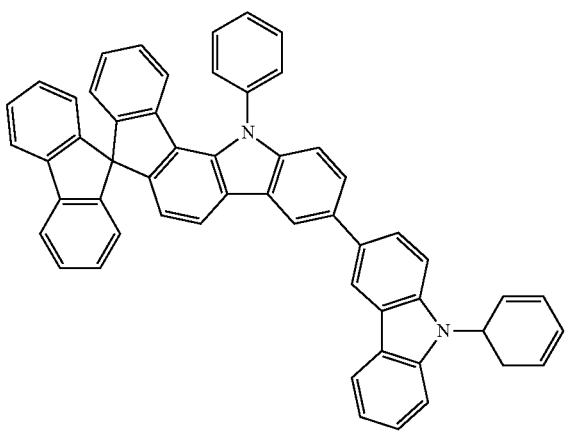

17.5 g (31 mmol) of 8a, 9.2 g (32 mmol) of phenylcarbazoleboronic acid, 26.5 g (125 mmol) of tripotassium phosphate are dissolved in 120 ml of glyme, 170 ml of toluene and 120 ml of water in a 1 l four-necked flask, and argon is passed through the mixture for 30 min. 140 mg (0.6 mmol) of palladium acetate and 380 mg (1.2 mmol) of tri-o-tolylphosphine are subsequently added, and the mixture is heated under reflux for 16 h. When the reaction is complete, the reaction mixture is cooled to room temperature, the precipitated solid is filtered off and washed with ethanol and heptane. The solid is subsequently extracted twice with hot toluene, recrystallised from heptane/toluene and sublimed at 400° C. and $2 \times 10^{-5}$ bar. The product is obtained as a colourless solid having an HPLC purity of 99.95%. The yield is 10.2 g (14 mmol, corresponding to 45% of theory).

The following compounds are prepared analogously:

| | Starting material 1 | Starting material 2 | Product | Yield |
|---|---|---|---|---|
| 9b | | 333432-28-3 | | 37% |
| 9c | | see Ex. 10 | | 38% |
| 9d | | 796071-96-0 | | 50% |
| 9e | | see Ex. 10 | | 61% |

Example 10a

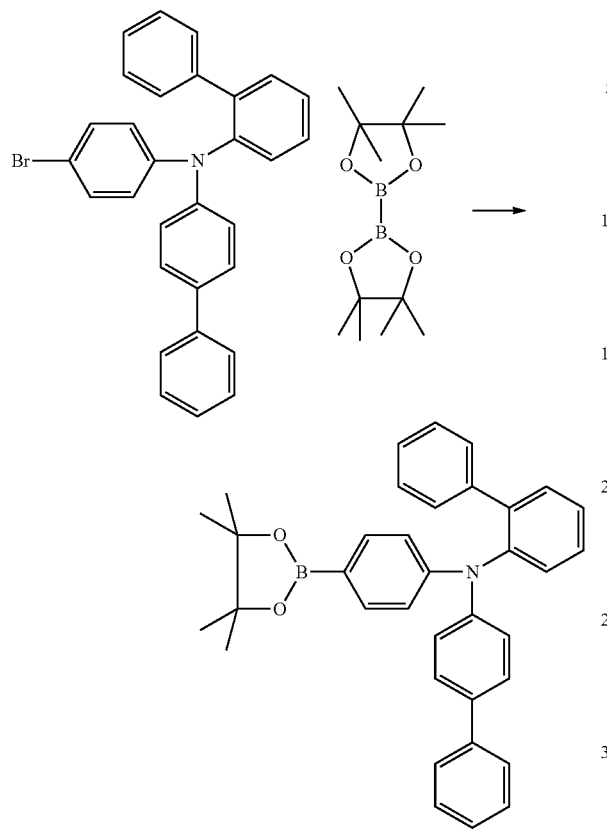

33.8 g (71 mmol) of biphenyl-2-ylbiphenyl-4-yl-(4-bromophenyl)amine (1371651-92-1), 21.9 g (86 mmol) of bispinacolatodiborane (73183-34-3), 21.7 g (221 mmol) of potassium acetate and 1.7 g (2.1 mmol) of 1,1-bis-(diphenylphosphino)ferrocene palladium(II) dichloride complex with DCM in 1000 ml of anhydrous dioxane are heated under reflux in a 2 l four-necked flask for 16 h until the reaction is complete. After cooling to room temperature, the organic phase is extended with ethyl acetate, washed three times with 300 ml of water and dried using sodium sulfate. The combined organic phases are evaporated to dryness in a rotary evaporator. After recrystallisation from heptane, the product is obtained as a solid. The yield is 22.6 g (41 mmol; 61%).

The following compound is prepared analogously:

Example 11a

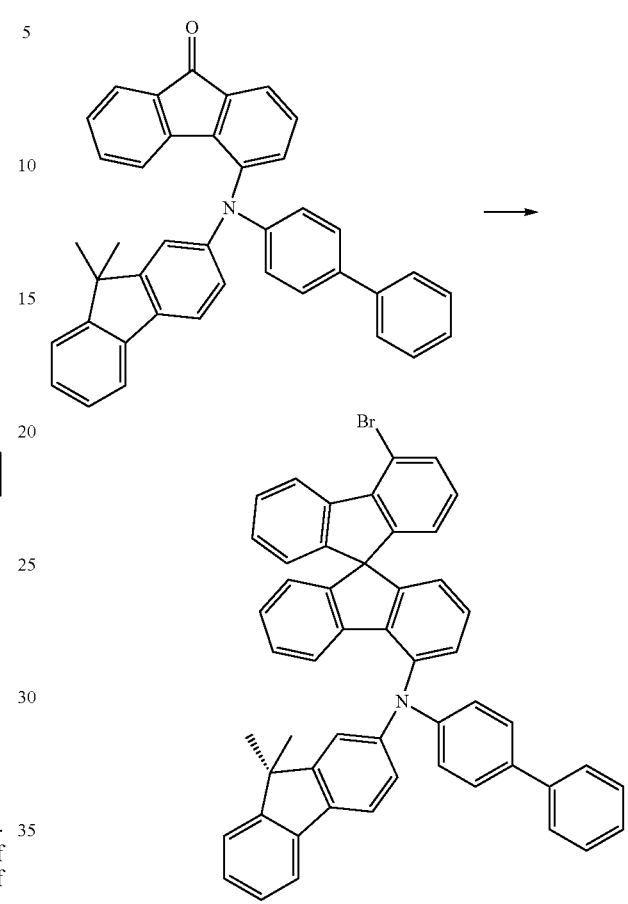

The corresponding Grignard reagent is prepared from 2.7 g (110 mmol) of iodine-activated magnesium turnings and a mixture of 25.6 g (110 mmol) of 2-bromobiphenyl, 0.8 ml of 1,2-dichloroethane, 50 ml of 1,2-dimethoxyethane, 400 ml of THF and 200 ml of toluene with secondary heating using an oil bath at 70° C. When the magnesium has reacted completely, the mixture is allowed to cool to room temperature, and a solution of 25.9 g (100 mmol) of 4-[biphenyl-4-yl-(9,9-dimethyl-9H-fluoren-2-yl)amino]fluoren-9-one (7 h) in 500 ml of THF is then added dropwise, the reaction mixture is warmed at 50° C. for 4 h and then stirred at room temperature for a further 12 h. 100 ml of water are added, the mixture is stirred briefly, the organic phase is separated off, and the solvent is removed in vacuo. The residue is suspended in 500 ml of warm glacial acetic acid at 40° C., 0.5 ml of conc. sulfuric acid is added to the suspension, and the mixture is subsequently stirred at 100° C. for a further 2 h. After cooling, the precipitated solid is filtered off with suction, washed once with 100 ml of glacial acetic acid, three times with 100 ml of ethanol each time and finally recrystallised from dioxane. Yield: 26.9 g (68 mmol), 68%; purity about 98% according to ¹H-NMR.

The following compounds are prepared analogously:

| | Starting material 1 | Starting material 2 | Product | Yield |
|---|---|---|---|---|
| 11b | 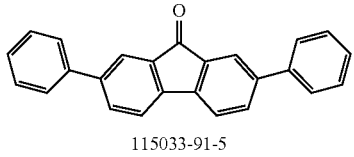 [SMILES: O=C1c2cc(-c3ccccc3)ccc2-c2ccc(-c3ccccc3)cc21]<br>115033-91-5 | 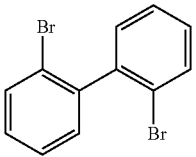<br>13029-09-9 | 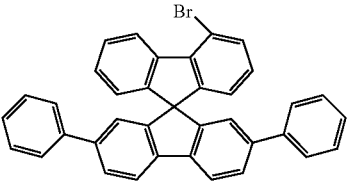 [SMILES: Brc1cccc2c1-c1ccccc1C21c2cc(-c3ccccc3)ccc2-c2ccc(-c3ccccc3)cc21] | 56% |
| 11c | 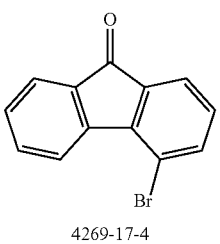 [SMILES: O=C1c2ccccc2-c2c(Br)cccc21]<br>4269-17-4 | 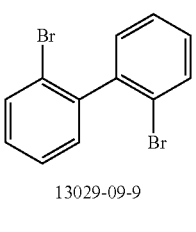 [SMILES: Brc1ccccc1-c1ccccc1Br]<br>13029-09-9 | 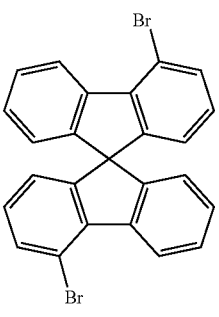 [SMILES: Brc1cccc2c1-c1ccccc1C21c2ccccc2-c2c(Br)cccc21] | 47% |
| 11d | 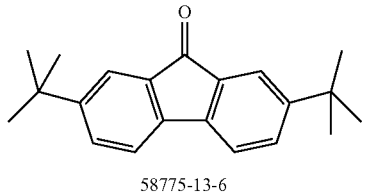 [SMILES: CC(C)(C)c1ccc2c(c1)C(=O)c1cc(C(C)(C)C)ccc1-2]<br>58775-13-6 | 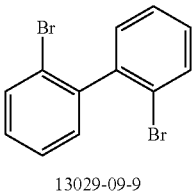 [SMILES: Brc1ccccc1-c1ccccc1Br]<br>13029-09-9 | 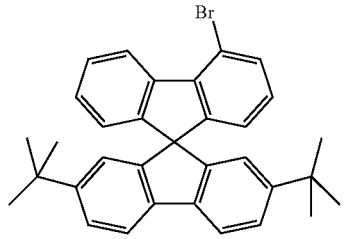 [SMILES: CC(C)(C)c1ccc2c(c1)C1(c3cc(C(C)(C)C)ccc3-2)c2ccccc2-c2c(Br)cccc21] | 49% |
| 11e | 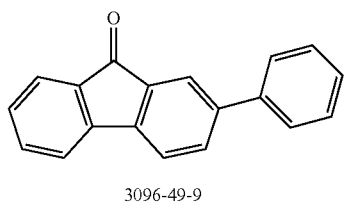 [SMILES: O=C1c2ccccc2-c2ccc(-c3ccccc3)cc21]<br>3096-49-9 | 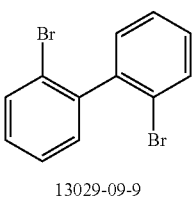 [SMILES: Brc1ccccc1-c1ccccc1Br]<br>13029-09-9 | 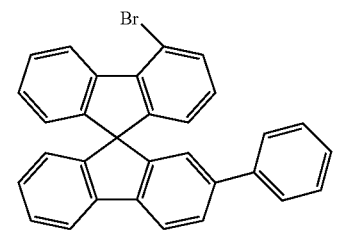 [SMILES: Brc1cccc2c1-c1ccccc1C21c2ccccc2-c2ccc(-c3ccccc3)cc21] | 51% |

Example 12: Synthesis of the Amine Building Blocks

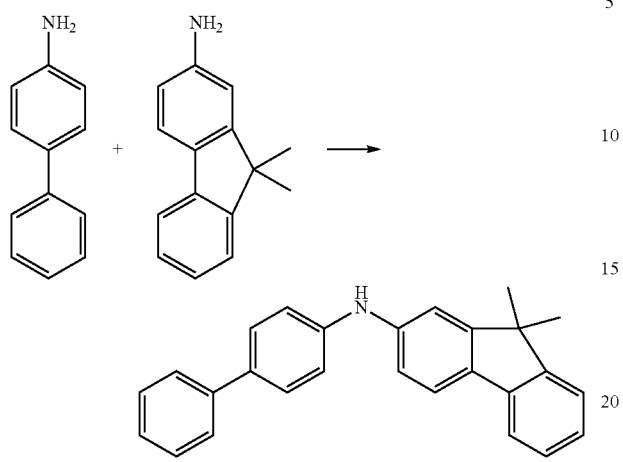

24.0 g (142 mmol, 1.2 eq.) of 4-aminobiphenyl (CAS 92-67-1) and 32.0 g (117 mmol, 1.0 eq.) of 2-bromo-9,9'-dimethylfluorene (CAS 28320-31-2) are initially introduced in 950 ml of toluene and saturated with argon for 30 minutes. 1.0 g (1.8 mmol, 0.02 eq.) of 1,1'-bis(diphenylphosphino)ferrocene (CAS 12150-46-8), 350 mg (1.6 mmol, 0.01 eq.) of palladium(II) acetate (CAS 3375-31-3) and 29 g (300 mmol, 2.6 eq.) of sodium tert-butoxide (CAS 865-48-5) are subsequently added, and the mixture is heated under reflux overnight. When the reaction is complete, the batch is diluted with 300 ml of toluene and extracted with water. The organic phase is dried over sodium sulfate, and the solvent is removed in a rotary evaporator. 50 ml of ethyl acetate are added to the brown oil, and the mixture is added to a mixture of heptane/ethyl acetate 20:1. The solid formed is filtered off with suction and washed with heptane. Drying gives 29 g (80 mmol, 69%) of the desired product having an HPLC purity of 99.1%.

The following compound is prepared analogously:

| Ex. | Starting material 1 | Starting material 2 | Product | Yield |
|---|---|---|---|---|
| 12b | ![structure] 90-41-5 | ![structure] 955959-84-9 | ![structure] | 62% |

Example 13: Introduction of the Bridge at the Amine Building Block

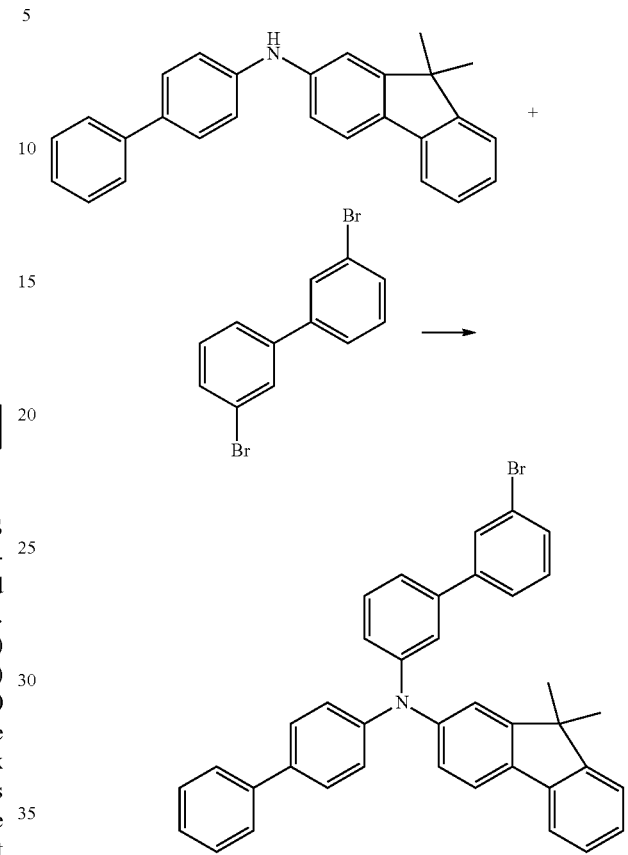

29 g (80 mmol, 1.0 eq.) of the intermediate 12a and 25 g (80 mmol, 1.0 eq.) of 3,3'-dibromo-1,1'-biphenyl (CAS 16400-51-4) are dissolved in 600 ml of toluene and degassed for 30 minutes. 45 g (240 mmol, 3.0 eq.) of sodium tert-butoxide, 890 mg (0.40 mmol, 0.050 eq.) of palladium(II) acetate and 8 ml (8.0 mmol, 0.10 eq.) of a 1M tri-tertbutylphosphine solution are subsequently added. The batch is heated under reflux overnight and, when the reaction is complete, filtered twice through aluminium oxide with toluene. After removal of the solvent in a rotary evaporator, the oil is dissolved in a little THF and introduced into heptane. The solid formed is filtered off with suction and purified by means of hot extraction with heptane/toluene 1:1, giving 16.6 g (28 mmol, 35%) of the desired product.

Example 14: Synthesis of the Triazine Building Block

Step 1:

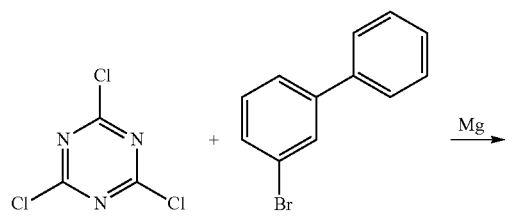

-continued

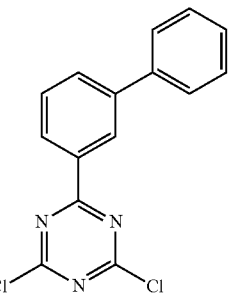

7.9 g (330 mmol, 1.2 eq.) of magnesium turnings are initially introduced in a 1 l four-necked flask, and a THF solution of 63 g (270 mmol, 1.0 eq.) of 3-bromobiphenyl (CAS 2113-57-7) is added sufficiently slowly to obtain reflux of the reaction mixture. When the addition is complete, the batch is heated under reflux for a further 2 h.

50 g (270 mmol, 1 eq.) of 2,4,6-trichloro-1,3,5-triazine (CAS 108-77-0) in 500 ml of THF are cooled to −10° C. in a 2 l four-necked flask. The Grignard solution is added dropwise at this temperature sufficiently slowly that the temperature does not exceed 0° C., and the batch is finally stirred at room temperature overnight. For work-up, 270 ml of 1N hydrochloric acid are added dropwise, and the mixture is stirred for 1 h. The aqueous phase is subsequently separated off and extracted with diethyl ether. The combined organic phases are dried over sodium sulfate, and the solvent is removed in a rotary evaporator, giving 56 g (69%) of a colourless oil.

The following compounds are prepared analogously:

| Ex. | Starting material 1 | Starting material 2 | Product | Yield |
|---|---|---|---|---|
| 14b | ![structure] | ![structure] 92-66-0 | ![structure] | 56% |
| 14c | ![structure] | ![structure] 103068-20-8 | ![structure] | 71% |

Step 2:

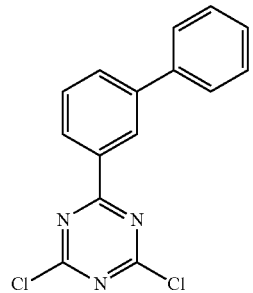

+

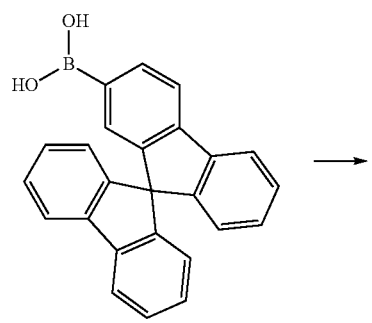

→

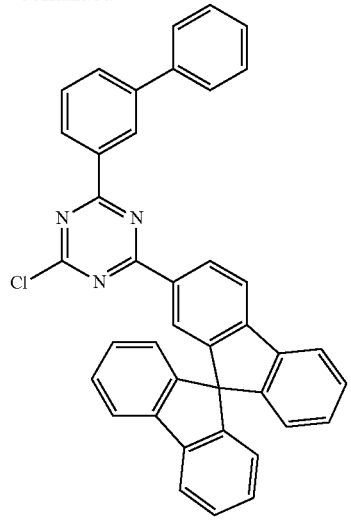

Variant A:

18 g (50 mmol, 1 eq.) of 9,9-spirobifluoren-2-ylboronic acid (CAS 236389-21-2), 15 g (50 mmol, 1 eq.) of 2-biphenyl-3-yl-4,6-dichloro-1,3,5-triazine 14a and 5.8 g (55 mmol, 1.1 eq.) of sodium carbonate are dissolved in a mixture of 200 ml of dioxane, 200 ml of toluene and 70 ml of water and degassed for 30 minutes. 580 mg (0.50 mmol, 1 mol %) of tetrakis(triphenylphosphine) (CAS 14221-01-3) are subsequently added, and the batch is heated under reflux overnight. The reaction mixture is cooled, and 300 ml of water are added. The aqueous phase is extracted three times with ethyl acetate, the organic phases are combined, and the solvent is removed in a rotary evaporator. Hot extraction with heptane/toluene 4:1 gives 15 g (26 mmol, 51%) of a colourless solid.

Variant B: analogous to step 1.

The following compounds are prepared analogously:

| Ex. | Variant | Starting material 1 | Starting material 2 | Product | Yield |
|---|---|---|---|---|---|
| 15b | A | [structure] | [structure] 100124-06-9 | [structure] | 63% |
| 15c | A | [structure] 1700-02-3 | [structure] 854952-58-2 | [structure] | 68% |

| Ex. | Variant | Starting material 1 | Starting material 2 | Product | Yield |
|---|---|---|---|---|---|
| 15d | B | 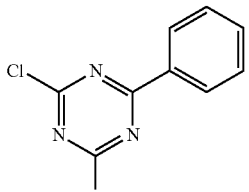 1700-02-3 | 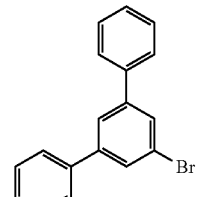 103068-20-8 | 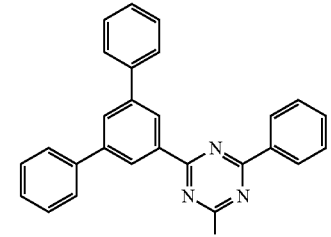 | 67% |
| 15e | B | 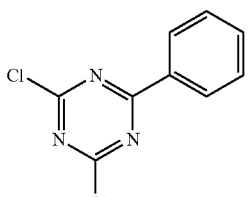 1700-02-3 | 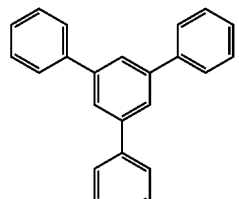 1233200-57-1 | 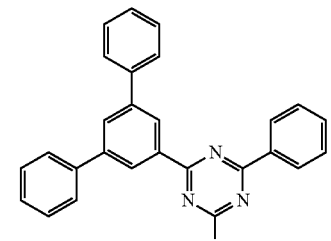 | 57% |

Example 16: Production of OLEDs

The data for various OLEDs are presented in Examples V1 to E77 below (see Tables 1 and 2).

Pretreatment for Examples V1-V7 and E1-E49

Cleaned glass plates (cleaning in Miele laboratory dishwasher, Merck Extran detergent) which have been coated with structured ITO (indium tin oxide) in a thickness of 50 nm are coated with 20 nm of PEDOT:PSS (poly(3,4-ethylenedioxythiophene)poly-(styrene sulfonate), purchased as CLEVIOS™ P VP Al 4083 from Heraeus Precious Metals GmbH, Germany, applied by spin coating from aqueous solution) for improved processing. The samples are subsequently dried by heating at 180° C. for 10 min. These coated glass plates form the substrates to which the OLEDs are applied.

Pretreatment for Examples E50-E55

Cleaned glass plates (cleaning in Miele laboratory dishwasher, Merck Extran detergent) which have been coated with structured ITO (indium tin oxide) in a thickness of 50 nm are treated with an oxygen plasma for 130 s. These plasma-treated glass plates form the substrates to which the OLEDs are applied. The substrates remain under vacuum before the coating. The coating begins within 10 min after the plasma treatment.

Pretreatment for Examples E56-E77

Cleaned glass plates (cleaning in Miele laboratory dishwasher, Merck Extran detergent) which have been coated with structured ITO (indium tin oxide) in a thickness of 50 nm are treated with an oxygen plasma for 130 s and subsequently with an argon plasma for 150 s. These plasma-treated glass plates form the substrates to which the OLEDs are applied. The substrates remain under vacuum before the coating. The coating begins within 10 min after the plasma treatment.

The OLEDs basically have the following layer structure: substrate/optional hole-injection layer (HIL)/hole-transport layer (HTL)/interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 1. The materials required for the production of the OLEDs are shown in Table 3. A designation such as "3a" here relates to the materials shown in the tables for Example 3a. An analogous situation applies to the other materials.

The synthesis of compound WB1 is carried out analogously to WO 2009/124627. The synthesis of compound TEG3 is described in WO 2011/032626, of compound TER2 in WO 2011/032626, of compound IC4 in WO 2010/136109.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as ST1:7b:TEG1 (30%:58%:12%) here means that material ST1 is present in the layer in a proportion by volume of 30%, 7b is present in the layer in a proportion of 58% and TEG1 is present in the layer in a proportion of 12%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931 x and y colour coordinates are calculated therefrom. The term U1000 in Table 2 denotes the voltage required for a luminous density of 1000 cd/m². CE1000 and PE1000 denote the current and power efficiency respectively which are achieved at 1000 cd/m². Finally, EQE1000 denotes the external quantum efficiency at an operating luminous density of 1000 cd/m².

The lifetime LT is defined as the time after which the luminous density has dropped from the initial luminous density to a certain proportion L1 on operation at constant current. An expression of L0;j0=4000 cd/m² and L1=70% in Table X2 means that the lifetime indicated in column LT corresponds to the time after which the luminous density has dropped from its initial value of 4000 cd/m² to 2800 cd/m². Analogously, L0;j0=20 mA/cm², L1=80%, means that the luminous density drops to 80% of its initial value after time LT on operation at 20 mA/cm².

The data for the various OLEDs are summarised in Table 2. Examples V1-V7 are comparative examples in accordance with the prior art, Examples E1-E77 show data for OLEDs comprising materials according to the invention.

Some of the examples are explained in greater detail below in order to illustrate the advantages of the compounds according to the invention. However, it should be pointed out that this only represents a selection of the data shown in Table 2. As can be seen from the table, significant improvements over the prior art are also achieved on use of the compounds according to the invention which are not described in greater detail, in some cases in all parameters, but in some cases only an improvement in efficiency or voltage or lifetime is observed. However, even the improvement in one of the said parameters represents a significant advance, since various applications require optimisation with respect to different parameters.

Use of Compounds According to the Invention as Electron-Transport Materials

If, instead of the diphenylfluorene compound StdT2 in accordance with the prior art, the analogous Spiro compound 3a according to the invention is used as electron-transport material, a significant improvement in the power efficiency of about 15% is obtained in combination with the green-phosphorescent dopant TEG1 owing to the significantly improved voltage and the improved external quantum efficiency. The lifetime is likewise slightly improved (Examples V6, E24). Very good performance data are also obtained in combination with the blue-fluorescent dopant D1 (Example E25).

Use of Compounds According to the Invention as Matrix Materials in Phosphorescent OLEDs In combination with the green-phosphorescent dopant TEG1, a significant improvement in the voltage of 0.3 V and the lifetime of 35% compared with compound StdT1, in which the triazine group is bonded to the fluorene part of the spiro, is obtained on use of compound 3a according to the invention, in which the triazine is bonded via the nitrogen. The external quantum efficiency is also improved, which results overall in a significant improvement in the power efficiency of virtually 20% (Examples V1, E1). Compared with the diphenylfluorene compound StdT2, an improvement in the lifetime, in particular, is observed (Examples V4, E1). Similar improvements arise in combination with the red-phosphorescent dopant TER1 on use of compounds according to the invention (Examples V5, E30, E31).

On combination with compound IC3 in the emission layer, significant advantages are likewise obtained by the compounds according to the invention (Examples V7, E21), especially an improvement in the lifetime of virtually 40%.

Finally, the combination of compounds according to the invention with compound ST1 or IC2 in the emission layer results in very good performance data (Examples E39, E40, E41, E42).

TABLE 1

Structure of the OLEDs

| Ex. | HIL Thickness | HTL Thickness | IL Thickness | EBL Thickness | EML Thickness | HBL Thickness | ETL Thickness | EIL Thickness |
|---|---|---|---|---|---|---|---|---|
| V1 | — | SpA1 70 nm | HATCN 5 nm | SpMA1 90 nm | StdT1:TEG1 (90%:10%) 30 nm | — | ST2:LiQ (50%:50%) 40 nm | — |
| V2 | — | SpA1 70 nm | HATCN 5 nm | SpMA1 90 nm | StdT2:TEG2 (90%:17%) 30 nm | ST2 10 nm | ST2:LiQ (50%:50%) 30 nm | — |
| V3 | — | SpA1 70 nm | HATCN 5 nm | SpMA1 90 nm | StdT3:TEG2 (90%:17%) 30 nm | — | ST2:LiQ (50%:50%) 40 nm | — |
| V4 | — | SpA1 70 nm | HATCN 5 nm | SpMA1 90 nm | StdT2:TEG1 (90%:10%) 30 nm | — | ST2:LiQ (50%:50%) 40 nm | — |
| V5 | — | SpA1 90 nm | HATCN 5 nm | SpMA1 130 nm | StdT1:TER1 (92%:8%) 40 nm | — | ST2:LiQ (50%:50%) 40 nm | — |
| V6 | — | SpA1 70 nm | HATCN 5 nm | SpMA1 90 nm | IC1:TEG1 (90%:10%) 30 nm | — | StdT2 40 nm | LiQ 4 nm |
| V7 | — | SpA1 70 nm | HATCN 5 nm | SpMA1 90 nm | StdT2:IC3:TEG1 (45%:45%:10%) 30 nm | IC1 10 nm | ST2:LiQ (50%:50%) 30 nm | — |
| E1 | — | SpA1 70 nm | HATCN 5 nm | SpMA1 90 nm | 3a:TEG1 (90%:10%) 30 nm | — | ST2:LiQ (50%:50%) 40 nm | — |
| E2 | — | SpA1 70 nm | HATCN 5 nm | SpMA1 90 nm | 3a:TEG2 (90%:17%) 30 nm | — | ST2:LiQ (50%:50%) 40 nm | — |
| E3 | — | SpA1 70 nm | HATCN 5 nm | SpMA1 90 nm | 3a:TEG2 (90%:17%) 30 nm | ST2 10 nm | ST2:LiQ (50%:50%) 30 nm | — |
| E4 | — | SpA1 70 nm | HATCN 5 nm | SpMA1 90 nm | 3j:TEG1 (90%:10%) 30 nm | — | ST2:LiQ (50%:50%) 40 nm | — |
| E5 | — | SpA1 70 nm | HATCN 5 nm | SpMA1 90 nm | 3b:TEG1 (90%:10%) 30 nm | — | ST2:LiQ (50%:50%) 40 nm | — |
| E6 | — | SpA1 70 nm | HATCN 5 nm | SpMA1 90 nm | 3g:TEG1 (90%:10%) 30 nm | — | ST2:LiQ (50%:50%) 40 nm | — |
| E7 | — | SpA1 70 nm | HATCN 5 nm | SpMA1 90 nm | 3k:TEG1 (90%:10%) 30 nm | — | ST2:LiQ (50%:50%) 40 nm | — |
| E8 | — | SpA1 70 nm | HATCN 5 nm | SpMA1 90 nm | 3l:TEG1 (90%:10%) 30 nm | — | ST2:LiQ (50%:50%) 40 nm | — |

TABLE 1-continued

Structure of the OLEDs

| Ex. | HIL Thickness | HTL Thickness | IL Thickness | EBL Thickness | EML Thickness | HBL Thickness | ETL Thickness | EIL Thickness |
|---|---|---|---|---|---|---|---|---|
| E9 | — | SpA1 70 nm | HATCN 5 nm | SpMA1 90 nm | 3m:TEG1 (90%:10%) 30 nm | — | ST2:LiQ (50%:50%) 40 nm | — |
| E10 | — | SpA1 70 nm | HATCN 5 nm | SpMA1 90 nm | 3n:TEG1 (90%:10%) 30 nm | — | ST2:LiQ (50%:50%) 40 nm | — |
| E11 | — | SpA1 70 nm | HATCN 5 nm | SpMA1 90 nm | 3o:TEG1 (90%:10%) 30 nm | — | ST2:LiQ (50%:50%) 40 nm | — |
| E12 | — | SpA1 70 nm | HATCN 5 nm | SpMA1 90 nm | 6g:TEG1 (90%:10%) 30 nm | — | ST2:LiQ (50%:50%) 40 nm | — |
| E13 | — | SpA1 70 nm | HATCN 5 nm | SpMA1 90 nm | 6e:TEG1 (90%:10%) 30 nm | — | ST2:LiQ (50%:50%) 40 nm | — |
| E14 | — | SpA1 70 nm | HATCN 5 nm | SpMA1 90 nm | 6e:7a:TEG1 (30%:55%:15%) 30 nm | IC1 10 nm | ST2:LiQ (50%:50%) 40 nm | — |
| E15 | — | SpA1 70 nm | HATCN 5 nm | SpMA1 90 nm | 7m:TEG1 (90%:10%) 30 nm | — | ST2:LiQ (50%:50%) 40 nm | — |
| E16 | — | SpA1 70 nm | HATCN 5 nm | SpMA1 90 nm | IC2:7k:TEG1 (40%:45%:15%) 30 nm | IC1 10 nm | ST2:LiQ (50%:50%) 40 nm | — |
| E17 | — | SpA1 70 nm | HATCN 5 nm | SpMA1 90 nm | IC2:9b:TEG1 (30%:55%:15%) 30 nm | IC1 10 nm | ST2:LiQ (50%:50%) 40 nm | — |
| E18 | — | SpA1 70 nm | HATCN 5 nm | SpMA1 90 nm | IC2:9d:TEG1 (30%:55%:15%) 30 nm | IC1 10 nm | ST2:LiQ (50%:50%) 40 nm | — |
| E19 | — | SpA1 70 nm | HATCN 5 nm | SpMA1 90 nm | IC2:9h:TEG1 (30%:55%:15%) 30 nm | IC1 10 nm | ST2:LiQ (50%:50%) 40 nm | — |
| E20 | — | SpA1 70 nm | HATCN 5 nm | SpMA1 90 nm | IC1:TEG1 (90%:10%) 30 nm | 3a 10 nm | ST2:LiQ (50%:50%) 30 nm | — |
| E21 | — | SpA1 70 nm | HATCN 5 nm | SpMA1 90 nm | 3a:IC3:TEG1 (45%:45%:10%) 30 nm | IC1 10 nm | ST2:LiQ (50%:50%) 30 nm | — |
| E22 | — | SpA1 70 nm | HATCN 5 nm | SpMA1 90 nm | IC1:TEG1 (90%:10%) 30 nm | — | 3a 40 nm | LiQ 4 nm |
| E23 | — | SpA1 70 nm | HATCN 5 nm | SpMA1 90 nm | IC1:TEG1 (90%:10%) 30 nm | — | 6i 40 nm | LiF 1 nm |
| E24 | — | SpA1 70 nm | HATCN 5 nm | SpMA1 90 nm | IC1:TEG1 (90%:10%) 30 nm | — | 7p 40 nm | LiF 1 nm |
| E25 | HATCN 5 nm | SpA1 140 nm | HATCN 5 nm | SpMA1 20 nm | M1:D1 (95%:5%) 20 nm | 3a 30 nm | LiQ 4 nm |
| E26 | SpA1 70 nm | HATCN 5 nm | SpMA1 80 nm | 9c 10 nm | IC2:TEG2 (83%:17%) 30 nm | — | ST2:LiQ (50%:50%) 40 nm | — |
| E27 | SpA1 70 nm | HATCN 5 nm | SpMA1 80 nm | 7s 10 nm | IC2:TEG2 (83%:17%) 30 nm | — | ST2:LiQ (50%:50%) 40 nm | — |
| E28 | SpA1 70 nm | HATCN 5 nm | SpMA1 80 nm | 7l 10 nm | IC2:TEG2 (83%:17%) 30 nm | — | ST2:LiQ (50%:50%) 40 nm | — |
| E29 | SpA1 70 nm | HATCN 5 nm | SpMA1 80 nm | 7n 10 nm | IC2:TEG2 (83%:17%) 30 nm | — | ST2:LiQ (50%:50%) 40 nm | — |
| E30 | — | SpA1 90 nm | HATCN 5 nm | SpMA1 130 nm | 3c:TER1 (92%:8%) 40 nm | — | ST2:LiQ (50%:50%) 40 nm | — |
| E31 | — | SpA1 90 nm | HATCN 5 nm | SpMA1 130 nm | 3f:TER1 (92%:8%) 40 nm | — | ST2:LiQ (50%:50%) 40 nm | — |
| E32 | — | SpA1 90 nm | HATCN 5 nm | SpMA1 130 nm | IC2:7q:TER1 (92%:12%) 40 nm | — | ST2:LiQ (50%:50%) 40 nm | — |
| E33 | — | SpA1 90 nm | HATCN 5 nm | SpMA1 130 nm | IC2:7r:TER1 (92%:12%) 40 nm | — | ST2:LiQ (50%:50%) 40 nm | — |
| E34 | — | SpA1 90 nm | HATCN 5 nm | SpMA1 130 nm | IC2:7f:TER1 (92%:12%) 40 nm | — | ST2:LiQ (50%:50%) 40 nm | — |
| E35 | — | SpA1 70 nm | HATCN 5 nm | SpMA1 90 nm | 6a:TEG1 (90%:10%) 30 nm | — | ST2:LiQ (50%:50%) 40 nm | — |
| E36 | — | SpA1 70 nm | HATCN 5 nm | SpMA1 90 nm | 6b:TEG1 (90%:10%) 30 nm | — | ST2:LiQ (50%:50%) 40 nm | — |
| E37 | — | SpA1 70 nm | HATCN 5 nm | SpMA1 90 nm | 6c:TEG1 (90%:10%) 30 nm | — | ST2:LiQ (50%:50%) 40 nm | — |
| E38 | — | SpA1 70 nm | HATCN 5 nm | SpMA1 90 nm | 6f:TEG1 (90%:10%) 30 nm | — | ST2:LiQ (50%:50%) 40 nm | — |
| E39 | — | SpA1 70 nm | HATCN 5 nm | SpMA1 90 nm | ST1:7a:TEG1 (30%:58%:12%) 30 nm | IC1 10 nm | ST2:LiQ (50%:50%) 30 nm | — |
| E40 | — | SpA1 70 nm | HATCN 5 nm | SpMA1 90 nm | ST1:7b:TEG1 (30%:58%:12%) 30 nm | IC1 10 nm | ST2:LiQ (50%:50%) 30 nm | — |
| E41 | — | SpA1 70 nm | HATCN 5 nm | SpMA1 90 nm | ST1:7c:TEG1 (30%:58%:12%) 30 nm | IC1 10 nm | ST2:LiQ (50%:50%) 30 nm | — |
| E42 | — | SpA1 90 nm | HATCN 5 nm | SpMA1 130 nm | IC2:7d:TER1 (30%:60%:10%) 40 nm | — | ST2:LiQ (50%:50%) 40 nm | — |
| E43 | — | SpA1 70 nm | HATCN 5 nm | SpMA1 90 nm | IC2:3i:TEG2 (44%:44%:12%) 30 nm | ST2 10 nm | ST2:LiQ (50%:50%) 30 nm | — |
| E44 | — | SpA1 70 nm | HATCN 5 nm | SpMA1 90 nm | 3i:TEG2 (88%:12%) 30 nm | ST2 10 nm | ST2:LiQ (50%:50%) 30 nm | — |
| E45 | — | SpA1 70 nm | HATCN 5 nm | SpMA1 90 nm | 3j:TEG2 (83%:17%) 30 nm | ST2 10 nm | ST2:LiQ (50%:50%) 30 nm | — |

TABLE 1-continued

Structure of the OLEDs

| Ex. | HIL Thickness | HTL Thickness | IL Thickness | EBL Thickness | EML Thickness | HBL Thickness | ETL Thickness | EIL Thickness |
|---|---|---|---|---|---|---|---|---|
| E46 | — | SpA1 70 nm | HATCN 5 nm | SpMA1 90 nm | IC2:7e:TEG2 (28%:55%:17%) 30 nm | ST2 10 nm | ST2:LiQ (50%:50%) 30 nm | — |
| E47 | — | SpA1 70 nm | HATCN 5 nm | SpMA1 90 nm | IC2:9a:TEG2 (44%:44%:12%) 30 nm | ST2 10 nm | ST2:LiQ (50%:50%) 30 nm | — |
| E48 | — | SpA1 70 nm | HATCN 5 nm | SpMA1 90 nm | IC2:9e:TEG2 (44%:44%:12%) 30 nm | ST2 10 nm | ST2:LiQ (50%:50%) 30 nm | — |
| E49 | — | SpA1 70 nm | HATCN 5 nm | SpMA1 90 nm | 7g:TEG2 (80%:20%) 30 nm | ST2 10 nm | ST2:LiQ (50%:50%) 30 nm | — |
| E50 | HATCN 5 nm | — | — | SpMA2 90 m | L2:3a:TEY1 (45%:45%:10%) 30 nm | — | ST1 40 nm | LiQ 3 nm |
| E51 | HATCN 5 nm | — | — | SpMA5 90 m | L2:3a:TEY1 (45%:45%:10%) 30 nm | — | ST1 40 nm | LiQ 3 nm |
| E52 | HATCN 5 nm | — | — | SpMA4 90 m | L2:3a:TEY1 (45%:45%:10%) 30 nm | — | ST1 40 nm | LiQ 3 nm |
| E53 | HATCN 5 nm | — | — | SpMA6 90 m | L2:3a:TEY1 (45%:5%:10%) 30 nm | — | ST1 40 nm | LiQ 3 nm |
| E54 | HATCN 5 nm | — | — | SpMA2 90 m | 3a:7e:TEY1 (45%:45%:10%) 30 nm | — | ST1 40 nm | LiQ 3 nm |
| E55 | HATCN 5 nm | SpMA1 70 nm | — | SpMA2 10 m | IC2:9a:TEY1 (55%:35%:10%) 25 nm | — | ST1 45 nm | LiQ 3 nm |
| E56 | SpMA1:F4T (95%:5%) 20 nm | — | SpMA1 200 nm | SpMA3 20 nm | 3a:L1:TEG2 (53%:30%:17%) 30 nm | ST2 10 nm | ST2:LiQ (50%:50%) 30 nm | LiQ 1 nm |
| E57 | SpMA1:F4T (95%:5%) 20 nm | — | SpMA1 200 nm | SpMA3 20 nm | 3a:L1:TEG2 (38%:50%:12%) 30 nm | ST2 10 nm | ST2:LiQ (50%:50%) 30 nm | LiQ 1 nm |
| E58 | SpMA1:F4T (95%:5%) 20 nm | — | SpMA1 200 nm | SpMA3 20 nm | 3a:L1:TEG2 (33%:50%:17%) 30 nm | ST2 10 nm | ST2:LiQ (50%:50%) 30 nm | LiQ 1 nm |
| E59 | SpMA1:F4T (95%:5%) 20 nm | — | SpMA1 200 nm | SpMA3 20 nm | 7g:L1:TEG2 (53%:30%:17%) 30 nm | ST2 10 nm | ST2:LiQ (50%:50%) 30 nm | LiQ 1 nm |
| E60 | SpMA1:F4T (95%:5%) 20 nm | — | SpMA1 200 nm | SpMA3 20 nm | 7g:L1:TEG2 (38%:50%:12%) 30 nm | ST2 10 nm | ST2:LiQ (50%:50%) 30 nm | LiQ 1 nm |
| E61 | SpMA1:F4T (95%:5%) 20 nm | — | SpMA1 200 nm | SpMA3 20 nm | L2:9a:TEG2 (60%:25%:15%) 30 nm | ST2 10 nm | ST2:LiQ (50%:50%) 30 nm | LiQ 1 nm |
| E62 | SpMA1:F4T (95%:5%) 20 nm | — | SpMA1 200 nm | SpMA4 20 nm | L2:9a:TEG2 (60%:25%:15%) 30 nm | ST2 10 nm | ST2:LiQ (50%:50%) 30 nm | LiQ 1 nm |
| E63 | SpMA1:F4T (95%:5%) 20 nm | — | SpMA1 210 nm | SpMA2 20 nm | IC2:9a:TEG2 (57%:28%:15%) 30 nm | — | ST2:LiQ (50%:50%) 40 nm | — |
| E64 | SpMA1:F4T (95%:5%) 20 nm | — | — | SpMA1 220 nm | 3a:L3:TEG2 (35%:45%:20%) | — | ST2:LiQ (50%:50%) 40 nm | — |
| E65 | SpMA1:F4T (95%:5%) 20 nm | — | — | SpMA1 220 nm | 3a:L3:TEG2 (45%:45%:10%) | — | ST2:LiQ (50%:50%) 40 nm | — |
| E66 | SpMA1:F4T (95%:5%) 20 nm | — | — | SpMA1 220 nm | 3a:L3:TEG2 (40%:45%:15%) | — | ST2:LiQ (50%:50%) 40 nm | — |
| E67 | SpMA1:F4T (95%:5%) 20 nm | — | SpMA1 210 nm | SpMA2 10 nm | 3a:L3:TEG2 (35%:45%:20%) | — | ST2:LiQ (50%:50%) 40 nm | — |
| E68 | SpMA1:F4T (95%:5%) 20 nm | — | SpMA1 210 nm | SpMA2 10 nm | 3a:L3:TEG2 (40%:45%:15%) | — | ST2:LiQ (50%:50%) 40 nm | — |
| E69 | SpMA1:F4T (95%:5%) 20 nm | — | SpMA1 200 nm | SpMA2 20 nm | L2:3a:TEG2 (63%:25%:12%) | ST2 10 nm | ST2:LiQ (50%:50%) 30 nm | LiQ 1 nm |
| E70 | SpMA1:F4T (95%:5%) 20 nm | — | SpMA1 200 nm | SpMA2 20 nm | L2:3a:TEG2 (58%:25%:17%) | ST2 10 nm | ST2:LiQ (50%:50%) 30 nm | LiQ 1 nm |
| E71 | SpMA1:F4T (95%:5%) 20 nm | — | SpMA1 200 nm | SpMA2 20 nm | L2:3a:TEG2 (38%:45%:17%) | ST2 10 nm | ST2:LiQ (50%:50%) 30 nm | LiQ 1 nm |
| E72 | SpMA1:F4T (95%:5%) 20 nm | — | SpMA1 200 nm | SpMA2 20 nm | L2:3a:TEG2 (18%:65%:17%) | ST2 10 nm | ST2:LiQ (50%:50%) 30 nm | LiQ 1 nm |
| E73 | SpMA1:F4T (95%:5%) 20 nm | — | SpMA1 200 nm | SpMA4 20 nm | L2:3a:TEG2 (83%:25%:12%) | ST2 10 nm | ST2:LiQ (50%:50%) 30 nm | LiQ 1 nm |
| E74 | SpMA1:F4T (95%:5%) 20 nm | — | SpMA1 200 nm | SpMA4 20 nm | L2:3a:TEG2 (43%:45%:12%) | ST2 10 nm | ST2:LiQ (50%:50%) 30 nm | LiQ 1 nm |
| E75 | SpMA1:F4T (95%:5%) 20 nm | — | SpMA1 200 nm | SpMA4 20 nm | L2:3a:TEG2 (58%:25%:17%) | ST2 10 nm | ST2:LiQ (50%:50%) 30 nm | LiQ 1 nm |
| E76 | SpMA1:F4T (95%:5%) 20 nm | — | SpMA1 200 nm | SpMA4 20 nm | L2:3a:TEG2 (38%:45%:17%) | ST2 10 nm | ST2:LiQ (50%:50%) 30 nm | LiQ 1 nm |
| E77 | SpMA1:F4T (95%:5%) 20 nm | — | SpMA1 200 nm | SpMA4 20 nm | L2:3a:TEG2 (18%:65%:17%) | ST2 10 nm | ST2:LiQ (50%:50%) 30 nm | LiQ 1 nm |

TABLE 2

Data for the OLEDs

| Ex. | U1000 (V) | CE1000 (cd/A) | PE1000 (lm/W) | EQE 1000 | CIE x/y at 1000 cd/m² | L0; j0 | L1 % | LT (h) |
|---|---|---|---|---|---|---|---|---|
| V1 | 3.6 | 56 | 49 | 15.5% | 0.33/0.62 | 20 mA/cm² | 80 | 155 |
| V2 | 3.3 | 61 | 58 | 15.8% | 0.34/0.62 | 40 mA/cm² | 80 | 100 |
| V3 | 3.3 | 57 | 54 | 14.9% | 0.34/0.62 | 40 mA/cm² | 80 | 190 |
| V4 | 3.3 | 60 | 56 | 16.8% | 0.33/0.62 | 20 mA/cm² | 80 | 130 |
| V5 | 5.3 | 9.5 | 5.7 | 10.3% | 0.67/0.33 | 4000 cd/m² | 80 | 335 |
| V6 | 3.4 | 61 | 56 | 17.3% | 0.34/0.62 | 20 mA/cm² | 80 | 160 |
| V7 | 3.3 | 56 | 54 | 15.7% | 0.33/0.62 | 20 mA/cm² | 80 | 310 |
| E1 | 3.3 | 61 | 58 | 16.8% | 0.35/0.61 | 20 mA/cm² | 80 | 210 |
| E2 | 3.2 | 63 | 63 | 16.4% | 0.34/0.62 | 40 mA/cm² | 80 | 205 |
| E3 | 3.3 | 64 | 61 | 16.6% | 0.34/0.62 | 40 mA/cm² | 80 | 210 |
| E4 | 3.3 | 64 | 61 | 16.6% | 0.34/0.62 | 20 mA/cm² | 80 | 230 |
| E5 | 3.4 | 58 | 54 | 16.2% | 0.33/0.62 | 20 mA/cm² | 80 | 185 |
| E6 | 3.2 | 61 | 59 | 16.9% | 0.35/0.62 | 20 mA/cm² | 80 | 200 |
| E7 | 3.4 | 68 | 63 | 17.6% | 0.34/0.62 | 20 mA/cm² | 80 | 175 |
| E8 | 3.3 | 54 | 51 | 14.9% | 0.35/0.61 | 20 mA/cm² | 80 | 220 |
| E9 | 3.5 | 56 | 51 | 15.5% | 0.33/0.62 | 20 mA/cm² | 80 | 180 |
| E10 | 3.2 | 65 | 64 | 16.9% | 0.34/0.62 | 20 mA/cm² | 80 | 220 |
| E11 | 3.5 | 55 | 49 | 15.2% | 0.33/0.61 | 20 mA/cm² | 80 | 190 |
| E12 | 3.1 | 59 | 60 | 16.3% | 0.34/0.62 | 20 mA/cm² | 80 | 205 |
| E13 | 3.3 | 67 | 65 | 18.0% | 0.34/0.62 | 20 mA/cm² | 80 | 140 |
| E14 | 3.1 | 68 | 68 | 18.2% | 0.34/0.62 | 20 mA/cm² | 80 | 245 |
| E15 | 3.4 | 57 | 54 | 16.2% | 0.33/0.62 | 20 mA/cm² | 80 | 155 |
| E16 | 3.2 | 66 | 64 | 17.8% | 0.33/0.62 | 20 mA/cm² | 80 | 270 |
| E17 | 3.1 | 58 | 59 | 15.8% | 0.34/0.62 | 20 mA/cm² | 80 | 325 |
| E18 | 3.5 | 61 | 55 | 16.5% | 0.34/0.62 | 20 mA/cm² | 80 | 340 |
| E19 | 3.3 | 63 | 68 | 16.6% | 0.34/0.62 | 20 mA/cm² | 80 | 290 |
| E20 | 3.2 | 65 | 64 | 18.3% | 0.33/0.62 | 20 mA/cm² | 80 | 190 |
| E21 | 3.2 | 57 | 55 | 16.0% | 0.34/0.63 | 20 mA/cm² | 80 | 425 |
| E22 | 3.1 | 66 | 68 | 18.5% | 0.33/0.62 | 20 mA/cm² | 80 | 170 |
| E23 | 3.8 | 54 | 45 | 15.4% | 0.34/0.62 | 20 mA/cm² | 80 | 190 |
| E24 | 3.3 | 62 | 59 | 17.5% | 0.34/0.62 | 20 mA/cm² | 80 | 205 |
| E25 | 4.4 | 8.7 | 6.2 | 6.6% | 0.14/0.16 | 6000 cd/m² | 70 | 185 |
| E26 | 3.2 | 58 | 58 | 15.7% | 0.34/0.62 | 40 mA/cm² | 80 | 190 |
| E27 | 3.1 | 59 | 59 | 15.9% | 0.34/0.62 | 40 mA/cm² | 80 | 180 |
| E28 | 3.2 | 59 | 57 | 16.3% | 0.33/0.62 | 40 mA/cm² | 80 | 205 |
| E29 | 3.2 | 54 | 54 | 15.5% | 0.34/0.62 | 40 mA/cm² | 80 | 165 |
| E30 | 4.8 | 9.8 | 6.4 | 10.6% | 0.67/0.33 | 4000 cd/m² | 80 | 360 |
| E31 | 4.6 | 11.0 | 7.5 | 11.9% | 0.67/0.33 | 4000 cd/m² | 80 | 380 |
| E32 | 5.0 | 9.4 | 5.9 | 10.2% | 0.67/0.33 | 4000 cd/m² | 80 | 440 |
| E33 | 4.6 | 10.4 | 7.1 | 11.3% | 0.67/0.33 | 4000 cd/m² | 80 | 480 |
| E34 | 4.7 | 11.4 | 7.7 | 12.3% | 0.67/0.33 | 4000 cd/m² | 80 | 515 |
| E35 | 3.2 | 55 | 54 | 15.3% | 0.34/0.62 | 20 mA/cm² | 80 | 165 |
| E36 | 3.0 | 63 | 65 | 17.5% | 0.33/0.61 | 20 mA/cm² | 80 | 200 |
| E37 | 3.4 | 68 | 64 | 18.9% | 0.34/0.62 | 20 mA/cm² | 80 | 140 |
| E38 | 3.2 | 54 | 52 | 15.0% | 0.34/0.62 | 20 mA/cm² | 80 | 150 |
| E39 | 3.3 | 58 | 55 | 16.1% | 0.33/0.62 | 20 mA/cm² | 80 | 330 |
| E40 | 3.2 | 62 | 61 | 17.2% | 0.34/0.63 | 20 mA/cm² | 80 | 390 |
| E41 | 3.4 | 65 | 62 | 18.4% | 0.33/0.62 | 20 mA/cm² | 80 | 410 |
| E42 | 4.4 | 11.6 | 8.2 | 12.5% | 0.67/0.33 | 4000 cd/m² | 80 | 540 |
| E43 | 3.0 | 58 | 61 | 15.7% | 0.34/0.62 | 40 mA/cm² | 80 | 200 |
| E44 | 3.3 | 56 | 54 | 15.3% | 0.34/0.62 | 40 mA/cm² | 80 | 175 |
| E45 | 3.2 | 58 | 57 | 16.1% | 0.34/0.62 | 40 mA/cm² | 80 | 185 |
| E46 | 3.3 | 60 | 57 | 16.3% | 0.34/0.62 | 40 mA/cm² | 80 | 230 |
| E47 | 3.1 | 64 | 64 | 17.2% | 0.35/0.62 | 40 mA/cm² | 80 | 270 |
| E48 | 3.2 | 60 | 62 | 16.5% | 0.34/0.62 | 40 mA/cm² | 80 | 245 |
| E49 | 3.2 | 62 | 61 | 17.0% | 0.34/0.62 | 40 mA/cm² | 80 | 200 |
| E50 | 2.8 | 87 | 95 | 25.6% | 0.44/0.55 | 50 mA/cm² | 90 | 345 |
| E51 | 2.8 | 86 | 96 | 25.5% | 0.45/0.55 | 50 mA/cm² | 90 | 480 |
| E52 | 2.9 | 88 | 94 | 26.0% | 0.44/0.55 | 50 mA/cm² | 90 | 210 |
| E53 | 2.9 | 85 | 92 | 25.1% | 0.44/0.55 | 50 mA/cm² | 90 | 400 |
| E54 | 3.2 | 85 | 83 | 25.0% | 0.44/0.55 | 50 mA/cm² | 90 | 185 |
| E55 | 2.9 | 87 | 95 | 25.4% | 0.45/0.55 | 50 mA/cm² | 90 | 110 |
| E56 | 3.3 | 71 | 68 | 18.9% | 0.35/0.62 | 40 mA/cm² | 80 | 235 |
| E57 | 3.4 | 70 | 65 | 18.8% | 0.35/0.62 | 40 mA/cm² | 80 | 170 |
| E58 | 3.3 | 71 | 68 | 18.9% | 0.34/0.63 | 40 mA/cm² | 80 | 270 |
| E59 | 3.2 | 74 | 72 | 19.7% | 0.34/0.63 | 40 mA/cm² | 80 | 210 |
| E60 | 3.3 | 74 | 71 | 19.7% | 0.34/0.63 | 40 mA/cm² | 80 | 165 |
| E61 | 3.4 | 70 | 64 | 18.6% | 0.34/0.62 | 40 mA/cm² | 80 | 220 |
| E62 | 3.1 | 71 | 72 | 19.0% | 0.34/0.62 | 40 mA/cm² | 80 | 170 |
| E63 | 3.0 | 76 | 79 | 20.3% | 0.34/0.63 | 40 mA/cm² | 80 | 180 |
| E64 | 3.1 | 52 | 53 | 14.4% | 0.31/0.64 | 20 mA/cm² | 90 | 395 |
| E65 | 3.2 | 53 | 52 | 14.4% | 0.31/0.64 | 20 mA/cm² | 90 | 420 |
| E66 | 3.1 | 58 | 60 | 16.0% | 0.31/0.64 | 20 mA/cm² | 90 | 460 |
| E67 | 3.3 | 58 | 56 | 15.7% | 0.31/0.64 | 20 mA/cm² | 90 | 365 |
| E68 | 3.2 | 65 | 64 | 17.9% | 0.31/0.64 | 20 mA/cm² | 90 | 300 |

TABLE 2-continued
Data for the OLEDs
| Ex. | U1000 (V) | CE1000 (cd/A) | PE1000 (lm/W) | EQE 1000 | CIE x/y at 1000 cd/m$^2$ | L0; j0 | | L1 % | LT (h) |
|---|---|---|---|---|---|---|---|---|---|
| E69 | 3.5 | 69 | 63 | 18.4% | 0.35/0.62 | 40 | mA/cm$^2$ | 80 | 235 |
| E70 | 3.4 | 65 | 60 | 17.3% | 0.35/0.62 | 40 | mA/cm$^2$ | 80 | 405 |
| E71 | 3.3 | 68 | 64 | 18.2% | 0.35/0.62 | 40 | mA/cm$^2$ | 80 | 320 |
| E72 | 3.3 | 71 | 69 | 19.0% | 0.35/0.62 | 40 | mA/cm$^2$ | 80 | 220 |
| E73 | 3.2 | 67 | 67 | 18.0% | 0.35/0.62 | 40 | mA/cm$^2$ | 80 | 325 |
| E74 | 3.1 | 70 | 71 | 18.8% | 0.35/0.61 | 40 | mA/cm$^2$ | 80 | 245 |
| E75 | 3.1 | 67 | 69 | 18.0% | 0.35/0.62 | 40 | mA/cm$^2$ | 80 | 425 |
| E76 | 3.2 | 67 | 67 | 18.1% | 0.35/0.61 | 40 | mA/cm$^2$ | 80 | 315 |
| E77 | 3.0 | 69 | 72 | 18.5% | 0.35/0.61 | 40 | mA/cm$^2$ | 80 | 220 |
TABLE 3
Structural formulae of the materials for the OLEDs
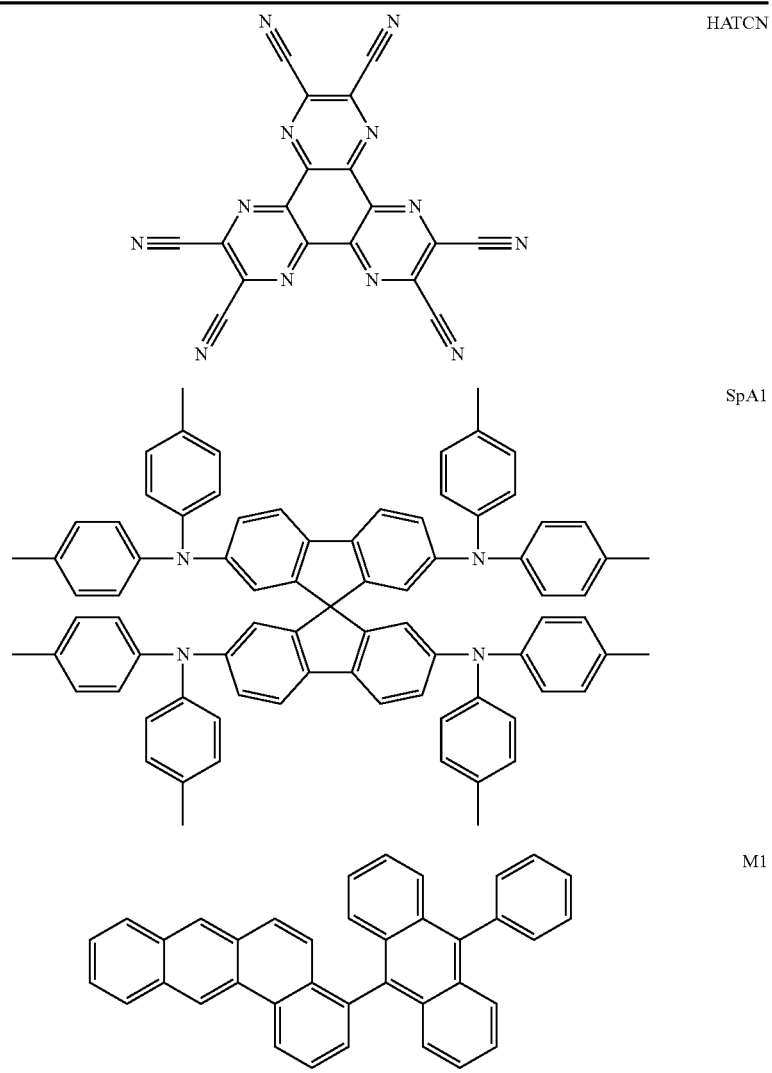

TABLE 3-continued
Structural formulae of the materials for the OLEDs
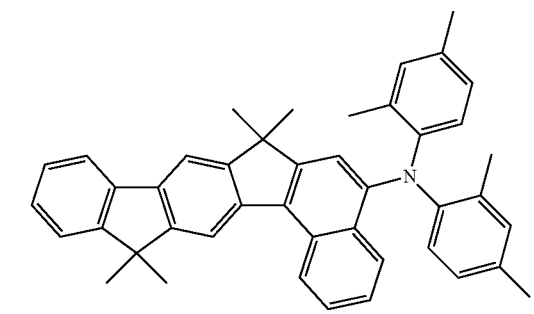 [SMILES: Cc1ccc(N(c2ccc(C)cc2C)c2cc3c(c4ccccc24)-c2cc4c(cc2C3(C)C)-c2ccccc2C4(C)C)c(C)c1]
D1
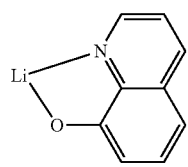
LiQ
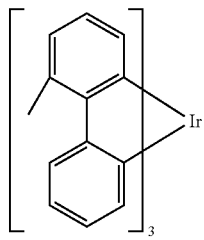
TEG1
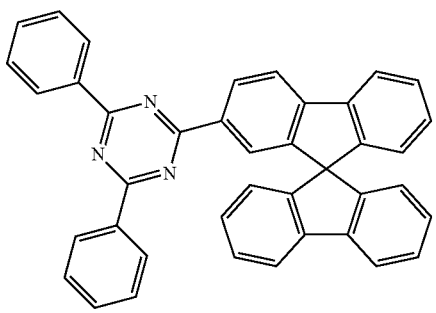 [SMILES: c1ccc(-c2nc(-c3ccccc3)nc(-c3ccc4c(c3)C3(c5ccccc5-c5ccccc53)c3ccccc3-4)n2)cc1]
ST1
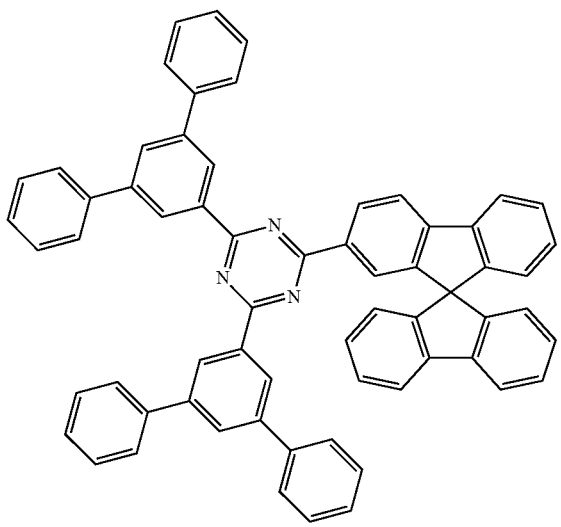 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2

TABLE 3-continued
Structural formulae of the materials for the OLEDs
IC1
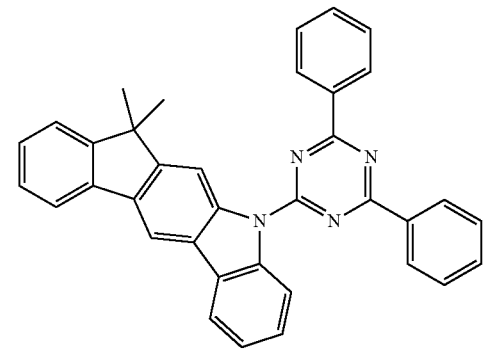 [SMILES: CC1(C)c2ccccc2-c2cc3c4ccccc4n(-c4nc(-c5ccccc5)nc(-c5ccccc5)n4)c3cc21]
IC2
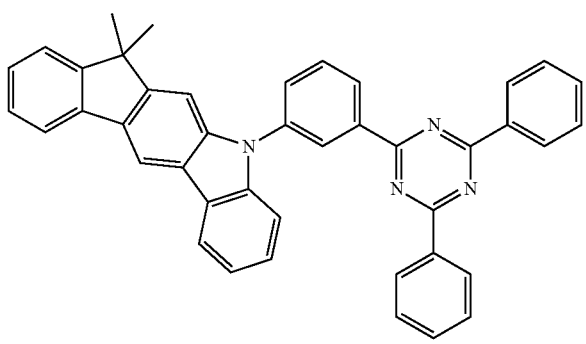 [SMILES: CC1(C)c2ccccc2-c2cc3c4ccccc4n(-c4cccc(-c5nc(-c6ccccc6)nc(-c6ccccc6)n5)c4)c3cc21]
IC3
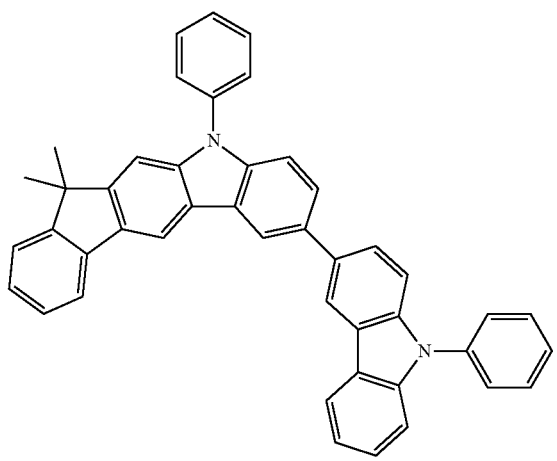 [SMILES: CC1(C)c2ccccc2-c2cc3c4cc(-c5ccc6c(c5)c5ccccc5n6-c5ccccc5)ccc4n(-c4ccccc4)c3cc21]
SpMA1
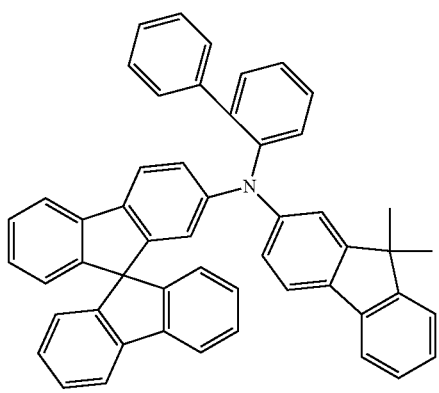 [SMILES: CC1(C)c2ccccc2-c2ccc(N(c3ccc4c(c3)C3(c5ccccc5-c5ccccc53)c3ccccc3-4)c3ccccc3-c3ccccc3)cc21]

TABLE 3-continued
Structural formulae of the materials for the OLEDs
SpMA2
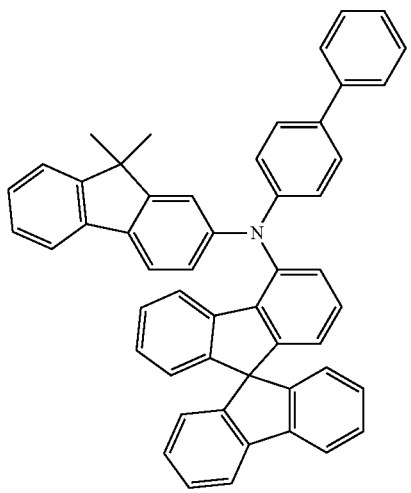 [SMILES: CC1(C)c2ccccc2-c2ccc(N(c3ccc(-c4ccccc4)cc3)c3cccc4c3-c3ccccc3C43c4ccccc4-c4ccccc43)cc21]
SpMA4
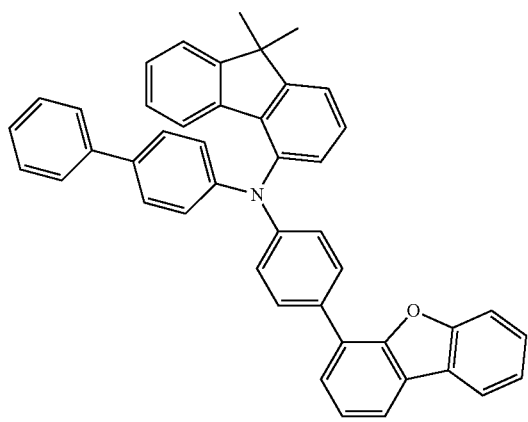 [SMILES: CC1(C)c2ccccc2-c2c(N(c3ccc(-c4ccccc4)cc3)c3ccc(-c4cccc5c4oc4ccccc45)cc3)cccc21]
SpMA5
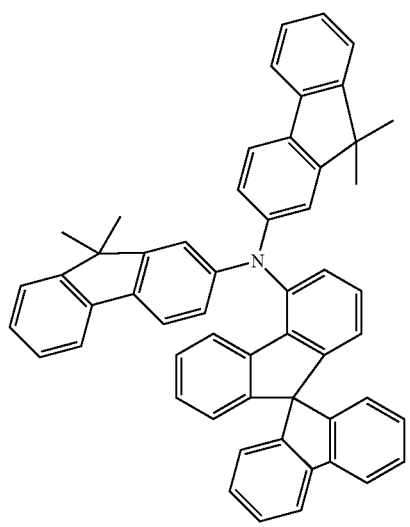 [SMILES: CC1(C)c2ccccc2-c2ccc(N(c3ccc4c(c3)C(C)(C)c3ccccc3-4)c3cccc4c3-c3ccccc3C43c4ccccc4-c4ccccc43)cc21]

TABLE 3-continued
Structural formulae of the materials for the OLEDs
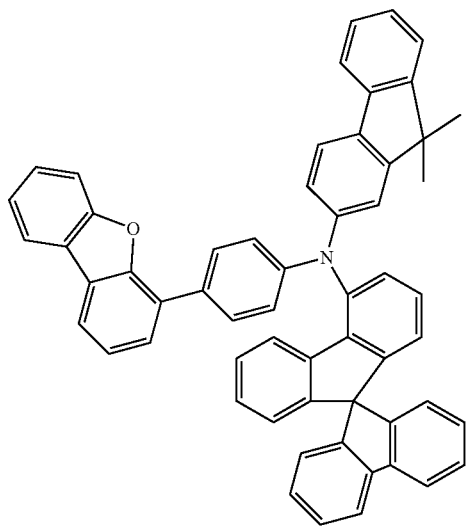 [SMILES: CC1(C)c2ccccc2-c2ccc(N(c3ccc(-c4cccc5c4oc4ccccc45)cc3)c3cccc4c3-c3ccccc3C43c4ccccc4-c4ccccc43)cc21]
SpMA6
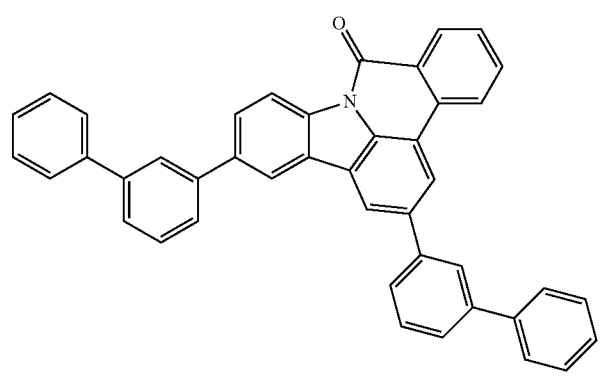 [SMILES: O=c1c2ccccc2c2cc(-c3cccc(-c4ccccc4)c3)cc3c4cc(-c5cccc(-c6ccccc6)c5)ccc4n1c23]
L2
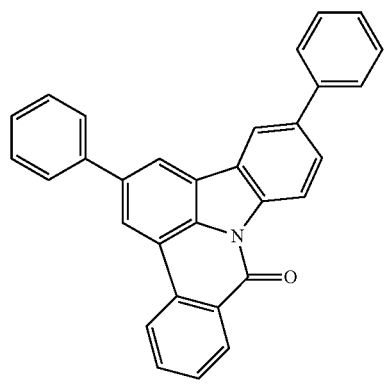 [SMILES: O=c1c2ccccc2c2cc(-c3ccccc3)cc3c4cc(-c5ccccc5)ccc4n1c23]
L1

TABLE 3-continued
Structural formulae of the materials for the OLEDs
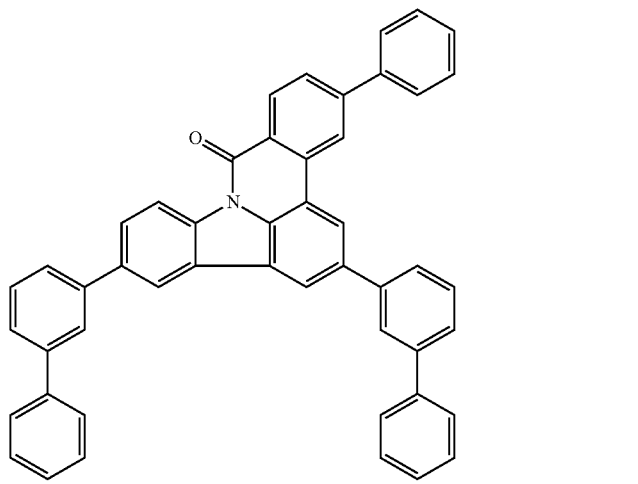 [SMILES: O=c1c2ccc(-c3ccccc3)cc2c2cc(-c3cccc(-c4ccccc4)c3)cc3c4cc(-c5cccc(-c6ccccc6)c5)ccc4n1c23]
L3
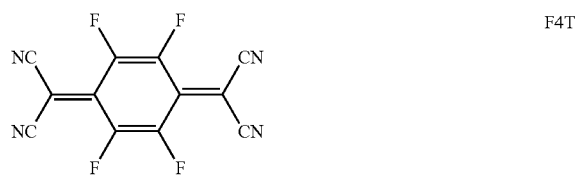
F4T
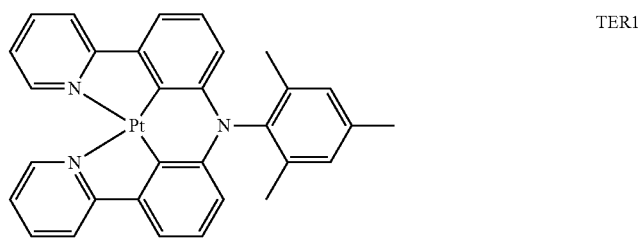
TER1
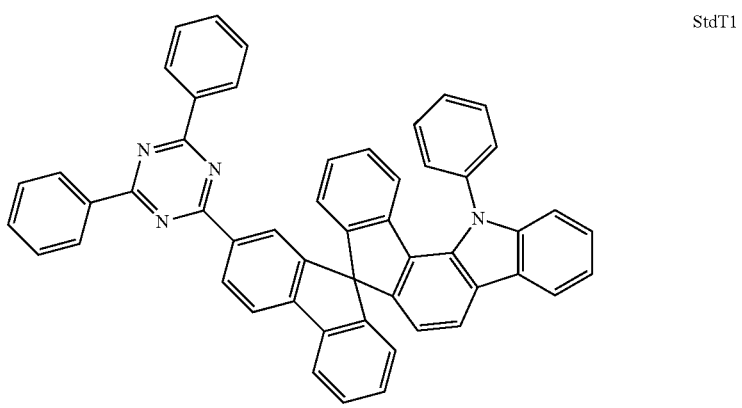
StdT1

TABLE 3-continued
Structural formulae of the materials for the OLEDs
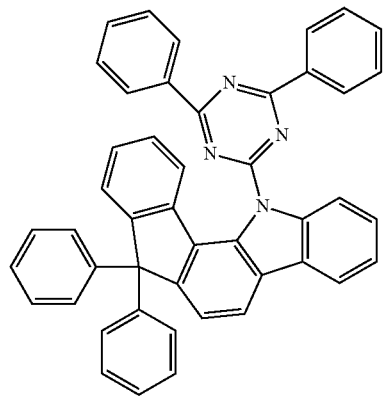 [SMILES: c1ccc(-c2nc(-c3ccccc3)nc(-n3c4ccccc4c4ccc5c(c43)-c3ccccc3C5(c3ccccc3)c3ccccc3)n2)cc1] StdT2
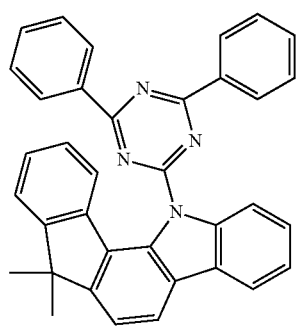 [SMILES: CC1(C)c2ccccc2-c2c1ccc1c3ccccc3n(-c3nc(-c4ccccc4)nc(-c4ccccc4)n3)c21] StdT3
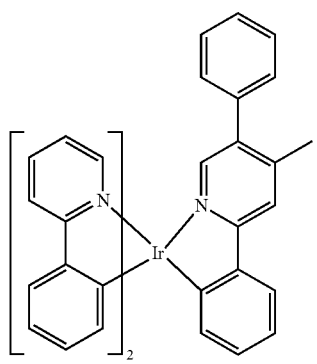 TEG2

TABLE 3-continued
Structural formulae of the materials for the OLEDs
IC5
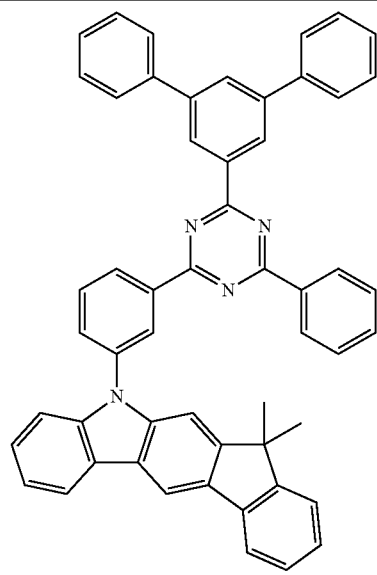
TEY1
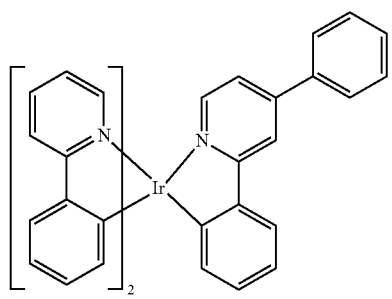
SpMA3
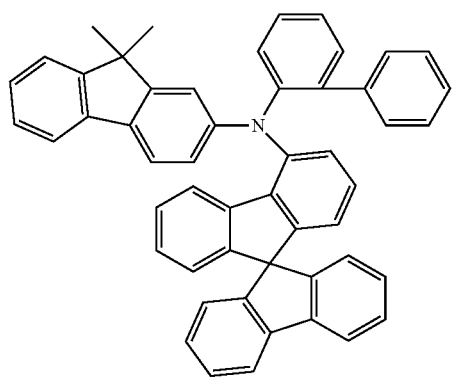 [SMILES: CC1(C)c2ccccc2-c2ccc(N(c3ccccc3-c3ccccc3)c3cccc4c3-c3ccccc3C43c4ccccc4-c4ccccc43)cc21]

TABLE 3-continued
Structural formulae of the materials for the OLEDs
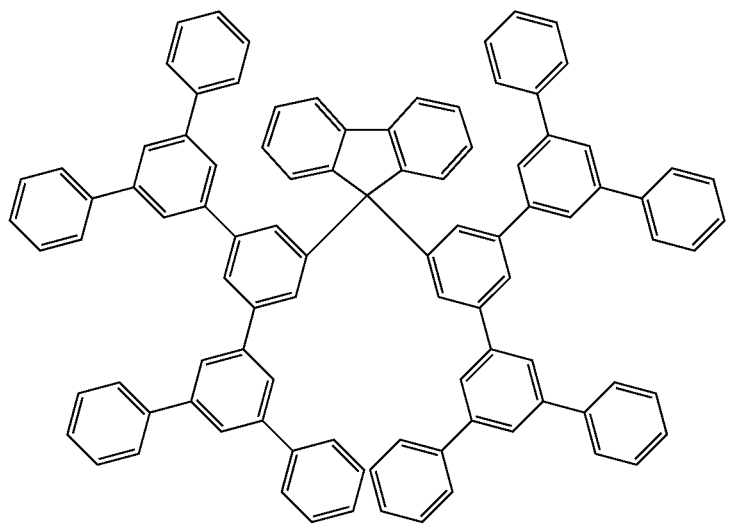 [SMILES: c1ccc(-c2cc(-c3ccccc3)cc(-c3cc(-c4cc(-c5ccccc5)cc(-c5ccccc5)c4)cc(C4(c5cc(-c6cc(-c7ccccc7)cc(-c7ccccc7)c6)cc(-c6cc(-c7ccccc7)cc(-c7ccccc7)c6)c5)c5ccccc5-c5ccccc54)c3)c2)cc1]
WB1
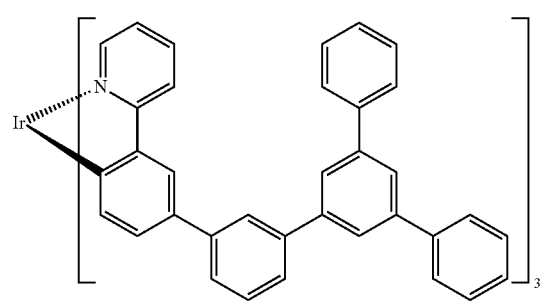
TEG3
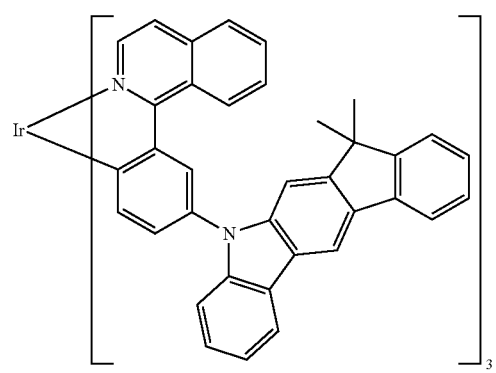
TER2

TABLE 3-continued

Structural formulae of the materials for the OLEDs

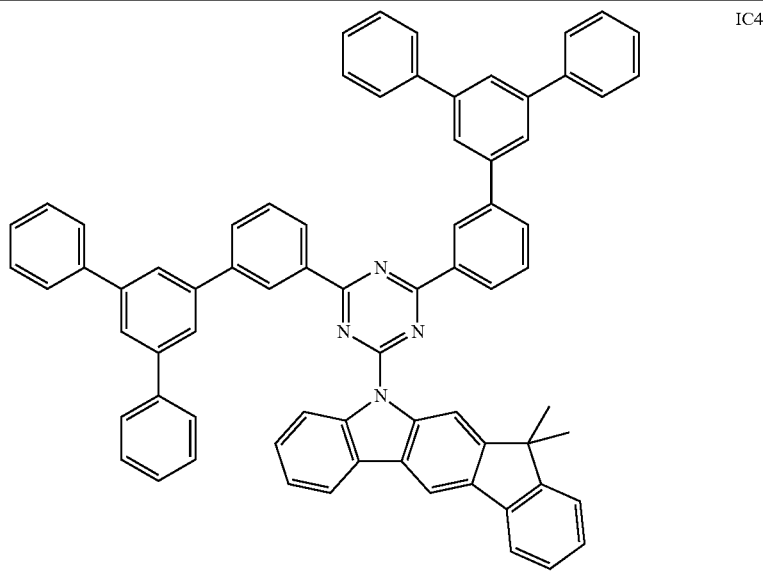

IC4

Example 17: OLEDs Having a Hole-Transport and Emission Layer Processed From Solution Many of the materials according to the invention can also be processed from solution and, compared with vacuum-processed OLEDs, result in OLEDs which are significantly easier to produce, but nevertheless have good properties. In particular, matrix materials according to the invention have a positive influence on operating lifetime and efficiency of components having a solution-processed emission layer. The production of fully solution-based OLEDs has already been described many times in the literature, for example in WO 2004/037887.

In the examples discussed below, layers applied on a solution basis and on a vacuum basis are combined within an OLED, so that the processing up to and including the emission layer is carried out from solution and in the subsequent layers is carried out by thermal evaporation in vacuo. The general processes described above are for this purpose adapted to the circumstances described here (layer-thickness variation, materials) and combined as follows.

Cleaned glass plates (cleaning in Miele laboratory dishwasher, Merck Extran detergent) which have been coated with structured ITO (indium tin oxide) in a thickness of 50 nm are coated with 20 nm (for green-emitting OLEDs) or 80 nm (for red-emitting OLEDs) of PEDOT:PSS (poly(3,4-ethylenedioxythiophene)poly(styrene sulfonate), purchased as CLEVIOS™ P VP Al 4083 from Heraeus Precious Metals GmbH, Germany, applied by spin-coating from aqueous solution) for improved processing. These substrates are subsequently dried by heating at 180° C. for 10 min.

A hole-transport layer having a thickness of 20 nm is applied to these substrates. It consists of a polymer of the following structural formula,

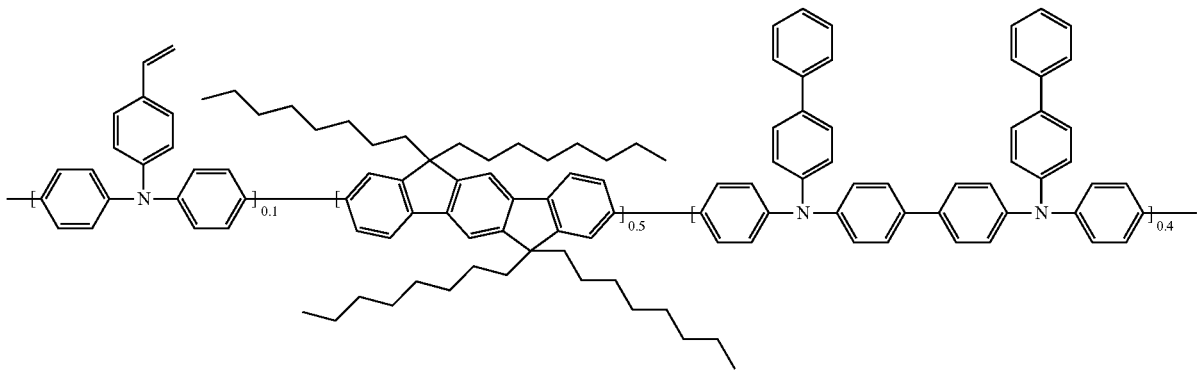

which has been synthesised in accordance with WO 2010/097155. The material is dissolved in toluene. The solids content of the solution is 5 g/l. A layer with a thickness of 20 nm is applied therefrom by means of spin coating in a nitrogen atmosphere. The sample is subsequently dried by heating at 180° C. for 60 minutes in a nitrogen atmosphere.

The emission layer is then applied. This is always composed of at least one matrix material (host material) and an emitting dopant (emitter). Furthermore, mixtures of a plurality of matrix materials and co-dopants may occur. An expression such as matrix(92%):dopant(8%) means that the matrix material is present in a proportion by weight of 92% and the dopant in a proportion by weight of 8% in the solution from which the emission layer is produced. A corresponding solids mixture for the emission layer is dissolved in toluene. The solids content is 18 g/l. The emission layer is applied by spin coating in a nitrogen atmosphere and dried by heating at 180° C. for 10 minutes in the nitrogen atmosphere.

The samples are subsequently introduced into a vacuum chamber without contact with air, and two further layers are applied by evaporation. If one such layer consists of a plurality of materials, the nomenclature described above applies to the mixing ratios of the individual components.

The OLEDs are characterised as described above. For the measurement of the lifetime, the OLEDs are operated at a constant current, which is set so that a certain initial luminous density is achieved. The lifetime LT80@ 8000 is defined as the time by which the luminous density has dropped from its initial value of 8000 cd/m$^2$ to 80%, i.e. to 6400 cd/m$^2$. Lifetime values at other initial luminances or other percentage final luminous densities are defined correspondingly.

Comparative Example LV1

In accordance with the prior art, a solids mixture IC4 (40%):WB1(40%):TEG3(20%) is used for the emission layer. An emission layer with a thickness of 60 nm is produced therefrom as described above. A layer of material ST2 with a thickness of 10 nm and then a layer ST2:LiQ (50%:50%) with a thickness of 40 nm are subsequently applied by thermal evaporation in vacuo. An aluminium layer with a thickness of 100 nm is subsequently applied as cathode by evaporation in vacuo. The OLED emits green, and U1000=4.6 V, EQE1000=17.8%, LT80@ 10000=115 h, LT90@ 10000=28 h, are obtained.

Example LE1 According to the Invention

The OLED corresponds to Example LV1, with the difference that instead of mixture IC4(40%):WB1(40%): TEG3 (20%), mixture 3q(40%):WB1(40%):TEG3(20%) is used. The OLED emits green, and U1000=4.6 V, EQE1000=18.3%, LT80@ 10000=120 h, LT90@ 10000=37 h, are obtained.

Example LE2 According to the Invention

The OLED corresponds to Example LV1, with the difference that instead of mixture IC4(40%):WB1(40%): TEG3 (20%), mixture 3p(40%):WB1(40%):TEG3(20%) is used. The OLED emits green, and U1000=4.5 V, EQE1000=18.4%, LT80@ 10000=130 h, LT90@ 10000=38 h, are obtained.

Example LE3 According to the Invention

The OLED corresponds to Example LV1, with the difference that instead of mixture IC4(40%): WB1(40%):TEG3 (20%), mixture 3a(40%):WB1(40%):TEG3(20%) is used. The OLED emits green, and U1000=4.4 V, EQE1000=18.8%, LT80@ 10000=240 h, LT90@ 10000=75 h, are obtained.

Comparative Example LV2

The OLED corresponds to Example LV1, with the difference that instead of mixture IC4(40%):WB1(40%):TEG3 (20%), mixture IC5(40%):WB1(30%):TEG3(30%) is used. The OLED emits green, and U1000=4.0 V, EQE1000=19.7%, LT80@ 10000=335 h, LT90@ 10000=87 h, are obtained.

Example LE4 According to the Invention

The OLED corresponds to Example LV2, with the difference that instead of mixture IC5(40%):WB1(30%) TEG3 (30%), mixture 3a(40%):WB1(30%):TEG3(30%) is used. The OLED emits green, and U1000=4.0 V, EQE1000=21.4%, LT80@ 10000=520 h, LT90@ 10000=195 h, are obtained.

Comparative Example LV3

The OLED corresponds to Example LV1, with the difference that instead of mixture IC4(40%):WB1(40%):TEG3 (20%), mixture IC5(40%):WB1(24%):TEG3(30%):TER2 (6%) is used. The OLED emits red, and U1000=6.0 V, EQE1000=13.5%, LT80@ 8000=180 h, LT90@ 8000=48 h, are obtained.

Example LE5 According to the Invention

The OLED corresponds to Example LV3, with the difference that instead of mixture IC5(40%):WB1(24%): TEG3 (30%):TER2(6%), mixture 3a(40%):WB1(24%):TEG3 (30%):TER2(6%) is used. The OLED emits red, and U1000=5.6 V, EQE1000=13.8%, LT80@ 8000=255 h, LT90@ 8000=82 h, are obtained.

Example LE6 According to the Invention

The OLED corresponds to Example LV3, with the difference that instead of mixture 105(40%): WB1(24%):TEG3 (30%):TER2(6%), mixture 3p(40%):WB1(24%): TEG3 (30%):TER2(6%) is used. The OLED emits red, and U1000=6.0 V, EQE1000=13.8%, LT80@ 8000=275 h, LT90@ 8000=81 h, are obtained.

Example LE7 According to the Invention

The OLED corresponds to Example LV3, with the difference that instead of mixture IC5(40%):WB1(24%): TEG3 (30%):TER2(6%), mixture 3q(40%):WB1(24%):TEG3 (30%):TER2(6%) is used. The OLED emits red, and U1000=6.0 V, EQE1000=14.0%, LT80@ 8000=250 h, LT90@ 8000=68 h, are obtained.

Comparative Example LV4

In accordance with the prior art, a solids mixture IC4 (40%):WB1(40%):TEG3(20%) is used for the emission layer. An emission layer with a thickness of 60 nm is produced therefrom as described above. A layer M1:D1 (95%:5%) with a thickness of 20 nm and then a layer ST2:LiQ(50%:50%) with a thickness of 20 nm are subsequently applied by thermal evaporation in vacuo. An aluminium layer with a thickness of 100 nm is subsequently applied as cathode by evaporation in vacuo. The OLED emits green, and U1000=5.0 V, EQE1000=16.7%, LT80@ 10000=33 h, LT90@ 10000=8 h, are obtained.

Comparative Example LV5

The OLED corresponds to Example LV4, with the difference that instead of mixture IC4(40%):WB1(40%):TEG3 (20%), mixture IC5(40%):WB1(40%):TEG3(20%) is used. The OLED emits green, and U1000=4.3 V, EQE1000=15.0%, LT80@ 10000=29 h, LT90@ 10000=8 h, are obtained.

Example LE8 According to the Invention

The OLED corresponds to Example LV4, with the difference that instead of mixture IC4(40%):WB1(40%);TEG3 (20%), mixture 3a(40%):WB1(40%):TEG3(20%) is used. The OLED emits green, and U1000=4.3 V, EQE1000=16.9%, LT80@ 10000=88 h, LT90@ 10000=25 h, are obtained.

As can be seen by comparing Examples LV1 with LE1-LE3, LV2 with LE4, LV3 with LE5-LE7 and LV4 and LV5 with LE8, improvements in all parameters, in particular a very significant increase in the LT90, which is important for display applications, are obtained with mixtures comprising compounds according to the invention.

The invention claimed is:

1. A compound of the formula (1) or formula (1A),

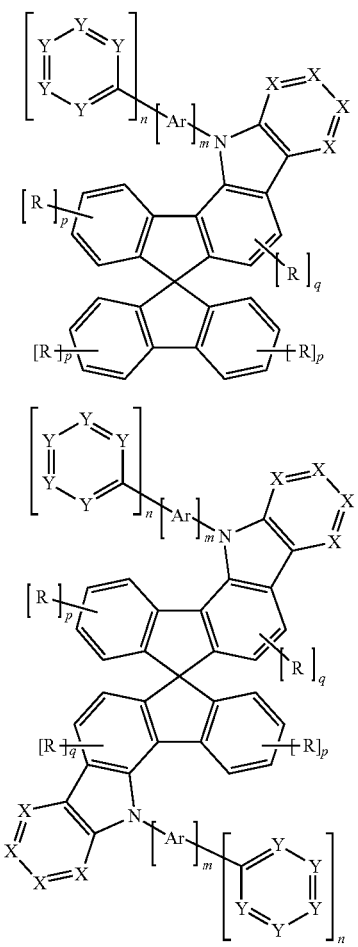

where the following applies to the symbols and indices used:

Y is on each occurrence, identically or differently, $CR^1$ or N, with the proviso that at least one group Y stands for N;

X is on each occurrence, identically or differently, $CR^1$ or N; or two adjacent X stand for S, O or $NR^1$, so that a five-membered ring forms; or two adjacent X stand for a group of the following formula (2), (3) or (4),

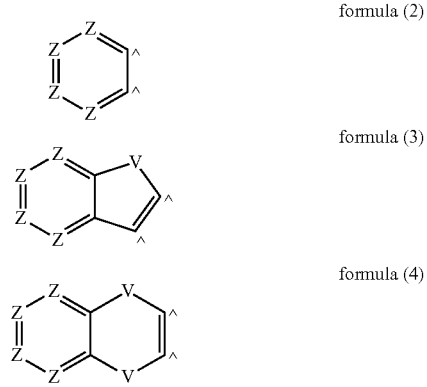

where ^ indicates the corresponding adjacent groups X in the formula (1);

V is on each occurrence, identically or differently, $C(R^1)_2$, $NR^1$, O, S, $BR^1$, $Si(R^1)_2$ or C=O;

Z is on each occurrence, identically or differently, $CR^1$ or N;

Ar is on each occurrence, identically or differently, an aromatic or heteroaromatic ring system having 5 to 40 aromatic ring atoms, which is optionally substituted by one or more radicals $R^1$;

R is on each occurrence, identically or differently, H, D, F, Cl, Br, I, CN, $N(Ar^1)_2$, a straight-chain alkyl group having 1 to 40 C atoms or a branched or cyclic alkyl group having 3 to 40 C atoms, each of which is optionally substituted by one or more radicals $R^2$, where one or more non-adjacent $CH_2$ groups is optionally replaced by $R^2C=CR^2$, C≡C or O and where one or more H atoms is optionally replaced by D or F, or an aromatic ring system having 6 to 60 aromatic ring atoms, which is optionally substituted by one or more radicals $R^2$; wherein the aromatic ring system is selected from benzene, ortho-, meta-para-biphenyl, ortho-, meta-, para- or branched terphenyl, ortho-, meta-, para- or branched quaterphenyl, 1-, 2- or 3-fluorenyl, 1-, 2-, 3- or 4-spirobifluorenyl, 1- or 2-naphthyl, phenanthrene, or combinations of two or three of these groups, each of which may be substituted by one or more radicals $R^1$; two adjacent substituents R here may form a monocyclic or polycyclic, aliphatic or aromatic ring system, which is optionally substituted by one or more radicals $R^2$;

$R^1$ is on each occurrence, identically or differently, H, D, F, Cl, Br, I, CN, $NO_2$, $N(Ar^1)_2$, $N(R^2)_2$, C(=O)$Ar^1$, C(=O)$R^2$, P(=O)$(Ar^1)_2$, $P(Ar^1)_2$, $B(Ar^1)_2$, $Si(Ar^1)_3$, $Si(R^2)_3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals R², where one or more non-adjacent CH₂ groups is optionally replaced by R²C=CR², C≡C, Si(R²)₂, C=O, C=S, C=NR², P(=O)(R²), SO, SO₂, NR², O, S or CONR² and where one or more H atoms is optionally replaced by D, F, Cl, Br, I, CN or NO₂, an aromatic or heteroaromatic ring system having 5 to 60 aromatic ring atoms, which may in each case be substituted by one or more radicals R², an aryloxy or heteroaryloxy group having 5 to 60 aromatic ring atoms, which is optionally substituted by one or more radicals R²; two adjacent substituents R¹ here may optionally form a monocyclic or polycyclic, or aliphatic ring system, which is optionally substituted by one or more radicals R²;

Ar¹ is on each occurrence, identically or differently, an aromatic or heteroaromatic ring system having 5-30 aromatic ring atoms, which is optionally substituted by one or more non-aromatic radicals R²; two radicals Ar¹ here which are bonded to the same N atom or P atom may also be bridged to one another by a single bond or a bridge selected from N(R²), C(R²)₂, O or S;

R² is selected on each occurrence, identically or differently, from the group consisting of H, D, F, CN, an aliphatic hydrocarbon radical having 1 to 20 C atoms, or an aromatic or heteroaromatic ring system having 5 to 30 aromatic ring atoms, in which one or more H atoms is optionally replaced by D, F, Cl, Br, I or CN, where two or more adjacent substituents R² may form a mono- or polycyclic, aliphatic ring system with one another;

m and n are on each occurrence, identically or differently, 0 or 1, with the proviso that m+n≥1;

p is on each occurrence, identically or differently, 0, 1, 2, 3 or 4;

q is 0, 1 or 2.

2. The compound according to claim 1, wherein the X stands, identically or differently on each occurrence, for the CR¹ or the N, where a maximum of one group X per ring stands for the N; or the two adjacent groups X stand for a group of the formula (2) or (3), where the Z stands, identically or differently on each occurrence, for the CR¹ and the V stands, identically or differently on each occurrence, for the NR¹, the C(R¹)₂, the O or the S.

3. The compound according to claim 1, wherein the compound is selected from the compounds of the formulae (5) to (12), formula (5)

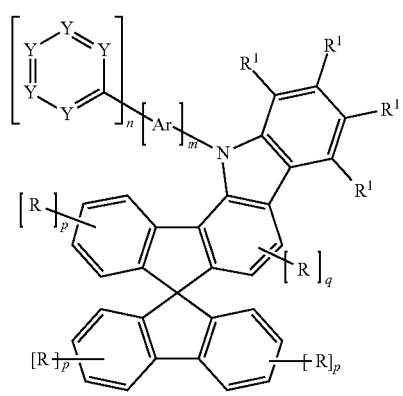

formula (6)

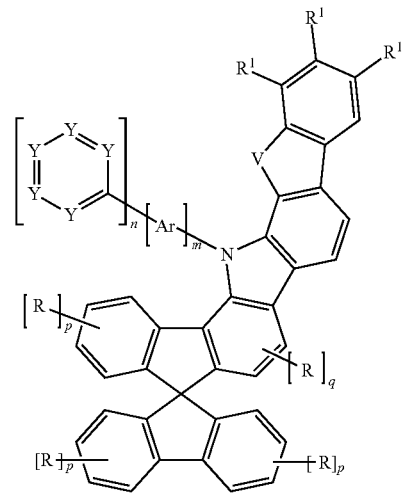

formula (7)

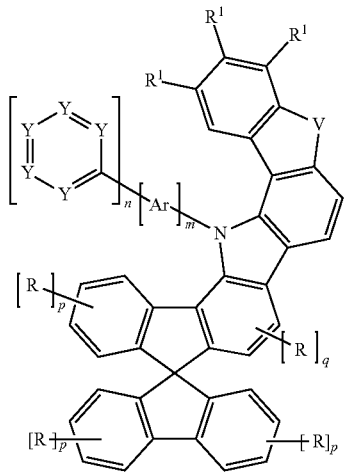

formula (8)

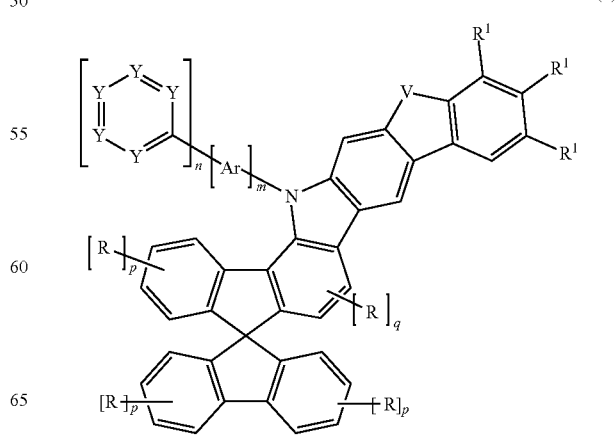

formula (9)
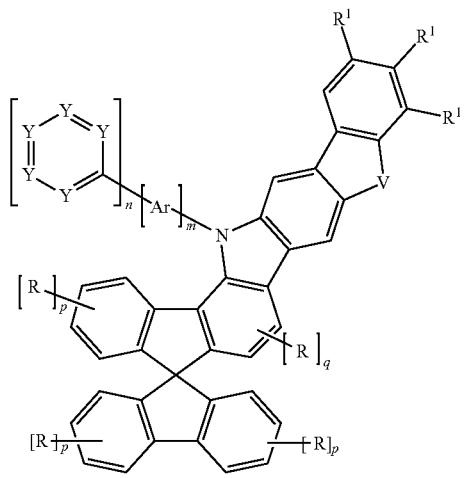
formula (10)
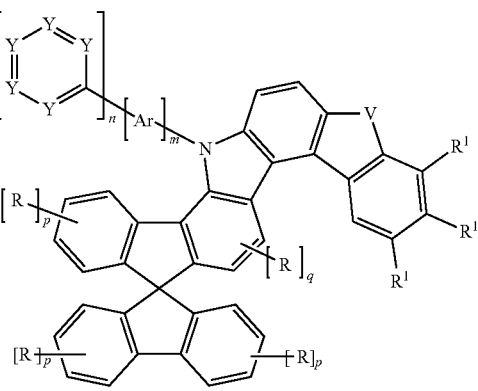
formula (11)
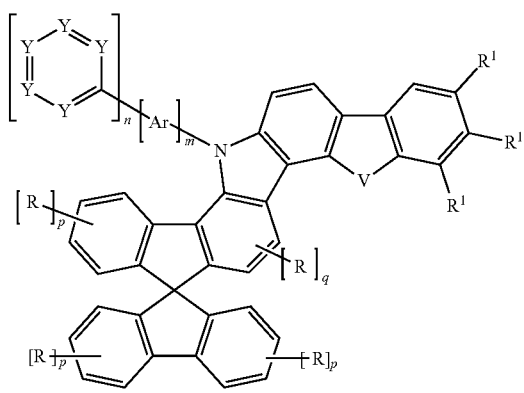
formula (12)
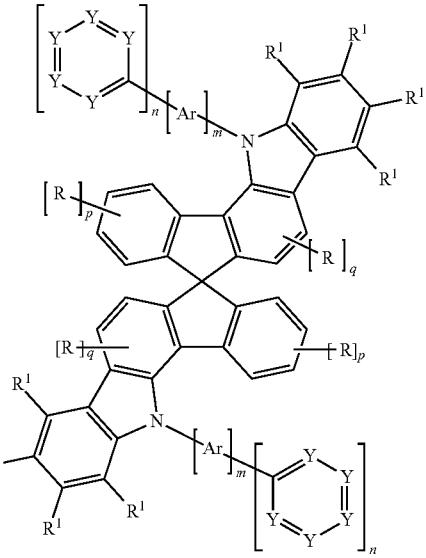
where the symbols and indices used have the meanings given in claim 1, and the V stands for the $NR^1$, the $C(R^1)_2$, the O or the S.
4. The compound according to claim 1, wherein the compound is selected from the structures of the formulae (5a) to (12a),
formula (5a)
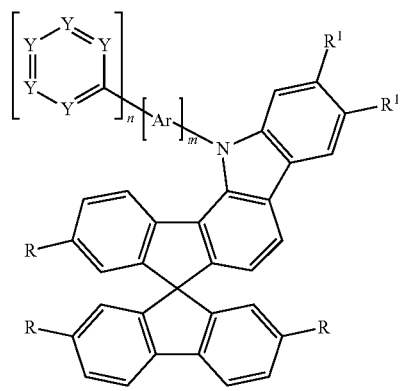
formula (6a)
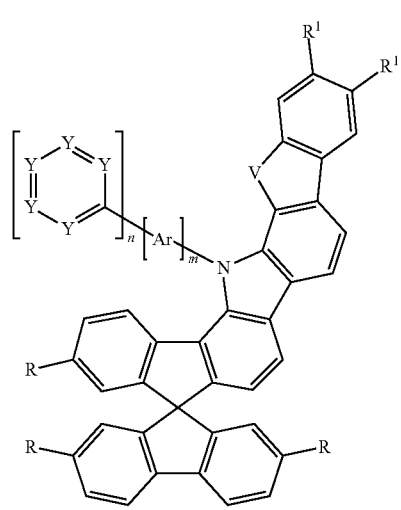

formula (7a)

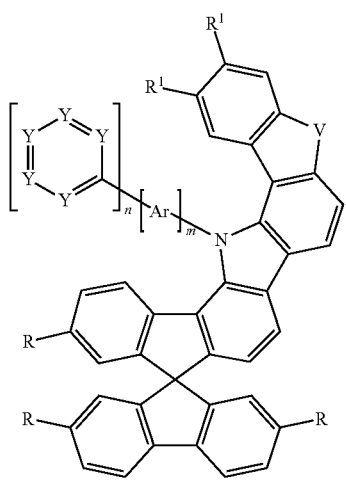

formula (8a)

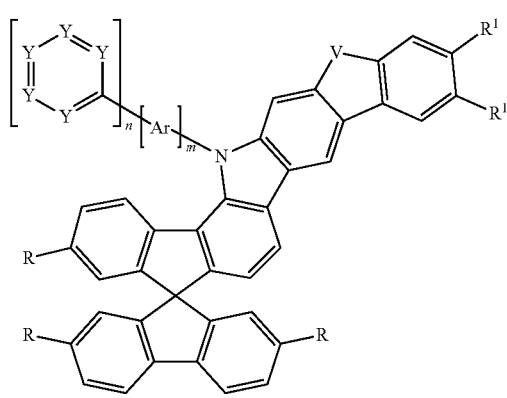

formula (9a)

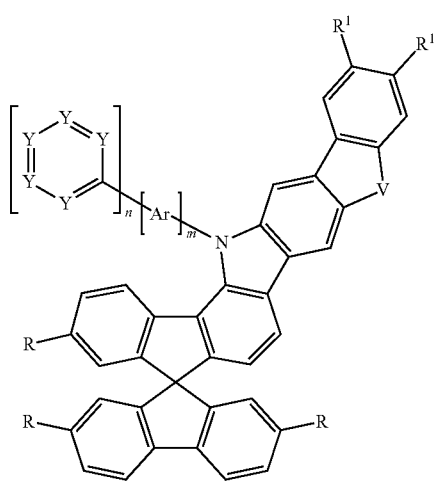

formula (10a)

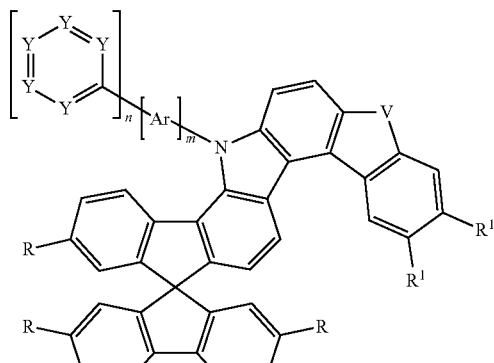

formula (11a)

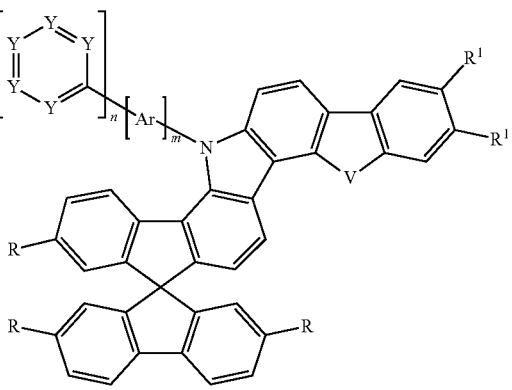

formula (12a)

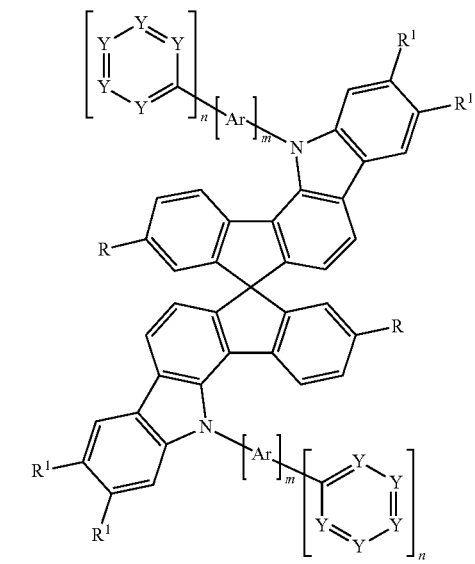

where the symbols and indices used have the meanings given in claim 1.

5. The compound according to claim 1, wherein the R is selected, identically or differently on each occurrence, from the group consisting of H, F, CN, N(Ar$^1$)$_2$, a straight-chain alkyl group having 1 to 10 C atoms or a branched or cyclic alkyl group having 3 to 10 C atoms or an aromatic ring system having 6 to 30 aromatic ring atoms, where the aromatic ring system does not contain heteroaryl groups, which is optionally substituted by one or more non-aromatic radicals R², and wherein the aromatic ring system is selected from benzene, ortho-, meta-para-biphenyl, ortho-, meta-, para- or branched terphenyl, ortho-, meta-, para- or branched quaterphenyl, 1-, 2- or 3-fluorenyl, 1-, 2-, 3- or 4-spirobifluorenyl, 1- or 2-naphthyl, phenanthrene, or combinations of two or three of these groups, each of which may be substituted by one or more radicals R¹ and in that the R¹ is selected, identically or differently on each occurrence, from the group consisting of H, D, F, Br, CN, N(Ar¹)₂, C(=O)Ar¹, P(=O)(Ar¹)₂, a straight-chain alkyl or alkoxy group having 1 to 10 C atoms or a branched or cyclic alkyl or alkoxy group having 3 to 10 C atoms or an alkenyl or alkynyl group having 2 to 10 C atoms, each of which is optionally substituted by one or more radicals R², where one or more non-adjacent CH₂ groups is optionally replaced by O and where one or more H atoms is optionally replaced by D or F, an aromatic or heteroaromatic ring system having 5 to 30 aromatic ring atoms, which may in each case be substituted by one or more radicals R².

6. The compound according to claim 1, wherein the Ar is selected from aromatic or heteroaromatic ring systems having 5 to 24 aromatic ring atoms, which may in each case be substituted by one or more radicals R¹, each of which is optionally substituted by one or more radicals R¹.

7. The compound according to claim 1, wherein the Ar is benzene, ortho-, meta- or para-biphenyl, ortho-, meta-, para- or branched terphenyl, ortho-, meta-, para- or branched quaterphenyl, 1-, 2- or 3-fluorenyl, 1-, 2-, 3- or 4-spirobifluorenyl, 1- or 2-naphthyl, pyrrole, furan, thiophene, indole, benzofuran, benzothiophene, 1-, 2- or 3-carbazole, 1-, 2- or 3-dibenzofuran, 1-, 2- or 3-dibenzothiophene, indenocarbazole, indolocarbazole, 2-, 3- or 4-pyridine, 2-, 4- or 5-pyrimidine, pyrazine, pyridazine, triazine, anthracene, phenanthrene, triphenylene, pyrene, benzanthracene, or combinations of two or three of these groups, each of which is optionally substituted by one or more radicals R¹.

8. The compound according to claim 1, wherein, in the group of the following formula (Het-Ar),

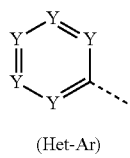

(Het-Ar)

which is present in the compound according to claim 1 for n=1 and which is bonded to the Ar or, for m=0, to the nitrogen, at least one group Y and a maximum of three groups Y stand for N and the other groups Y stand for CR¹.

9. The compound according to claim 8, wherein the group (Het-Ar) is selected from the groups of the formulae (Het-Ar-1) to (Het-Ar-10),

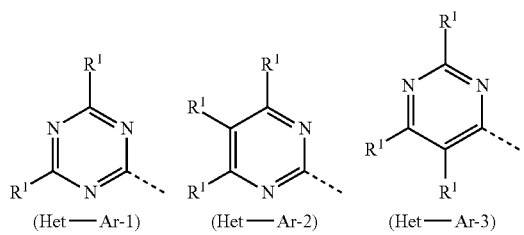

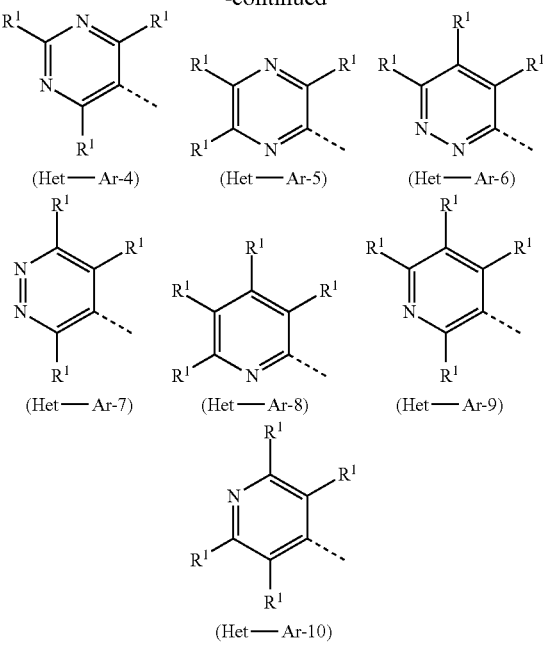

wherein the dashed bond represents the bond to the Ar or, for m=0, the bond to the nitrogen, and R¹ is on each occurrence, identically or differently, H, D, F, Cl, Br, I, CN, NO₂, N(Ar¹)₂, N(R²)₂, C(=O)Ar¹, C(=O)R², P(=O)(Ar¹)₂, P(Ar¹)₂, B(Ar¹)₂, Si(Ar¹)₃, Si(R²)₃, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals R², where one or more non-adjacent CH₂ groups is optionally replaced by R²C=CR², C≡C, Si(R²)₂, C=O, C=S, C=NR², P(=O)(R²), SO, SO₂, NR², O, S or CONR² and where one or more H atoms is optionally replaced by D, F, Cl, Br, I, CN or NO₂, an aromatic or heteroaromatic ring system having 5 to 60 aromatic ring atoms, which may in each case be substituted by one or more radicals R², an aryloxy or heteroaryloxy group having 5 to 60 aromatic ring atoms, which is optionally substituted by one or more radicals R²; two adjacent substituents R¹ here may optionally form a monocyclic or polycyclic, aliphatic, aromatic or heteroaromatic ring system, which is optionally substituted by one or more radicals R²;

Ar¹ is on each occurrence, identically or differently, an aromatic or heteroaromatic ring system having 5-30 aromatic ring atoms, which is optionally substituted by one or more non-aromatic radicals R²; two radicals Ar¹ here which are bonded to the same N atom or P atom may also be bridged to one another by a single bond or a bridge selected from N(R²), C(R²)₂, O or S;

R² is selected on each occurrence, identically or differently, from the group consisting of H, D, F, CN, an aliphatic hydrocarbon radical having 1 to 20 C atoms, or an aromatic or heteroaromatic ring system having 5 to 30 aromatic ring atoms, in which one or more H atoms is optionally replaced by D, F, Cl, Br, I or CN, where two or more adjacent substituents R² may form a mono- or polycyclic, aliphatic ring system with one another.

10. The compound according to claim 1, wherein the compound contains no condensed aryl or heteroaryl groups in which more than two six-membered rings are condensed directly onto one another.

11. A process for the preparation of the compound according to claim 1, comprising the reaction steps:
   a) synthesis of the skeleton of compound (1) or (1A) which as yet contains no group (Het-Ar) and/or Ar; and
   b) reacting the skeleton from a) in a C—C coupling or C—N coupling.

12. The process as claimed in claim 1, wherein the C—C coupling is Suzuki, Negishi, Yamamoto, Grignard-Cross or Stille coupling, or the C—N coupling is Buchwald or Ullmann coupling.

13. An oligomer, polymer or dendrimer containing one or more of the compounds according to claim 1, where one or more bonds from the compound to the polymer, oligomer or dendrimer are present instead of substituents at one or more positions.

14. A formulation comprising at least one of the compound according to claim 1 and at least one solvent.

15. A formulation comprising the oligomer, polymer or dendrimer according to claim 13 and at least one solvent.

16. An electronic device comprising at least one of the compound according to claim 1.

17. An electronic device comprising the oligomer, polymer or dendrimer according to claim 11.

18. The electronic device as claimed in claim 17 wherein the device is selected from the group consisting of an organic electroluminescent device, an organic integrated circuit, an organic field-effect transistor, an organic thin-film transistor, an organic light-emitting transistor, an organic solar cell, a dye-sensitised organic solar cell, an organic optical detector, an organic photoreceptor, an organic field-quench device, a light-emitting electrochemical cell, an organic laser diode and an organic plasmon emitting device.

19. An organic electroluminescent device which comprises the compound according to claim 1 is employed as matrix material for phosphorescent or fluorescent emitters and/or in an electron-blocking or exciton-blocking layer and/or in a hole-transport layer and/or in a hole-blocking layer and/or in a hole-blocking or electron-transport layer.

* * * * *